United States Patent [19]
Bertelsen et al.

[11] Patent Number: 5,608,221
[45] Date of Patent: Mar. 4, 1997

[54] MULTI-HEAD NUCLEAR MEDICINE CAMERA FOR DUAL SPECT AND PET IMAGING WITH MONUNIFORM ATTENUATION CORRECTION

[75] Inventors: Hugo Bertelsen; Peter Nellemann, both of Pleasanton; Matthew J. Murphy, Los Altos; Donald R. Wellnitz, Pleasanton; Horace H. Hines, San Jose, all of Calif.

[73] Assignee: ADAC Laboratories, Milpitas, Calif.

[21] Appl. No.: 488,871

[22] Filed: Jun. 9, 1995

[51] Int. Cl.⁶ .......................... G01T 1/161; G01T 1/166
[52] U.S. Cl. .............................. 250/363.03; 250/363.04; 250/369
[58] Field of Search .................... 250/363.03, 363.04, 250/369

[56] References Cited

PUBLICATIONS

Tanaka et al., "Engineering Aspects of a Hybrid Emission Computed Tomograph", IEEE Transactions on Nuclear Science, vol. NS–28, No. 1, 1981, pp. 137–141.
Hirose et al., "A Hybrid Emission CT–Headtome II", IEEE Transactions on Nuclear Science, vol. NS–29, No. 1, pp. 520–523, 1982.
Bailey et al., "Improved SPECT Using Simultaneous Emission and Transmission Tomography", Journal of Nuc. Med., vol. 28, No. 5, 1987, pp. 844–851.
Thompson et al., "Simultaneous Transmission and Emission Scans in Position Emission Tomography", IEEE Nuclear Science Symposium, 1988, pp. 1–6.
A. M. J. Paans, et al., "Performance Parameters of a Longitudinal Tomographic Positron Imaging System," reprinted from Nuclear Instruments & Methods, vol. 192, pp. 491–500 (1982).
G. Muehllehner, et al., "Performance of a Positron Imaging Camera," IEEE Transactions on Nuclear Science, vol. NS–23, No. 1, pp. 528–537 (Feb. 1976).

*Primary Examiner*—Edward J. Glick
*Attorney, Agent, or Firm*—Blakely Sokoloff Taylor & Zafman LLP

[57] ABSTRACT

A dual head nuclear camera system automatically switchable (and optimized) to perform either SPECT imaging or PET imaging that utilizes attenuation correction for nonuniform attenuation in SPECT or PET modes. The dual head detectors contain switchable triggering circuitry so that coincidence detection for PET imaging and non-coincidence detection for SPECT imaging is available. The system uses a variable integration technique with programmable integration interval; variable sized clusters for centroiding, use of dual integrators per PMT channel, the event detection and acquisition circuitry of the camera system is switchable for PET and SPECT imaging. In such a switchable SPECT/Pet dual head camera system, a mechanism and method is shown to perform transmission and emission scanning sessions with two line sources and two detectors wherein two sliding transmission detection windows are employed to differentiate between transmission and emission photons. Transmission and emission data can be collected simultaneously. This system provides that the dual transmission detection windows are each associated with a particular line source and move in synchronization. Further, the two line sources and the two detector windows all move in synchronization in the direction of the long axis of the object being scanned. In this configuration, the system can effectively reduce the amount of cross-talk detected by a detector.

36 Claims, 30 Drawing Sheets

335

| PEAK PMT ADDRESS | TYPE | ANALOG GLOBAL ENERGY DATA BUFFER ADDRESS / COUNT → | | | | | | | | | | | | | |
|---|---|---|---|---|---|---|---|---|---|---|---|---|---|---|---|
| | | 0 | 1 | 2 | 3 | 4 | 5 | 6 | 7 | 8 | 9 | 10 | 11 | 12 | 13 | ... | n |
| 0 | | | | | | | | | | | | | | | | |
| ... | | | | | | | | | | | | | | | | |
| 7 | NORMAL | 55 | 1 | 8 | 20 | 19 | 3 | 6 | 18 | STOP | | | | | | |
| ... | | | | | | | | | | | | | | | | |
| 38 | EDGE | 55 | 22 | 23 | 39 | 37 | STOP | | | | | | | | | |
| ... | | | | | | | | | | | | | | | | |
| 46 | CORNER | 55 | 41 | 42 | 43 | STOP | | | | | | | | | | |
| ... | | | | | | | | | | | | | | | | |
| 54 | | | | | | | | | | | | | | | | |

FIG. 8

CENTROID TYPE

345

| PMT ADDRESS | NORMAL | SHORT EDGE | LONG EDGE | CORNER | AUX TYPE 1 | AUX TYPE 2 |
|---|---|---|---|---|---|---|
| 0 | Wx / Wy | Wx / Wy | Wx / Wy | Wx / Wy | Wx / Wy | Wx / Wy |
| 1 | Wx / Wy | Wx / Wy | Wx / Wy | Wx / Wy | Wx / Wy | Wx / Wy |
| 2 | Wx / Wy | Wx / Wy | Wx / Wy | Wx / Wy | Wx / Wy | Wx / Wy |
| 3 | Wx / Wy | Wx / Wy | Wx / Wy | Wx / Wy | Wx / Wy | Wx / Wy |
| 4 | Wx / Wy | Wx / Wy | Wx / Wy | Wx / Wy | Wx / Wy | Wx / Wy |
| 5 | Wx / Wy | Wx / Wy | Wx / Wy | Wx / Wy | Wx / Wy | Wx / Wy |
| ⋮ | | | | | | |
| 54 | Wx / Wy | | Wx / Wy | Wx / Wy | Wx / Wy | Wx / Wy |

FIG. 9

MULTI-HEAD NUCLEAR MEDICINE CAMERA FOR DUAL SPECT AND PET IMAGING WITH MONUNIFORM ATTENUATION CORRECTION

BACKGROUND OF THE INVENTION (1) Field of the Invention

The present invention relates to the field of nuclear medicine systems. Specifically, the present invention relates to signal processing systems for scintillation detectors.

(2) Prior Art

Gamma cameras performing Single Photon Emission Computed Tomography (SPECT) have been utilized in nuclear medicine for some time. Anger proposed and developed such a system in the 1950s which has been modified and improved extensively with the introduction of high speed digital computer systems for image acquisition as well as image reproduction. However, SPECT camera systems utilize a collimator that is installed in front of the scintillation crystal within a scintillation detector. The collimator is used to collimate the incoming gamma rays so that only rays of a certain narrow angle of incidence actually penetrate the crystal. Although SPECT imaging is extensively used in nuclear medicine and provides beneficial image quality, the collimator introduces a source of image degradation in nuclear medicine images and tends to somewhat reduce the resolution and quality of images acquired by SPECT systems.

Cameras performing Positron Emission Tomography (PET) have been utilized in nuclear medicine as well with the introduction of relatively high speed detection electronics and computer systems for image acquisition and processing. These PET camera systems utilize a form of the scintillation detector that is used in SPECT systems, however, they do not utilize a collimator. In PET systems, the detection of two gamma rays in coincidence (in different scintillation detectors) is used to compute imaging information. A PET system employing two scintillation detectors is described in a paper presented by Gerd Muehllehner, M. P. Buchin, and J. H. Dudek entitled "Performance Parameters of a Positron Imaging Camera," published in the IEEE Transactions on Nuclear Science, Volume NS-23, No. 1, on February 1976 and also in a paper entitled "Performance Parameters of a Longitudinal Tomographic Positron Imaging System" by Paans, deGraaf, Welleweerd, Vaalburg and Woldring, in Nuclear Instruments and Methods, Volume 192, Nos 2, 3, on Feb. 1, 1982 pages 491–500. By utilizing higher energy gamma rays and eliminating the collimators, PET systems offer greatly improved image resolution and image quality over SPECT systems. Because the collimators are removed in PET systems, the detected count rate is higher in PET cameras over SPECT camera systems. Although both camera systems utilize different detection electronics and other circuitry, both PET and SPECT systems employ scintillation detectors.

The detection hardware for SPECT and PET systems is different in terms of the manner in which the systems detect and record events and is also different because PET systems operate at higher count rates over SPECT systems. Further, SPECT systems employ a different radionuclide over PET systems and detect gamma rays at different energy levels over PET systems. For this reason, although SPECT and PET systems are versatile and useful within nuclear medicine, in the prior art, different camera systems have been implemented and supplied for PET and SPECT imaging. Therefore, a facility desiring to perform SPECT and PET imaging is required to acquire two separate camera systems at a relatively greater expense.

It would be advantageous to provide a nuclear camera system offering the ability to perform both SPECT and PET imaging techniques within a single configurable system. Therefore, the expense of acquiring two separate systems can be advantageously avoided. The present invention offers such advantageous capabilities.

Moreover, non-uniform photon attenuation is an important factor that affects the quantitative accuracy of images collected using PET and SPECT camera systems and can decrease the sensitivity of these systems for lesion detection. Non-uniform photon attenuation creates image degradation by interfering with and partially absorbing the radiation emitted from an organ containing a radio-pharmaceutical. Photon attenuation within PET and SPECT systems tends to degrade images by also introducing image artifacts and other distortions that can result in false positive detection of lesions or the failure to detect lesions. The effects of photon attenuation are especially complex in cardiac studies as a result of nonuniform attenuation attributed to the thorax.

Transmission computed tomography (TCT) can be used as a method for generating a nonuniform attenuation correction distribution. In transmission scanning, the source of radiation is directed toward the associated scintillation detector through the object of interest or patient. The transmission image data is gathered using a known source (e.g., line, sheet, or flood) of radiation. If performed separately from the SPECT emission or PET study, the collection of the transmission data requires additional data acquisition time and the collection of the transmission and emission data is susceptible to misregistration effects due to patient (e.g., "object") movement between the data gathering sessions. It would be advantageous to provide attenuation correction within a dual head camera system switchable between SPECT and PET modes. The present invention provides such advantageous capability.

The transmission study may be performed simultaneously with a SPECT emission study. Among other advantages, simultaneous acquisition of both transmission and emission data (in SPECT) reduces the effects of misregistration. In the case of a gamma camera with a single scintillation detector, it is known to use a sliding window or "band" associated with the field of view of the scintillation detector to move in conjunction with the line source to aid in allowing the gamma camera to differentiate between detected transmission photons and emission photons. For example, reference is made to an article entitled, "A Scanning Line Source for Simultaneous Emission and Transmission Measurements in SPECT," by Patrick Tan, et al., published in the Volume 34, No 10, of the Journal of Nuclear Medicine, in October 1993. This reference discloses use of a single scanning line source with a single moving detection band.

However, this solution offered by Tan et al. does not adequately account for "side scatter" or "cross-talk" in emission studies involving two scintillation detectors (e.g., within dual head detector systems). Cross-talk in emission studies involves transmission photons scattering off of an object (e.g., cause by Compton scatter) being studied and improperly detected by a scintillation detector as emission photons. In a dual detector gamma camera, transmission photons emitted from a line source that is associated with a given detector may be improperly detected (e.g., after scatter) as proper emission photons by the other detector. This is the case because the scattered photon loses energy as a function of the scatter angle and changes energy level. Cross-talk may also occur from emission photons that scatter off the object. In dual head gamma cameras, the effects of cross-talk are dealt with by performing a post processing operation on the detected data. This post processing operation is time consuming and not entirely accurate. Therefore, it would be advantageous to eliminate the need for such post processing step by eliminating the detection of the cross-scattered photons.

The use of a single sliding detection window associated with a single gamma camera detector does little to prevent cross-talk in a dual detector system. What is needed is a system that is operable within a dual detector camera system that effectively eliminates the improper detection of emission photons due to cross-talk. The present invention offers such a system and solution.

In addition, there is a dual detector gamma camera system that employs tracking zoom regions (e.g., window regions) that are designed to track the motion of an object of interest during ECT motion. Within this system, the zoomed regions of the detector change as the detector rotates through (Emission Computed Tomography) motion about the object. Reference is made to U.S. Pat. No. 5,304,806, entitled, "Apparatus and Method for Automatic Tracking of a Zoomed Scan Area in a Medical Camera System," issued Apr. 19, 1994, and assigned to the assignee of the present invention, which discusses tracking zoom regions. The present invention provides for advantageous combination with the above system.

Accordingly, the present invention provides image data correction for nonuniform attenuation within a dual head camera system configurable between SPECT imaging and PET imaging modes of operation. It is another object of the present invention to provide such a system in a dual head system that eliminates cross-talk between the detectors during transmission and emission acquisition. It is another object of the present invention to provide such mechanisms and methods as described above that additionally allow effective use in conjunction with a tracking zoom region of a scintillation detector or tracking zoom regions of a pair of scintillation detectors. These and other objects of the invention not specifically recited above will become clear within discussions of the present invention herein.

SUMMARY OF THE INVENTION

A multi-head detector nuclear camera system automatically switchable (and optimized) to perform either SPECT imaging or PET imaging and performing attenuation correction for nonuniform attenuation is described. The camera system employs, in one embodiment, a multidetector configuration having dual head scintillation detectors but can be implemented with more than two detector heads. The detectors contain switchable triggering circuitry so that coincidence detection for PET imaging and non-coincidence detection for SPECT imaging is available and can be automatically selected. Using a variable integration technique with programmable integration interval, the event detection and acquisition circuitry of the camera system is switchable to detect events of different energy distribution and count rate which are optimized for PET and SPECT imaging. In one mode a relatively larger integration interval is selected for SPECT imaging and a relatively shorter integration interval is selected for PET mode imaging. The system also includes dual integrators on each scintillation detector channel for collecting more than one event per detector at a time for PET or SPECT mode. In PET or SPECT mode, the system also employs variable PMT cluster sizing having smaller cluster sizes for PET imaging and relatively larger cluster sizes for SPECT. In PET or SPECT mode, the system also employs variable centroid shape and zonal triggering. Utilizing the above programmable settings, the camera system can be automatically configured to operate in either SPECT of PET imaging modes.

When instructed to operate in SPECT mode, under computer control, the camera system automatically loads the longer integration interval into the detectors, programs a PMT address table to allow larger sized clusters to be generated, queues for installation of the collimators, and automatically sets the trigger detection mode to non-coincidence. When instructed to operate in PET mode, under computer control, the camera system automatically loads the shorter integration interval into the detectors, programs a PMT address table to only allow smaller sized clusters to be generated, queues for removal of the collimators, and automatically sets the trigger detection mode to coincidence detection. In SPECT mode, SPECT reconstruction procedures are applied and in PET mode, PET reconstruction procedures are applied.

A mechanism and method is performed within the above described SPECT/PET dual head camera system for performing transmission and emission scanning sessions with two line sources and two detectors wherein two sliding transmission detection windows are employed to differentiate between transmission and emission photons when imaging transmission and SPECT emission simultaneously. Transmission and SPECT emission data can be collected simultaneously. This system provides that the dual transmission detection windows are each associated with a particular line source and move in synchronization with the associated line source. Further, the two line sources and the two detector windows all move in synchronization in the direction of the long axis of the object being scanned and at any given position all are within a given spatial plane that is transverse to the long axis of the object. In this configuration, the system can effectively reduce the amount of cross-talk detected by a detector (e.g., cross-talk being scattered photon radiation detected by a given detector but not originating from the detector's associated line source). The configuration of this system also effectively operates in conjunction with systems employing tracking zoom regions across detector surfaces (e.g., used for cardiac studies). Using this combination, the SPECT/PET camera system can be configured to perform a PET scan (180°) and a transmission scan (90°) and the PET reconstruction can be corrected for non-uniform attenuation by the transmission scan. Similarly, the system can be configured for SPECT imaging with a transmission scan with the SPECT reconstruction similarly corrected for non uniform attenuation.

BRIEF DESCRIPTION OF THE DRAWINGS

FIG. 2A2 illustrates event detection/trigger generation circuitry used by the dual head camera system operating in PET or coincidence mode of operation.

FIG. 2A3 illustrates circuitry of the coincidence timing circuit utilized by the camera system of the present invention to provide switchable SPECT/PET triggering mechanisms for generation of valid event triggering signals.

FIG. 3 is an illustration of a weighted centroid computation for determining the spatial coordinates of an event used by the present invention.

FIG. 8 is a logical illustration of the programmable PMT address table circuit of the present invention Digital Event Processor.

FIG. 9 is an illustration of the x and y weight table circuit of the present invention Digital Event Processor.

FIG. 13B illustrates photopeak energy distributions for emission/transmission energy level photons.

DETAILED DESCRIPTION OF THE INVENTION

In the following detailed description of the present invention numerous specific details are set forth in order to provide a thorough understanding of the present invention. However, it will be obvious to one skilled in the art that the present invention may be practiced without these specific details. In other instances well known methods, procedures, components, and circuits have not been described in detail as not to unnecessarily obscure aspects of the present invention.

Some portions of the detailed descriptions which follow are presented in terms of algorithms and symbolic representations of operations on data bits within a computer memory. These algorithmic descriptions and representations are the means used by those skilled in the data processing arts to most effectively convey the substance of their work to others skilled in the art. Unless specifically stated otherwise as apparent from the following discussions, it is appreciated that throughout the present invention, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Figure 1A:
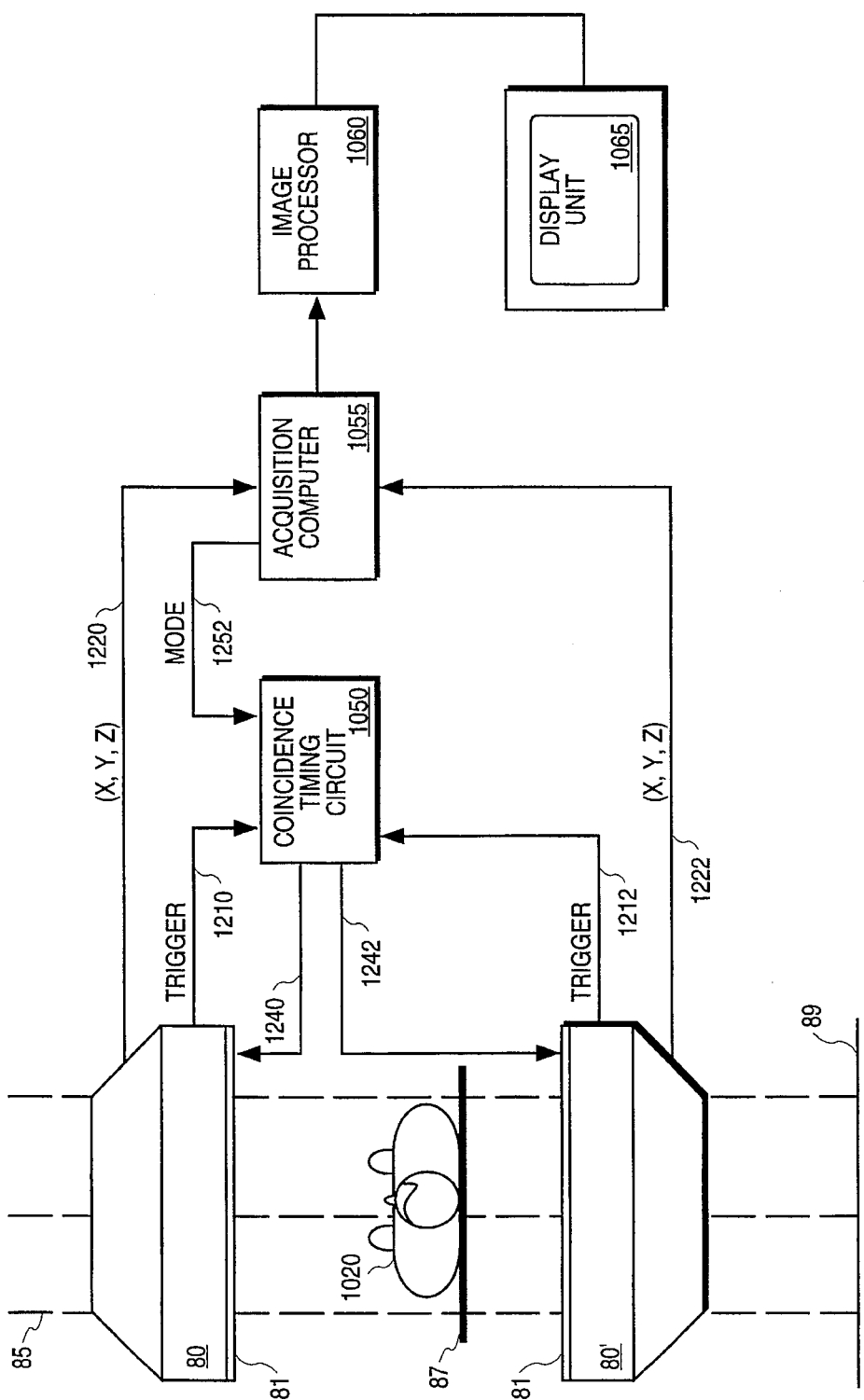
FIG. 1A illustrates a high level block diagram of a dual head gamma camera system employing both SPECT and PET operational modes, an acquisition computer and an image processor of the present invention.

The various embodiments of the present invention described herein are used in conjunction with a dual head scintillation detector camera system switchable between SPECT and PET imaging modes of operation and capable of performing nonuniform attenuation correction. It is appreciated that the present invention can advantageously operate within a camera system having more than two detector heads. With reference to FIG. 1A, a high level diagram of a dual head detector gamma camera system of the present invention is shown. Although an embodiment of the present invention is described with respect to a two detector camera system, it is appreciated that the teachings of the present invention can be extended to cover systems having more than two detectors (e.g., a triple head camera system is contemplated). Generally, the system of the present invention includes a pair of gamma camera detectors 80 and 80' ("dual head") composed of a plurality of photomultiplier tubes, PMTs, arranged in a two dimensional matrix and optically coupled to a glass plate to receive light (e.g., visible photons) from a crystal layer 81. The PMT array creates a photodetector. The crystal layer can be composed of sodium iodine, NaI, and is typically located between a collimator (not shown) and the PMT array. The collimator applied to each detector is used for SPECT imaging modes, but not for PET imaging modes, and is typically manufactured from a number of holes with lead septas arranged in a honeycomb convention to collimate gamma rays that strike the crystal 81. The detector pair are shown in a 180 degree configuration and can rotate with respect to each other such that they are at a 90 degree configuration.

Gamma rays that strike the NaI(Tl) crystal 81 cause well known scintillation events that release a number of visible light photons that are detected by the PMTs with different light intensities. Each PMT reports in the form of an analog signal indicative of the amount of light energy detected as a result of the scintillation event. In the present invention, these signals are digitized at an early circuit stage and are processed digitally. The gamma camera detectors 80 and 80' utilized within the scope of the present invention are of the Anger type and can be of a number of well known and commercially available designs and therefore some details of such a gamma detector will not be discussed in depth herein. However, as will be discussed, the present invention provides many enhancements in the image acquisition and processing of detected events so that the camera system can operate in either SPECT or PET image mode. An exemplary gamma camera detector used by one embodiment of the present invention can contain as many as 55 or 108 PMTs. A detector of the pair can also utilize smaller diameter PMTs along the edges to increase the detector's field of view. An embodiment of the present invention utilizes forty-nine 76 mm round PMTs and six 51 mm round PMTs for edge filling, however, the number of PMTs, their sizes and their configurations can be varied within the scope of the present invention.

It is appreciated that each detector, either 80 or 80', is similarly constructed and that discussions with respect to one detector are applicable to both.

The detector pair 80 and 80' of FIG. 1A are mounted on a gantry 85 which can rotate the detectors 80 and 80' in various orbits (ECT projections) around an object (patient) 1020 resting on table 87 (e.g., for ECT scanning operations). In either configuration (180 or 90 degrees), the detector pair can rotate about a center of rotation through a number of projection angles, as is known in gamma camera technology. The gantry 85 and table 87 rest on base 89. The detector pair 80 and 80' can also be directed transversely across the table 87 (e.g., for total body scanning operations) or placed over the patient 1020 for static imaging.

Upon an event detection in either detector 80 or 80', signals 1210 and 1212, respectively, carry initial event detection trigger pulses to a programmable coincidence timing circuit 1050 (CTC). The CTC unit 1050 then generates valid event trigger signals over lines 1240 and 1242, respectively, back to the detectors for the 80 and 80' depending on the mode of operation (either SPECT or PET). A signal carried over line 1252 indicates to the CTC unit 1050 the proper mode of operation (SPECT or PET). The valid event trigger signals 1240 and 1242 are used by the detectors to start (or reset) their accumulators (integrators) which accumulate (integrate) the energy of the detected scintillation and are therefore called "valid event" trigger signals. In the PET mode, integration is not started until a coincidence is detected between detector 80 and 80'. In SPECT mode, an integration is started for each detector upon a trigger event, regardless of coincidence. After integration and centroiding, the detectors 80 and 80' output an X, Y, and Z value over lines 1220 and 1222, respectively. These signals indicate the coordinate value (X,Y) ("localization") of the detected event with respect to the detector and its measured energy value, Z.

Within embodiments that utilize more than two detector heads, event detection information from each detector head is forwarded to the CTC unit 1050 that then detects coincidence between any two detectors feeding the CTC event detection information (when in PET imaging mode). In SPECT mode, each detector reports event information in non-coincidence in a similar fashion as the dual detector system.

Although the location of such hardware is not material to the present invention, hardware is included within each detector for digitizing the PMT channel signals, correcting these signals, and outputting X, Y, and Z values as will be discussed further below. To this extent, each detector 80 and 80' contains preamplification and digitization hardware as well as a Digital Event Processor. These are discussed further below. This hardware can be located within or outside the scintillation detectors 80 and 80'.

The values transmitted over bus 1220 and bus 1222 are input to an acquisition computer system 1055 which contains a general purpose digital computer system 1112 (FIG. 5) as described to follow. The acquisition computer 1055 of FIG. 1A stores the values for each detected event for each projection angle and this information is routed to an image processor 1060 which contains a standard user interface. The user interface provides a user input device for indicating which mode of operation (e.g. SPECT or PET) is requested. This device can also be located in computer 1055.

In the image processor 1060, events associated with various (Emission Computed Tomography) projection angles are stored in the memory of the computer system in order to generate image information and form count density information. This image information is collected in the form of a matricies for the different ECT projection angles. Image matrices are generally collected at different ECT angles and then a reconstruction is done, using tomographic reconstruction to generate a three-dimensional image ("reconstruction") of an organ.

Regarding SPECT and transmission acquisition, although the scintillation detectors are capable of reporting scintillation events with great accuracy, the computer system collects and interprets the data depending on reference matrix sizes (e.g., 64×64, 128×128, 512×512 and 1024×1024). These sizes are programmable. Further, a given matrix size can be allocated to certain portions of the field of view of the detector. For instance, in a cardiac study, a 512×512 matrix can be allocated to only the region of the detectors' field of view that covers the heart. Therefore, when data is received from the scintillation detector regarding the energy and location of a detected interaction, this information is "binned" (e.g., placed) into the appropriate matrix entry that corresponds to the location of the interaction as reported by the detector. Count information reported by the detectors is binned into memory 1102 and image data is taken from there. PET imaging is similar but generally makes use of higher resolution (e.g. smaller matrix cells).

The image processor 1060 also performs image reconstruction, nonuniform attenuation correction and uniformity correction based on the acquired event data for SPECT and PET imaging modes. The image processor 1060 is also coupled to a display unit 1065 (which can include a hardcopy device) for visualizing images captured by the camera system.

NONUNIFORM ATTENUATION CORRECTION SYSTEM

Embodiments of the present invention utilize a dual head camera system switchable between SPECT and PET imaging and utilize nonuniform attenuation correction and therefore include the collection, generation and usage of nonuniform attenuation correction factors used to improve gamma camera imaging. Since each patient that is imaged by a nuclear medicine gamma camera is different (e.g., differently shaped with different sizes, etc.) the tissue and bone structure that surround an organ of interest is different for each patient. This surrounding tissue and bone structure attenuates the radiation emitted from a radiopharmaceutical distributed within the imaged organ. The attenuation of the radiation is nonuniform because the attenuation coefficients of the different tissues and bone are different. Radiation attenuation non-uniformly reduces the count density in the image. This attenuation can lead to falsely identifying an artifact when in fact healthy tissue is imaged and vice-versa. If an artifact is improperly diagnosed as a lesion, this can lead to invasive measures which are painful and potentially dangerous (e.g., involves a health risk) for the patient.

Nonuniform attenuation caused by the body can be compensated for if the attenuation map of the body is known. Transmission scanning allows the gamma camera and the processing computer system to generate a nonuniform attenuation map of a particular object. This nonuniform attenuation map can be obtained for each ECT rotation angle of the scintillation detectors so that a reconstruction procedure can use the attenuation map for each angle. Generally, during transmission scanning, a source of known radiation is emitted through the patent to be scanned and then the radiation is detected by a scintillation detector. By measuring the intensity of the radiation emitted from the source, and by measuring the intensity of radiation emitted through the object at different ECT angles, the gamma camera's computer system can determine the extent of nonuniform radiation attenuation over different parts of the body. From this, a nonuniform attenuation correction map of the body can be determined using well known methods and procedures. The nonuniform attenuation correction map is used to correct emission image data collected during SPECT or PET emission studies.

TRANSMISSION COMPONENTS OF CAMERA SYSTEM

Figure 1B:
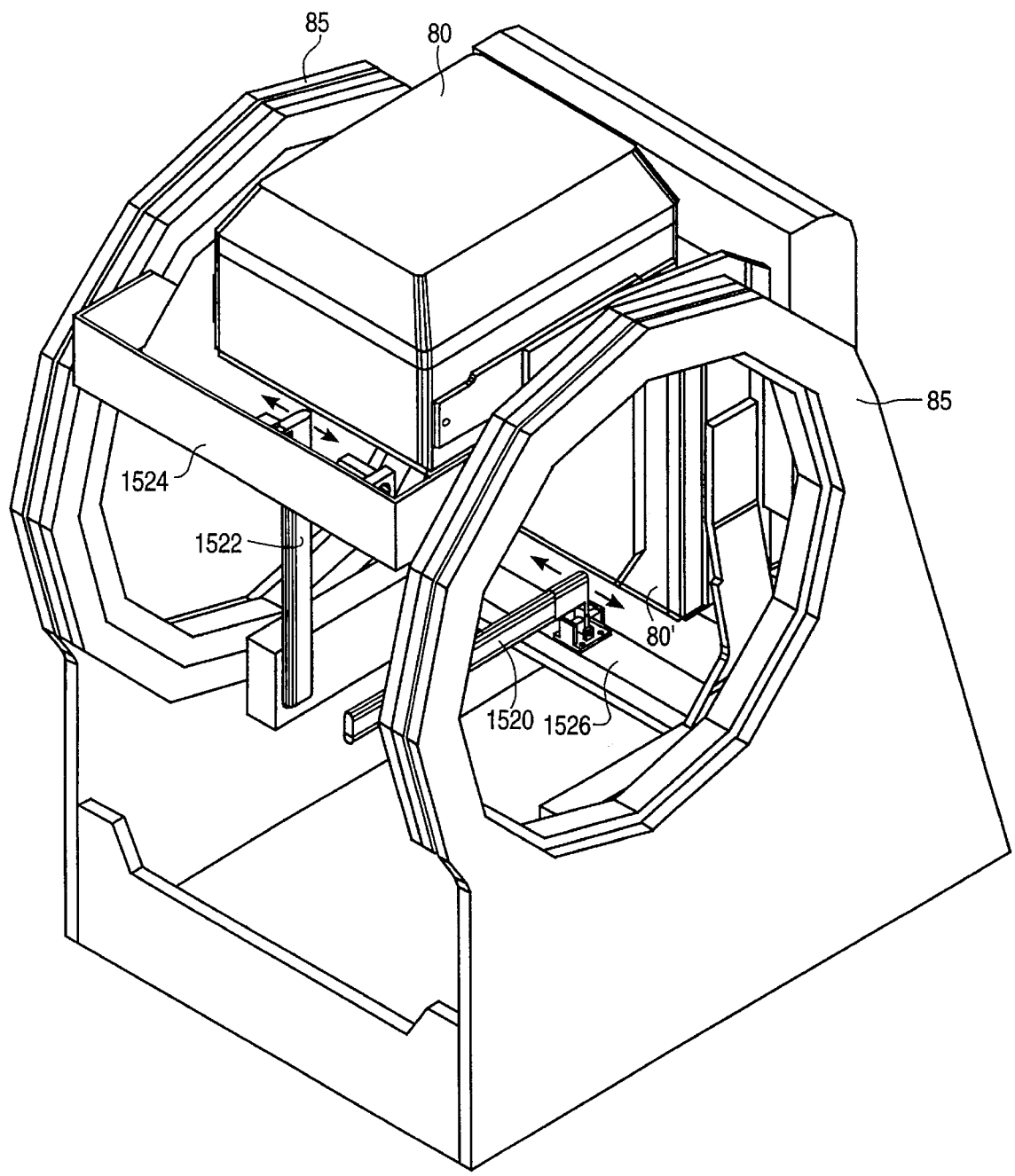
FIG. 1B is an illustration of the dual head detector system of the present invention with the line source assemblies configured for scanning and the detectors at 90 degrees configuration.

The dual head SPECT/PET detector system employing transmission components of an embodiment of the present invention is illustrated in FIG. 1B. Regarding the dual head implementation, two scintillation detectors 80 and 80' are installed within the gantry rings 85 and are rotatable about the center of the gantry ring 85. As shown in FIG. 1B, the detectors are at a 90 degree angle with respect to each other.

A table (not shown) is placed into the gantry ring 85 and patient 1020 rests on top of the table for imaging.

The detector pair can collect and report radiation that is emitted from a patient (e.g., emission image data for SPECT and PET imaging) and can also collect and report radiation emitted from a line source during transmission data acquisition. Transmission data is utilized, among other things, for generation of nonuniform attenuation correction distributions or "maps" to compensate emission data image for nonuniform attenuation attributable to the patient (e.g., the chest region in cardiac studies).

For transmission imaging, a separate radiation emitting line source (with collimator) is mounted and associated with each scintillation detector. For instance, line source assembly 1522 is associated with detector 80' and line source assembly 1520 is associated with detector 80. Also, line source assembly 1522 is mounted on rail 1524 and the base of line source assembly 1522 can move along the long axis of rail 1524, as shown in order to displace ("scan") across the field of view of the associated detector. Likewise, line source assembly 1520 is mounted on rail 1526 and the base of line source assembly 1520 can move along the long axis of rail 1526, as shown in order to displace ("scan") across the field of view of the associated detector. It is appreciated that when the detectors rotate about the center of gantry ring 85, the associated emission line source will rotate in like form and degree. Different types of line sources can be utilized within the scope of this embodiment of the present invention, including a Tc-99m filled line source or a line source using Gd-153, Am241, or Co-57. The line sources are utilized by the present invention for irradiating a patient in order to gather transmission data for the generation of the nonuniform attenuation correction map that is stored in memory for the patient.

Figure 1C:
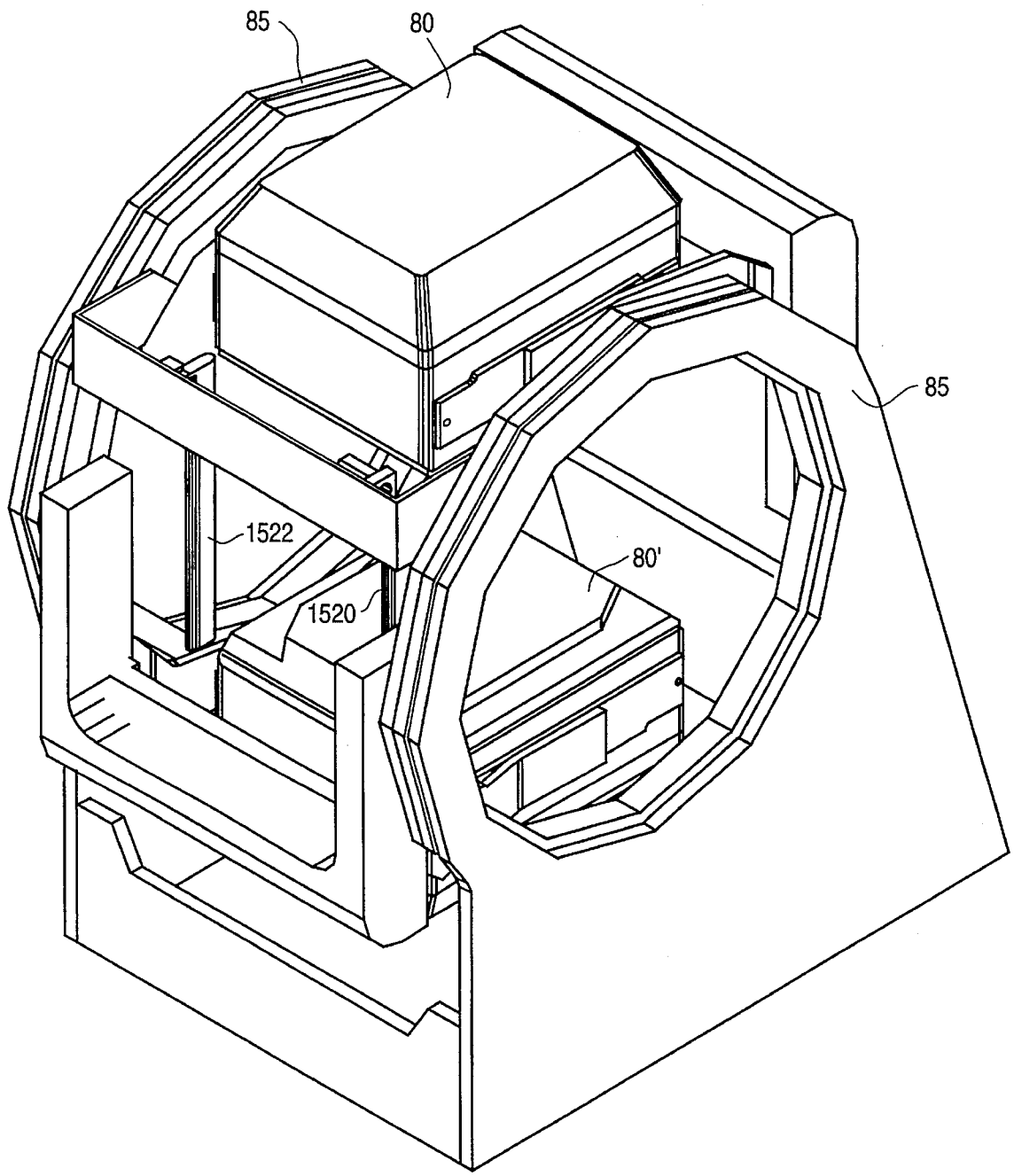
FIG. 1C illustrates the dual head detector system of the present invention with the line source assemblies withdrawn for storage and the detectors at 180 degrees configuration.

The scintillation detectors 80 and 80' can rotate about the gantry 85 so such that they are in the positions (180 degree orientation) shown in FIG. 1C. FIG. 1C also illustrates the line source assemblies 1522 and 1520 in their storage positions. The transmission imaging elements of the present invention will be discussed further below.

DETECTOR ELECTRONICS

The circuitry and logic of each detector 80 and 80' for signal processing is further illustrated within the following figures: FIG. 2A1, FIG. 2A2, FIG. 2B, FIG. 2C and FIG. 2D. It is appreciated that this circuitry can alternatively be located outside the detector heads 80 and 80' or partially spread inside and partially outside of the detector heads 80 and 80'. An embodiment of the present invention can also be implemented utilizing discrete electronic components in lieu of a general purpose computer system.

TRIGGER DETECTION AND SWITCHABLE PET AND SPECT EVENT RECOGNITION

Since the present invention system is switchable between SPECT and PET imaging, the system employs two separate trigger mechanisms for recognizing a valid event and generating a valid event trigger signal. There are at least two differences between these trigger mechanisms for the SPECT and PET imaging systems. Generally, the first difference is that the actual trigger detection circuitry is different for SPECT and PET modes of operation because the time between valid events from the two detectors needs to be known with high accuracy in PET. The SPECT mode utilizes a leading edge discriminator in its event detection circuitry while the PET mode utilize a constant fraction discriminator in its event detection circuitry. Secondly, the PET mode utilizes a coincidence circuit to determine a valid event from a detected event while the SPECT mode does not. These differences will be explained below.

Figure 2A:
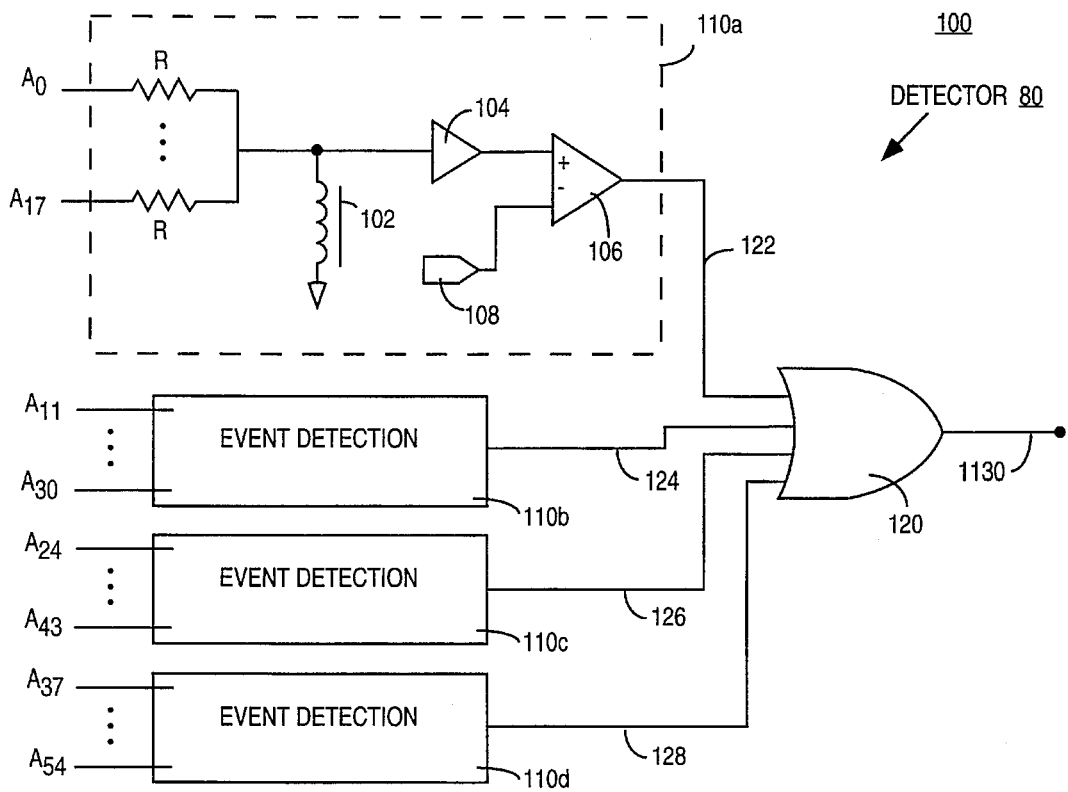
FIG. 2A1 illustrates event detection/trigger generation circuitry used by the dual head camera system of the present invention operating in SPECT mode of operation.
Figure 1:
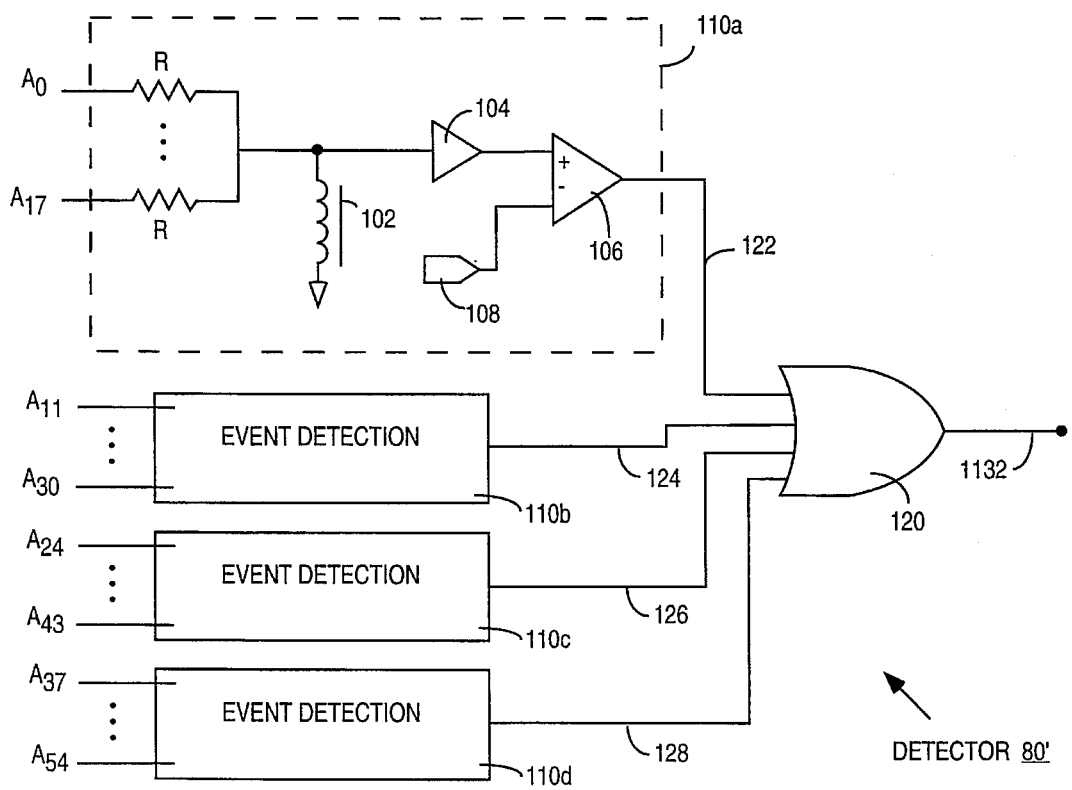

FIG. 2A1 illustrates detection logic 100 for detector 80 utilized in the SPECT mode. A duplicate circuit of 100 (lower) is used for detector 80' for SPECT mode. In a system having more than two detector heads, logic 100 is duplicated for each detector head. The outputs 1130 and 1132 from these two circuits belong to buses 1210 and 1212, respectively, and are forwarded to the CTC unit 1050 (see FIG. 1). Regarding FIG. 2A1, the trigger signal generation circuit 100 is duplicated for each detector as shown. Therefore, discussions regarding the operation of circuit 100 with respect to detector 80 are applicable to the duplicate circuit for detector 80' of the present invention. According to the arrangement of the PMTs in the detector, the output of each PMT associated with a particular spatial quadrant (or "zone") of the detector matrix is sent to one of four trigger detection circuits 110a, 110b, 110c or 110d. Each zone represents a separate spatial portion of the scintillation detector. The zones can be divided horizontally across the imaging surface, vertically, or both. Although the precise alignment of each PMT in each zone is not critical to the present invention, the zones can be overlapping. The PMT signals shown A0–A54 are voltage signals. The signals of the first zone, A0 . . . A17 are sent to trigger circuit ("event detection") 110a where each is coupled to a delay line 102 and an amplifier 104 which together create a 200 ns clip circuit. The trigger pulse received from the PMT circuits is roughly a 200 ns analog pulse. An event occurring within a particular zone will cause an event detection circuit of the corresponding zone to generate an output signal or "event or scintillation indication." In systems having more than two detectors, the above event detection circuitry is located in each detector.

For the SPECT mode of operation, the clipped signal from circuit 104 is coupled to the positive end of a discriminator circuit 106 and a computer controlled reference input is coupled to a threshold input circuit 108. The reference signal at 108 is coupled to receive the output of a computer controlled DAC (not shown). Therefore, only trigger signals over the threshold voltage are allowed to pass through circuit 106 and they are clipped to 200 ns. The output of the comparator 106 is then coupled to the input of OR gate 120 via line 122. Line 130 will assert a triggering pulse when ever a PMT of the designated zone detects an event. This circuitry is replicated for each of the other four zones of the detector PMT matrix for detector 80 (e.g., signals A11 . . . A30 feed circuit 110b which generates a trigger over line 124, signals A24 . . . A43 feed circuit 110c which generates a trigger over line 126, and signals A37 . . . A54 feed circuit 110d which generates a trigger over 128). The same is true for detector 80'. It is appreciated that additional or fewer event detection circuits (e.g., for more or fewer zones) can be used within the scope of the present invention. Multiple trigger channels (zonal triggering) are used to maintain low dead time at high counting rates. The trigger channels are overlapped, as discussed above, to prevent sensitivity loss at the zone boundaries and to achieve low deadtime at high count rates.

Trigger lines 122, 124, 126, and 128 of FIG. 2A1 are coupled to the input of OR gate 120. Therefore, when an event is detected by the camera detector 80, OR gate 120 of trigger circuit 110 of the present invention will generate a trigger pulse over line 1130. These triggering pulses are used, along with other signals, to generate Start(t0) and Start(t1) and (after going through CTC circuit 1050) are used by the integration circuits 280(0)–280(54) (FIG. 2C) of the present invention to start integration of the PMT signals for the detected gamma event. When an event is detected by the camera detector 80', duplicate OR gate 120 of the duplicate trigger circuit for detector 80' of the present invention will generate a trigger pulse over line 1132. Lines 1132 (for detector 80') and 1130 (for detector 80) are within buses 1212 and 1210, respectively (see FIG. 1).

Figure 2A:
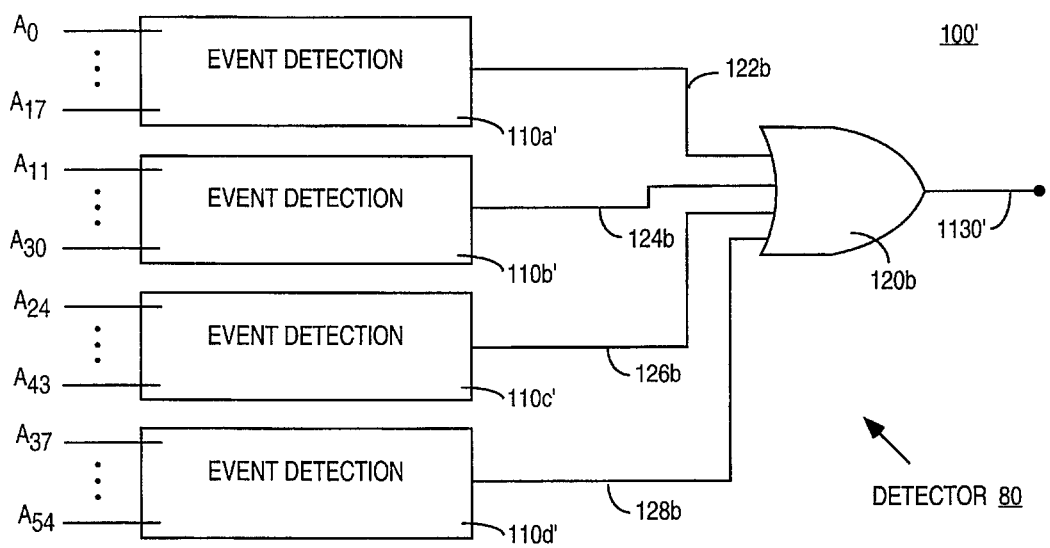
Figure 2:
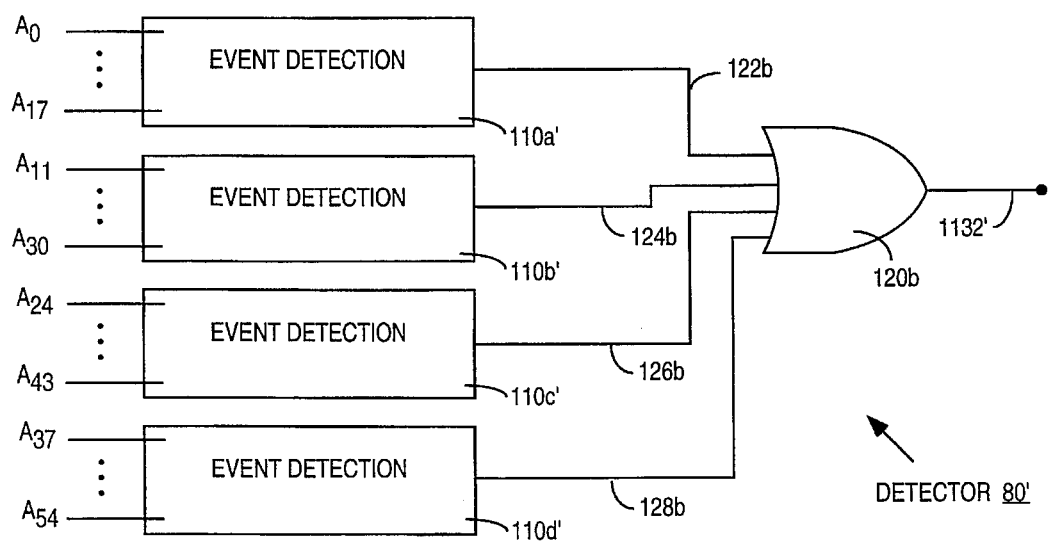

Event detection for the PET imaging mode comprises different electronics which are illustrated in FIG. 2A2. Circuit 100' is associated with detector 80 and a duplicate circuit (lower) is associated with detector 80'. In a system having more than two detector heads, logic 100' is duplicated for each detector head. Unless discussed as different, circuit 100' (used for PET) is analogous to circuit 100 (used for SPECT). The outputs 1130' and 1132' from these PET circuits 100' belong to buses 1210 and 1212, respectively, and are forwarded to the CTC unit 1050 (see FIG. 1). The event detection logic 110a'–100d' for each detector zone utilizes a constant fraction discriminator when in PET mode in lieu of the leading edge discriminator for SPECT imaging used in circuit 100. This is done to maintain timing accuracy in PET imaging. An event occurring within a particular zone will cause an event detection circuit (110a'–110d') of the corresponding zone to generate an output signal or "event indication." The output of the event detection circuits 110a'–100d' are clipped to one-half the width of the desired coincidence timing window. For each detector, the outputs of the event detection circuitry are forwarded to an OR gates 120b. The outputs 1130' and 1132' of these gates are forwarded over buses 1210 and 1212, respectively. It is appreciated that pipelining of the preamplification/digitizer circuits (as will be discussed below) allows a 240 ns "memory" therefore allowing capture of the entire pulse that generated the detected coincidence pulse in PET imaging mode.

Figures 2, 2A, 3:
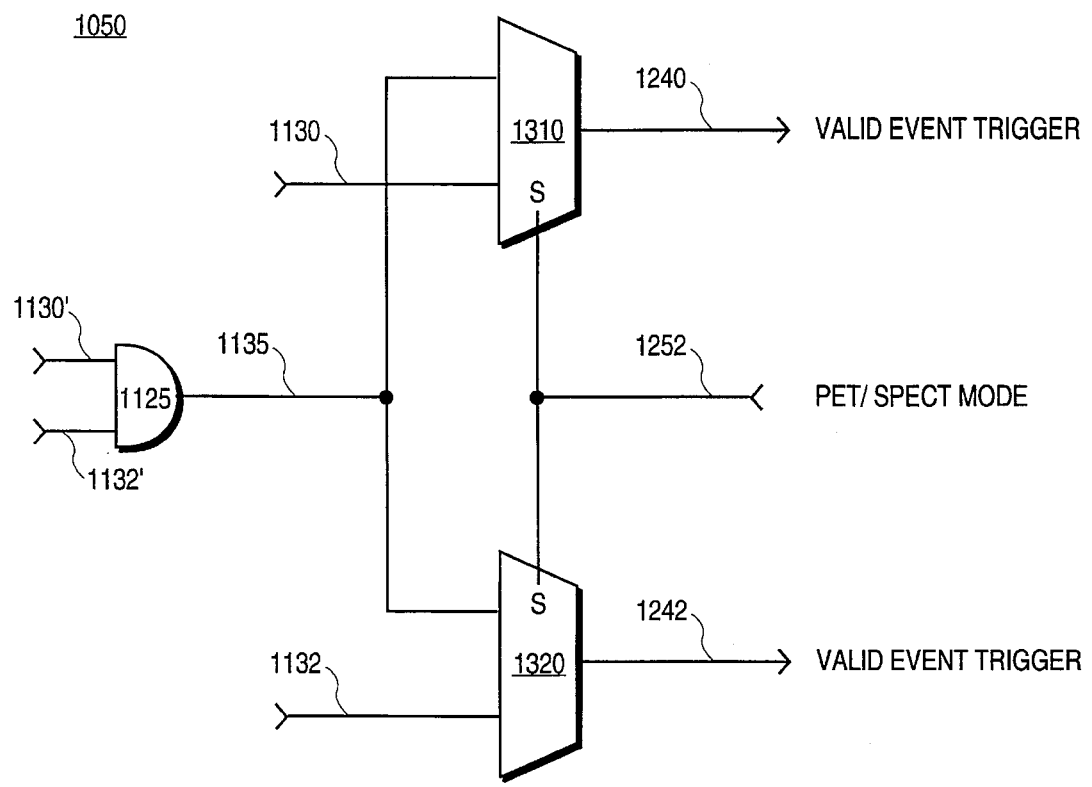

FIG. 2A3 illustrates the logic of the CTC unit 1050 (as shown in FIG. 1). Bus 1210 carries signals 1130 and 1130' while bus 1212 carries signals 1132 and 1132'. Signals 1130' and 1132' are input to AND gate 1125 which generates a signal over line 1135 only if signals 1130' and 1132' are in coincidence (e.g., within a 10–15 ns window). Signal 1135 is coupled to multiplexer 1310 and to multiplexer 1320. Signal line 1130 is coupled to multiplexer 1310 while signal 1132 is coupled to multiplexer 1320. A control (or select) signal 1252 is coupled to the select inputs of multiplexers 1310 and 1320. When the control signal 1252 selects PET imaging operation mode, then the signal over line 1135 passes over both line 1240 to detector 80 and to line 1242 to detector 80'. These are the valid event trigger signals. When the control signal 1252 selects SPECT mode, then the signal over line 1130 is carried over line 1240 to detector 80 and the signal over line 1132 is carried over line 1242 to detector 80'. These are the valid event trigger signals. It is appreciated that the signals over line 1240 are used to trigger the integrators associated with the preamplification and digitization circuitry for detector 80 while the signals over line 1242 are used to trigger the integrators associated with the preamplification and digitization circuitry for detector 80'. The signals carried over line 1240 and 1242 represent "valid" event detection. The multiplexers 1310 and 1320 allow a switchable mode of operation between event detection for SPECT and PET imaging modes under the present invention including a coincidence detection mode (line 1135) and a non-coincidence detection mode (lines 1130 and 1132).

For detector 80, the valid event trigger signal 1240 is used as trigger signal 130 to convey start (t0) and start (t1) while for detector 80' the valid event trigger signal 1242 is used as trigger signal 130.

In a system having more than two detector heads, in SPECT mode, the event indication signals from each detector are routed back to their associated detector as the valid event trigger. In PET mode, a series of AND gates are coupled so that each possible combination of two detector is represented by an AND gate and, in such way, a coincidence between any two detectors of the system can be determined. Once a coincidence is detected, a valid event trigger is forwarded back to the two detectors in coincidence.

ANALOG SUM OF GLOBAL ENERGY

Figure 2B:
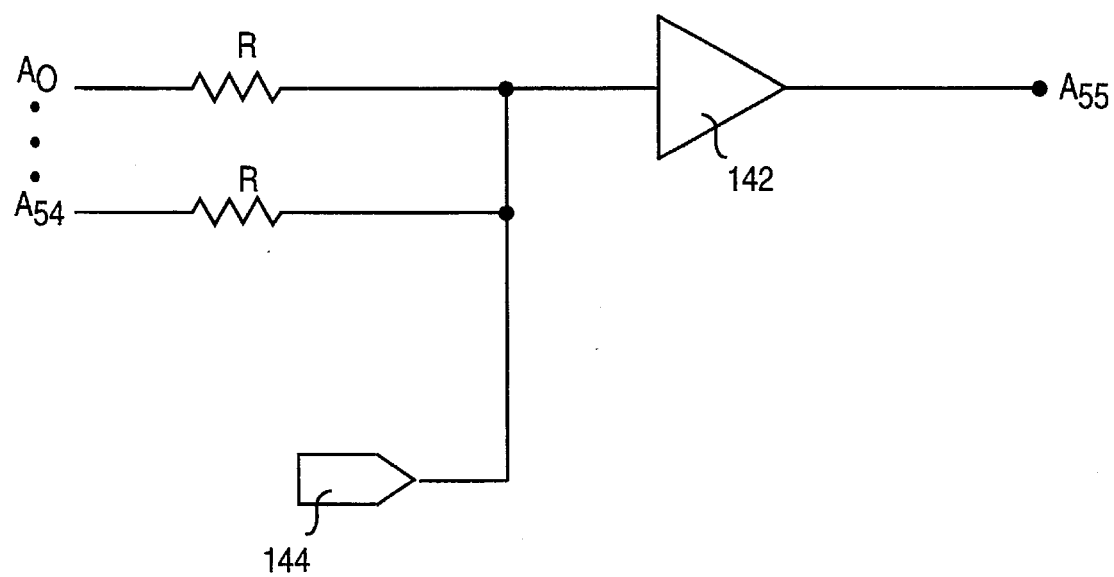
FIG. 2B is a circuit diagram of the circuitry utilized by the present invention for generating an analog total ("global") energy signal.
Figure 2C:
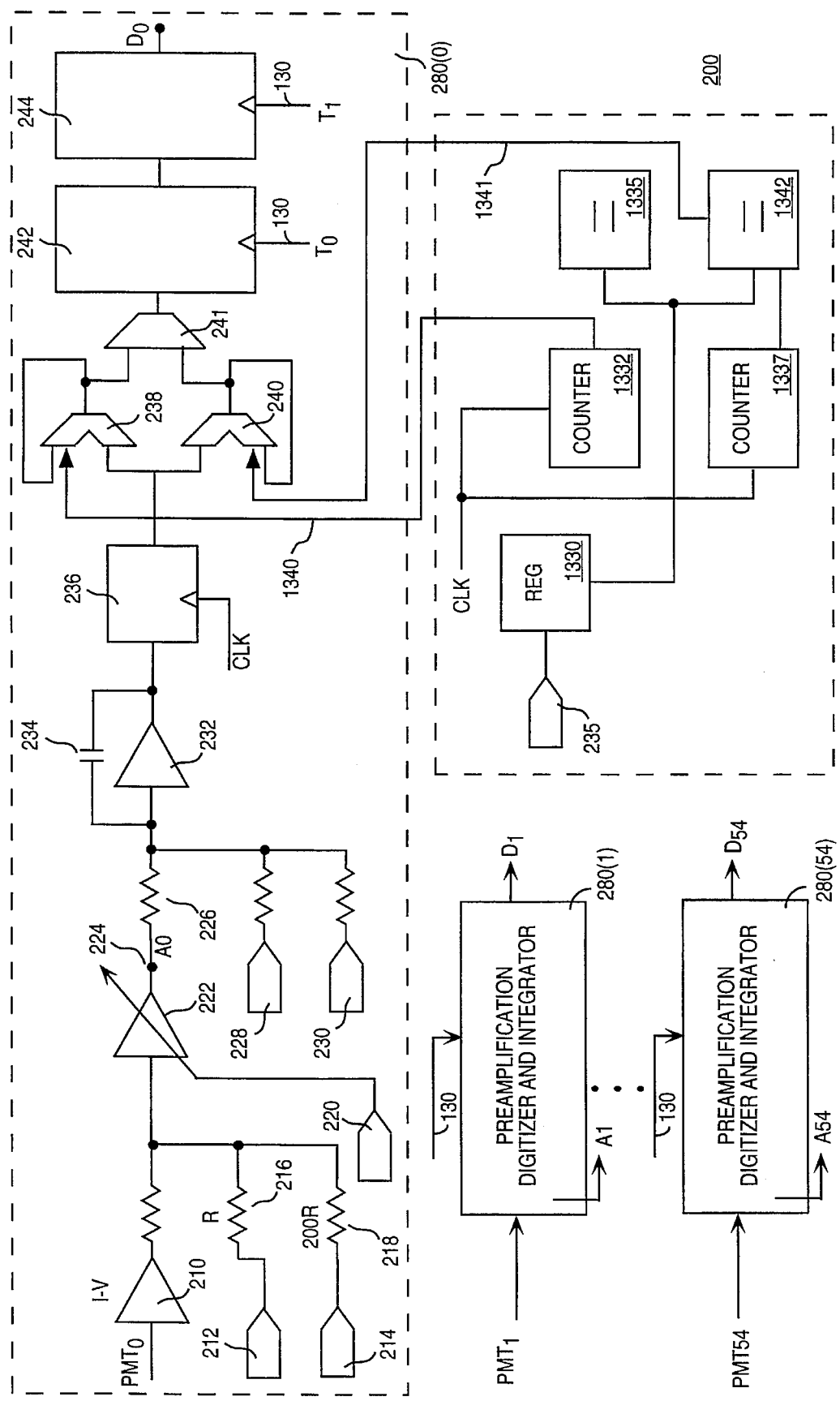
FIG. 2C illustrates the preamplification/digitizer circuitry of the present invention (utilizing dual integrators per channel) for providing a compensated digital response signal that is digitally integrated for each PMT of the gamma detector and allowing programmable integration intervals for PET/SPECT imaging modes of operation.

FIG. 2B illustrates an analog summing circuit utilized by one embodiment of the present invention. This circuit is included in detector 80 and a separate circuit in detector 80'. The voltage signals A0 ... A54 from each PMT channel (e.g., signal from each PMT) are summed together and output by amplifier 142. An offset voltage is fed into the summing circuit via input 144. The offset voltage is controlled by a computer controlled DAC. The output, or total energy of the gamma event, is generated over line A55. This output represents the analog sum of all of the voltage signals from each PMT channel plus an adjustable offset from circuit 144. The analog signal over A55 is called the analog global energy signal. This global energy signal may be supplied to an available channel (e.g., channel 55) for preamplification, digitization and integration by circuit 200 (FIG. 2C). The Digital Event Processor of each detector the present invention receives signal A55 of its corresponding detector. As will be discussed to follow, the global energy value is also computed digitally by summing the digitized integrated channel signals of the PMTs. Either of these methods can be utilized within the scope of the present invention.

PREAMPLIFICATION DIGITIZER

Refer to FIG. 2C which illustrates the preamplification digitizer circuits 200 of the present invention for each of the 55 channels (plus one for A55) for detector 80. A duplicate of this circuit is used with the channels of detector 80'. In a system having more than two detectors, circuit 200 is duplicated for each detector head. Circuit 200 is used for both SPECT and PET imaging mode and utilizes switchable circuitry to optimize between modes. These circuits perform the preamplification, digitization, and integration for each analog voltage signal for a PMT channel. The output of circuit 200 is fed to a Digital Event Processor for detector 80. A duplicate preamplification digitizer circuit 200 is used for detector 80' and outputs to a duplicate Digital Event Processor of detector 80'. As will be discussed, each preamplification digitizer circuit for each channel contains two separate integrator circuits. Unless discussed otherwise, circuit 200 for detector 80 is analogous in operation and structure to its duplicate circuit of detector 80'. Circuit 280(0) corresponds to the current (amps) output signal received directly from PMT 440 (e.g., channel 0) and this circuit 280(0) is separately replicated for each of the 55 PMT channels of the present invention and, as shown, circuits 280(0) to 280(54) operate to simultaneously process the current output signals for PMT0 to PMT54. Regarding circuit 280(0), the current signal output of PMT0 is fed into a current to voltage converter 2 10 and the output of this signal is fed through a resistor to a voltage gain amplifier 222.

A computer controlled digital to analog converter (DAC) outputs two adjustment signals over line 212 and 214 for baseline voltage correction. The signal over line 212 is fed through a resistor 216 for coarse adjustment and line 214 is fed through resistor 218, which has much larger resistance (e.g., on the order of 200×) than resistor 216, for fine adjustment. The signals received via lines 212 and 214 provide a baseline offset voltage adjustment to the output signal received from the PMT0. A computer controlled digital to analog converter (DAC) outputs a voltage adjustment signal to circuit 220 to control the gain of amplifier 222 having an exemplary gain adjustment of 10:1. The analog gain adjustments are coarse adjustment with fine gain adjustments performed by the calibration table, see FIG. 2D as discussed to follow. The baseline offset adjusted signal and the gain adjusted signal is then output at point 224 as signal A0 for each channel. Similarly, for each PMT channel, the above circuitry is replicated for generating signals A1 to A54. The trigger signal 130 is uniformly supplied to each of the circuits 280(0) to 280(54) so that each channel is triggered coincidentally.

The output of gain amplifier 222 is then fed into resistor 226. The voltage input 228 and voltage input 230 are coupled through respective resistors to the output of resistor 226. The output of resistor 226 is then fed into amplifier 232 and capacitor 234 in series. The outputs of the amplifier 232 and capacitor 234 are then coupled to the input of the analog to digital converter (ADC) 236. The above circuit (e.g., from point 224 to the input of ADC 236) is utilized for pulse insertion used for diagnostic purposes that are not particularly pertinent to the present invention. Pulses can be artificially inserted via inputs 228 and 230.

Referring to FIG. 2C, the ADC 236 converts the analog signal A0 to digital samples based on the frequency of clock input as shown. One embodiment of the present invention utilizes a sample frequency of 20 to 25 MHz as a sample clock. The output of ADC 236 is then fed to the input of two adders ("integrators" or "accumulators") 238 and 240 coupled in an integration configuration. The present invention utilizes dual digital integrators for each PMT channel in order to more effectively process conditions wherein two gamma events are detected in close temporal proximity. Each integrator 238 and 240 (of each channel 0–54) contains a separate register (accumulator) for containing the current sum value and performs piecewise linear integration with a clip binary value at 1023 (e.g., no rollover is allowed). The outputs of both integrators are coupled to multiplexer 241. The multiplexer 241 selects between one of the two integrator registers (accumulators) for output to the latch circuits 242 and 244. Latch circuits 242 and 244 comprise a two stage FIFO arrangement. The trigger pulses Start(t0) and Start(t1) received over 130 are used to reset the integrators. These trigger pulses arrive over line 1240 for detector 80 and over line 1242 for detector 80'. At the end of a programmable integration (accumulation) period, the value of the integration process for either integrator is then stored within a two stage latch circuit of 242 or 244. The output of the latch circuit 242 or 244 is the digitized value of the signal generated by PMT0 for a given event and this value is designated as D0. The digitized signal D0 is supplied to the Digital Event Processor 300. The above is explained in more detail with reference to FIG. 6B.

Under computer control, the duration of the integration interval for all integrators is programmable over bus 235 which is coupled to a computer processor. The programmed period (having a resolution of the sampling clock frequency of 20–25 MHz) is loaded into register 1330 over line 235.

Upon a valid event detection signal (over line 1240) that resets integrator 238, a corresponding counter 1332 is also reset. Counter 1332 is coupled to the sampling rate clock. The output of the counter 1332 is coupled to a comparator 1335 which also receives an output from register 1330 which contains the programmable integration (accumulation) period. Upon a coincidence, an output signal is carried over line 1340 which signals the completion of the integration period for integrator 238. Upon a valid event detection signal (over line 1240) that resets integrator 240, a corresponding counter 1337 is also reset. Counter 1337 is coupled to the sampling rate clock. The output of the counter 1337 is coupled to a comparator 1342 which also receives an output from register 1330 which contains the programmable integration (accumulation) period. Upon a coincidence, an output signal is carried over line 1341 which signals the completion of the integration period for integrator 240. It is appreciated that like the integrator circuits 238 and 240, the counters 1332 and 1337 are not effected by the trigger pulse unless they are idle at the time the valid event trigger pulse is received.

It is appreciated that register 1330, counters 1332 and 1337, and comparators 1335 and 342 are coupled to each channel circuitry 280(0)–280(54) and the connections shown with respect to channel circuitry 280(0) are exemplary of the connections made for each other channel. In other words, only one register 1330 is utilized to contain the integration interval associated with all channel integrators for a given detector. Specifically, the output of comparators 1335 and 1342 are coupled to the accumulators 238 and 340 of all channel circuitry 280(0)–280(54) in the fashion shown in FIG. 2C with respect to channel circuit 280(0).

The integration (accumulation) period programmed into register 1330 is programmable with a resolution of 20–25 MHz in one embodiment of the present invention. During PET imaging, the accumulation period is set to approximately 320 ns per event due to the high count rate received during PET imaging and the high energy distribution of gamma events that are detected (511 K electron-volts) in PET imaging. During SPECT operational modes, the accumulation period is set to approximately 840 ns as a result of the lower count rate detected and the lower energy distribution of gamma events detected. Therefore, using the above circuitry, the present invention provides a programmable mechanism for optimizing the preamplification/digitizer circuits for either PET or SPECT modes and this mechanism is switchable. It is appreciated that a duplicate circuit 200 is included for detector 80' but its valid event trigger signals (e.g., 130) arrive over line 1242 instead of line 1240. The program signal 235 is coupled to both circuits 200 such that both detectors 80 and 80' are simultaneously configured for PET or SPECT mode of operation.

Using the dual integrators of FIG. 2C of the present invention, either one or both of the accumulators of 238 or 240 can be enabled to integrate an incoming signal from the output of ADC 236. The two integration results are multiplexed onto a common data path and either result can be selected and stored in the two stage latch circuit. Each integrator can be separately triggered by valid event trigger start(t0) and start(t1). In operation, when a trigger signal occurs, if either integrator is available (e.g., not integrating and not holding an integrated result) then that accumulator is reset and enabled to begin integrating the event. When either of the accumulators completes, the integrated value is transferred to the first FIFO stage (e.g., latch 242) assuming this stage is available. If it is not available, the accumulator holds the value. Integration continues for a predetermined period of time after the trigger signal until a sufficient amount of the gamma event's energy is integrated. Values are transferred from FIFO stage 1 (latch 242) to FIFO stage 2 (e.g., latch 244) as FIFO stage 2 becomes available (e.g., transfer its value). When data is written to FIFO stage 2, the present invention signals that data is ready to be transferred to an associated Digital Event Processor (DEP) 300, see FIG. 2D. Each detector 80 and 80' contains its own DEP circuit 300.

Referring to FIG. 2C, the dual accumulator design of the present invention provides an implicit mechanism for handling event pile-up where two events interact during the same time period. Since the present invention computes positions based on local PMT clusters, pile-up events which occur in different regions of the detector can be properly positioned and such are called temporal pile-ups. If the two events that are involved in a temporal pile-up happen to be separated by more than the trigger channel deadtime, then both accumulators will be enabled and both events will be fully integrated. Accuracy of positions will be impacted by the spatial distance separating the temporal events. The greater the separation, the lower the impact. This is discussed in more depth below.

Within circuit 200, the circuit 280(0) is replicated for each channel as shown in FIG. 2C. The output current signals from PMT#1 through PMT#54 are fed into circuits 280(1) through 280(54). The digital data signals D0 to D54 are output from circuits 280(0) through 280(54), respectively. Each of the 55 preamplification digitizer circuits 280(0)–280(54) are coupled to receive valid event trigger signals start(t0) and start(t1) from line 130. It is appreciated that an extra channel (e.g., a preamplification digitizer circuit 280(55)) can be added in order to process the analog global energy signal from A55 (see FIG. 2B). In this embodiment, the output D55 would correspond to the amplified, digitized and integrated value for all channels (e.g., the digitized value of the analog global energy of the event). In such an embodiment, the value D55 would be output to the DEP 300 (as will be discussed to follow) with an appropriate PMT address value indicating the data as analog global energy data.

The preamplification circuits of FIG. 2C can be directly adjusted using gain (e.g., line 220) and baseline offset (e.g., lines 212 and 214) adjustments. The above adjustment lines are referred to as control link signals which are coupled to computer controlled addressable DACs. The amount of nominal baseline and the amount of variation associated with levels of adjustment can be used to determine the accuracy of a given channel.

At the completion of the programmed integration interval, when latch 244 data is present, then all of the digital data stored in each second stage latch for each channel is transferred to the appropriate DEP 300 (FIG. 2D) over bus 307. This is called a data "transfer" to the DEP 300 and occurs for both detectors 80 and 80'.

DIGITAL EVENT PROCESSOR

Figure 2D:
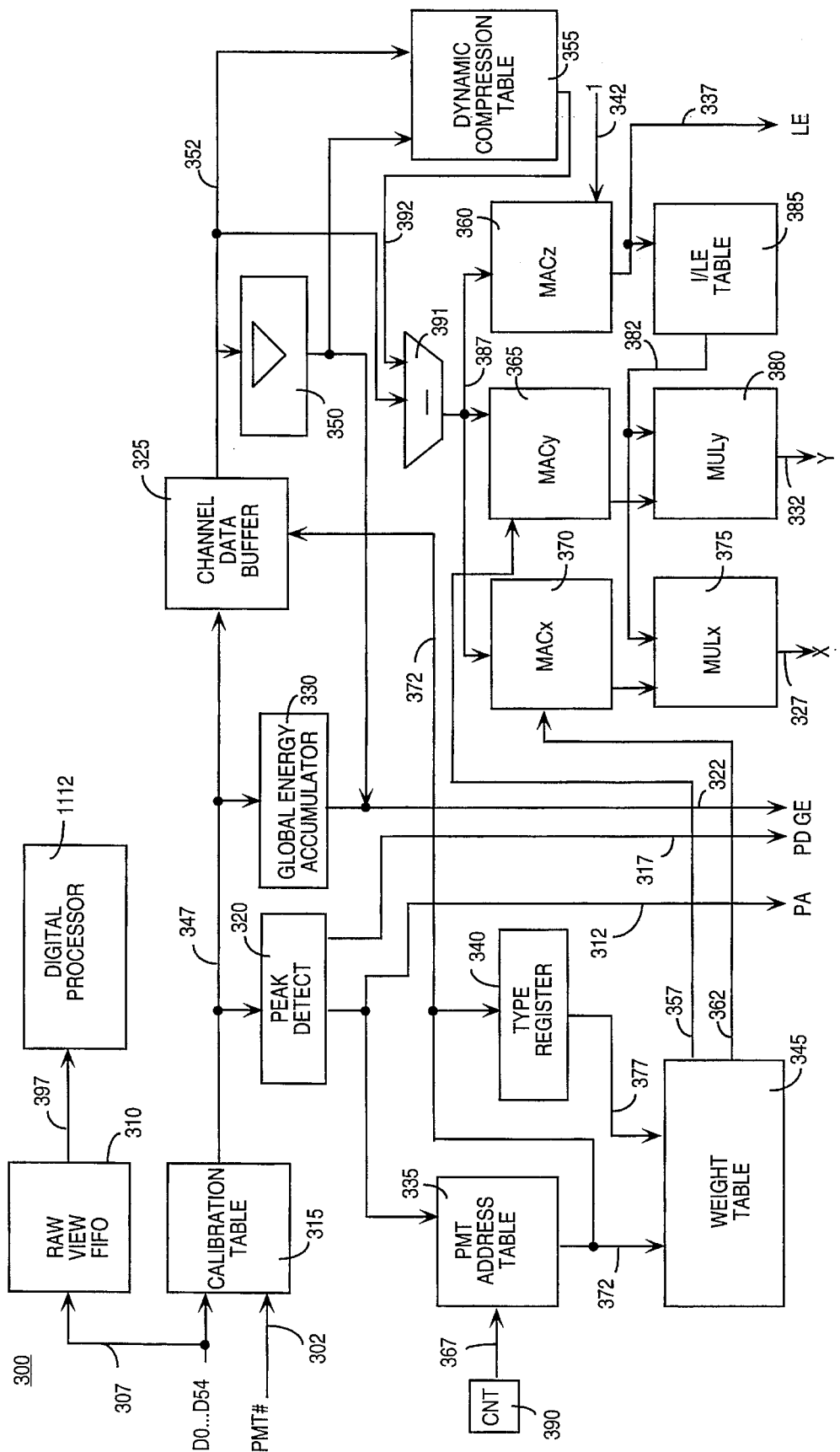
FIG. 2D illustrates the processing blocks of the present invention Digital Event Processor of each detector for generation of the spatial coordinates of an event, local and global energy, peak PMT address and the associated signal output.
Figure 3:
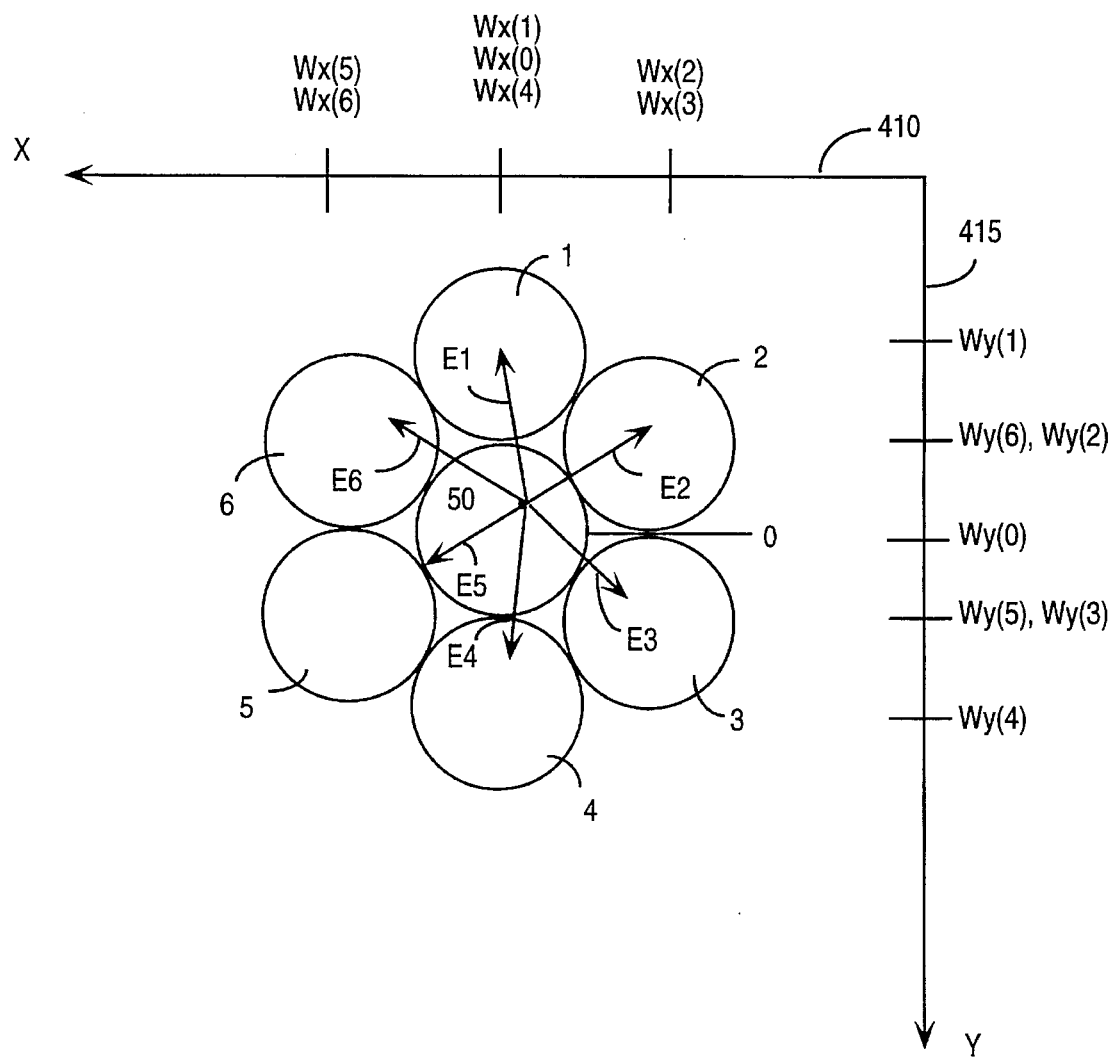

Refer to FIG. 2D which illustrates circuitry 300 of the Digital Event Processor (DEP) of the present invention. It is appreciated that the digital processor 1112 is not part of the DEP 300 circuit but is rather located within the acquisition computer system 1055. Discussions herein describe the DEP 300 associated with detector 80. A duplicate DEP circuit 300 associated with detector 80' operates in an analogous fashion with respect to input it receives from the output of preamplification/digitizer circuits associated with detector 80'. The duplicate DEP 300 associated with detector 80' is also similarly coupled to the digital processor 1112. The output of DEP 300 for detector 80 is carried over bus 1220 to the acquisition computer 1055. The output of duplicate DEP 300 for detector 80' is carried over bus 1222 to the acquisition computer 1055. Each DEP 300 of the detector pair 80 and 80' operates independently of the other to generate the X, Y, and Z outputs to the acquisition computer system 1055.

The following discussion describes the DEP 300 associated with detector 80, however, it is applicable to the duplicate DEP within detector 80'. The digitized and integrated signal values for the PMT channels over lines DO through D54 are fed over bus 307 to FIFO 310 and to calibration table 315 shown in FIG. 2D. The data over bus 307 represents the digitized integrated signals supplied from each PMT channel circuit, 280($i$), in response to a triggering event such as a scintillation event. The digitized data over bus 307 is stored into a raw view FIFO 310 that can be accessed over bus 397 by the digital processor computer 1112. The raw view FIFO allows data to be pulled from the input data stream without interrupting the normal data flow from the PMTs. This is utilized for on-the-fly baseline adjustment. A calibration table 315 receives as inputs (1) the digitized integrated channel data from bus 307 and also receives (2) PMT address (e.g., indicator) number over bus 302 of the reporting PMTs in order to correlate the digital data over bus 307 with the proper PMT channel output from circuits 280($i$).

The calibration table 315 contains a lookup table (LUT) for providing a gain output which can vary with the PMT number input (represented in one embodiment as an address); this spatially variant gain is applied to the integrated signal value received over bus 307 and the result is output over bus 347 which is a corrected or finely compensated integrated signal value for each PMT channel. The gain value stored in the calibration table 315 is a fine gain adjustment dependent on the PMT number whereas the gain amplifier 222 is a coarse gain adjustment. The calibration table 315 also provides a baseline adjustment computation by digitally subtracting the reference voltage inserted by the baseline offset circuitry (e.g., inputs 212 and 214) of the preamplification circuits for each PMT channel independently. The output over bus 347 is the digitized values supplied from 307 with this baseline adjustment.

The output of the calibration table 315 is transferred over bus 347 to a peak detect circuit 320 which analyzes all the calibrated results of all 55 channels (for a given data transfer) and selects the PMT number having the largest integrated channel signal (e.g., "energy") output for a given measured event; this is the "peak PMT." The maximum integrated signal value and the associated channel address are retained for later use in the DEP process of the present invention. The integrated signal associated with the peak PMT is output from peak detect circuit 320 over bus 317 as value PD. The PMT address number associated with the peak PMT is output by circuit 320 over bus 312 as value PA. To support analog global energy data being transferred over a digitizer channel of 280($i$), the peak detect 320 can be disabled for a given PMT address. Bus 347 is also coupled to a global energy accumulation (GE accumulation) circuit 330. Circuit 330 sums the corrected integrated channel signals output over bus 347 for each of the PMT channels for a given event. The output of circuit 330 is the digitized global energy GE (which is a digital sum of all of the PMT's digital integrated signals) and is transferred over bus 322 which forms output GE and also is coupled to the dynamic compression table 355.

Buffer 325 of FIG. 2D stores the digital integrated signal value of each PMT channel correlated with the appropriate PMT address received over bus 347. Buffer 325 can be implemented in RAM or other memory storage device. The PMT integrated signal values for all channels are stored in buffer circuit 325. The address of the peak PMT is output over bus 312 to circuit 335 which is the PMT address table. Circuit 335 contains a lookup table that outputs a PMT cluster based on a peak PMT address input from bus 312. The PMT cluster is a collection of PMTs whose integrated channel responses (as well as a total energy for the event) are used to perform the DEP computation to determine the spatial location of the event (e.g., the centroid of the cluster). By using a lookup table at circuit 335, the present invention is able to provide spatially variant cluster shape and to vary spatially the number of PMTs that form a given PMT cluster. When operating in PET imaging mode, circuit 335 is programmed to output relatively smaller (e.g. 7 PMTs) cluster sizes while operating in SPECT imaging mode, circuit 335 is programmed to output relatively larger (e.g. 17–19) sized clusters.

Within the scope of the present invention, for an input peak PMT address, the shape of the resultant PMT cluster and the number of PMTs that make up the selected PMT cluster vary based on the spatial location of the peak PMT address within the overall PMT matrix. It is appreciated that in SPECT imaging mode the PMT address table 335 can vary the PMT cluster associated with the peak PMT address based on a selection for high or low resolution wherein a low resolution mode may require 7 PMTs per PMT cluster where a higher resolution mode may require 9 to 19 PMTs per PMT cluster. Therefore, a resolution indication signal (not shown) is also input to the table 335. It is appreciated that in lieu of a resolution indicator signal, the entire table 335 can be reloaded with data for different desired resolutions. In such case the resolution signal is not used as an addressing signal but only initiates the downloading of the new information.

A sequence counter 390 is coupled to the PMT address table 335 via bus 367. The PMT address table 335 controls (1) the number of PMTs in the selected PMT cluster for the given event and (2) the type value of the PMT cluster (which is then stored in circuit 340 and held throughout the spatial computation for a given event). The PMT address table 335 also contains the address of the analog global energy channel. The sequence counter 390 then counts, sequentially, from one to the number of PMTs that are associated with the selected PMT cluster and sequentially presents each count value over bus 367. In one embodiment, the PMT address table 335 is itself addressed by two values, (1) the MSB of the address that originates from the peak PMT address value over bus 312 and (2) the LSB of the address value that originates from the count value of the sequence counter 390 over bus 367. The last entry within the PMT address table for a given peak PMT includes a stop code that indicates the end of the PMT cluster constitution for that peak PMT address. The centroid computation circuitry therefore stops (e.g., is terminated) when the stop code is reached (or equivalently when the maximum count value is reached as reported by the table 335).

The PMT address table 335 outputs over bus 372, in sequence based on the sequence counter 390, the PMT addresses of each PMT of the PMT cluster used in the spatial computation for a given event. The order in which these PMTs are presented over bus 372 is governed by the lookup table stored in the PMT address table 335 based on the peak PMT address value from bus 312 and the count value over bus 367. The PMT address values output from circuit 335 are also coupled to data buffer 325 to address this memory circuit which will output the appropriate integrated channel signal value over bus 352 for that PMT. This output is used in the DEP's spatial computation.

Referring still to FIG. 2D, the PMT cluster type value is output from the PMT address table 335 to the memory circuit 340 which holds the PMT cluster type value throughout a centroid (e.g., coordinate) computation. The PMT address values over bus 372 are also fed to a weight table circuit 345 that contains a lookup table correlating PMT address value with a given x and y weight value used for the spatial computation circuitry of the present invention. By providing the lookup table within circuit 345, the weight associated with a given PMT depends on its address value and is correlated with the spatial location of the PMT and it is also dependent on the PMT cluster type value from bus 377.

The weight value associated with a given PMT address can also vary based on the type value stored in 340 which is based on the peak PMT for the PMT cluster of the given event; this is accomplished by the type registration circuit 340 of the present invention. Therefore, if the peak PMT address corresponds to be an edge or corner PMT, then the PMT cluster will be of a special type and the weights associated with the PMT addresses of the resultant PMT cluster can be adjusted to account for the missing PMTs of the centroid computation (e.g., the PMTs that are not available due to the edge or corner location of the peak PMT). Therefore, the PMT weight value output from circuit 345 depends on (1) the PMT address value and (2) the type value from circuit 340 that is based on the address value of the peak PMT for the PMT cluster. The PMT address table 335 defines the PMT addresses that constitute the selected PMT cluster.

In one embodiment, the type registration circuit 340 may contain a lookup table based on the peak PMT address value output from circuit 335. As discussed, the PMT cluster type value is an offset into the weight table 345 for a given PMT cluster and is used to provide variations in the weights output of the weight table 345 for a given PMT address value of a given PMT cluster. Circuit 340 is coupled to supply the offset value to circuit 345 via bus 377. According to the operation of the present invention, for a given PMT cluster, the PMT addresses that make up the PMT cluster are sequentially output over bus 372 to the weight table and a constant type value is generated and output over bus 377 (based on the address of the peak PMT). The weight table 345 then outputs an x weight over bus 362 and a y weight over bus 357, for each PMT of the given PMT cluster.

The x weight value over bus 362 of FIG. 2D supplies a multiplier accumulator circuit (MACx) 370 for the x coordinate computation and the y weight value over bus 357 supplies a multiplier accumulator circuit (MACy) 365. These circuits 370 and 365 are reset and initialized at the start of the spatial computation for each gamma event. The x and y weight values are utilized in the spatial computations for a given event (e.g., gamma interaction) and specify the amount of contribution a given PMT's integrated channel signal value should carry (for a given PMT of the PMT cluster) in the coordinate computation process.

As discussed above, the PMT addresses of the PMTs of a given PMT cluster are placed over bus 372 in sequence. Bus 372 of FIG. 2D is coupled to address the buffer 325 with the PMT address value for each PMT involved in the PMT cluster. In response to the address value of a given PMT of the PMT cluster, buffer 325 outputs the stored and corrected digital signal value associated with the PMT (for a given event) as received over bus 347. This corrected signal value is transferred over bus 352 to block 350, to block 355 and to subtractor 391. A circuit 360 is coupled to receive the digital signal values of the PMT's involved in the given PMT cluster and accumulates these values to provide a local energy (LE) value which is generated over bus 337.

Block 350 is a buffer for containing either a digital or analog global energy value when operating in a mode wherein the global energy data is transferred over a digitizer channel and stored in the storage buffer 325. In this mode the global energy stored in block 350 is a digitized version of the analog global energy signal. Output from the analog signal A55 (of FIG. 2B) is fed to a preamplification digitizer channel of 280(i) and then over bus 307 to the calibration table 315 and stored in buffer 325. The global energy may also be computed by accumulator 330 by adding the values of the integrated signals from each PMT channel. The global energy value is then stored in buffer 350. Therefore, the global energy value GE over line 322 can be (1) a digitized value of the analog global energy value or (2) a digital summed value of the digital signals of each PMT channel.

The dynamic compression table 355 of FIG. 2D receives the global energy value of the detected gamma event over bus 322 and also receives the digitized integrated channel signal value for a given PMT of the PMT cluster over bus 352. The dynamic compression table 355 contains a lookup table of compensation values for the digitized integrated channel signals. The output of the lookup table is driven on bus 392 to a subtractor 391 which also receives the signal value over bus 352. The table 355 receives as an address the MSBs of the global energy (from bus 22) and predetermined bits of the signal value for each PMT over bus 352. Via the connection with the subtractor 391, the signal data over line 352 is shifted left by four bits (e.g., multiplied by 16). The output from table 355, in one embodiment, is subtracted from this left shifted signal value. The output of the subtractor circuit 391 is the dynamic compressed integrated signal value for a given PMT channel and is then fed to the MACx 370 circuit, the MACy circuit 365 and also to an energy multiplier accumulator (MACz) circuit 360.

The dynamic compression table 355 of FIG. 2D is utilized by the present invention to alter the integrated channel signal output from a PMT channel so that when summed with altered signals from other channels, the summation signal will be more linear in nature. The information stored in the dynamic compression table 355 that is used to perform the signal conversion is readily programmable within the present invention and different conversion data sets may be stored (down loaded) in the table 355 at one time. Since the conversion data may be altered readily (e.g., a new set can readily be downloaded, if needed) the dynamic compression table 355 of the present invention is modifiable. The subtraction logic 391 is a part of the compression procedure used by the present invention and is used in order to reduce the memory size requirement of the compression table 355. Therefore, it is appreciated that, given a larger memory size, the subtractor 391 may be eliminated from the present invention and integrated into the memory 355 by altering the data stored therein. The output of the dynamic compression table 355 is called the "dynamic compressed" or "compressed" integrated signal data for a particular channel and is supplied to the centroid computation logic via bus 387.

Therefore, as the sequence counter 390 counts through the PMTs of the PMT cluster, the buffer 325 supplies the integrated signal associated with each PMT. Also, the weight table 345 supplies the x and y weight values associated with each sequenced PMT. The MACx circuit 370 multiplies the x weight value and the dynamic compressed signal for each PMT and accumulates these values for each PMT of the PMT cluster as the sequencer counts. The MACy circuit 365 multiplies the y weight value and the dynamic compressed signal for each PMT and accumulates these values for each PMT of the PMT cluster as the sequencer counts. The MACz circuit has two inputs, one is coupled to bus 342 which is programmed to a value of "1," and the other input is coupled to bus 387 and therefore will accumulate the integrated signal of each of the PMTs of the PMT cluster to generate a value of the local energy (LE) over bus 337.

After the sequencer 390 of FIG. 2D reaches the last PMT of the PMT cluster, the MACz circuit will output the complete LE value over bus 337 which is coupled to a 1/LE circuit 385. This is a lookup table that provides the inverse (e.g., $(LE)^{-1}$) of the LE value. Circuit 385 can also be realized using a divider circuit. The value of (1/LE) is then output over bus 382 to x multiplier circuit (MULx) 375 and also y multiplier circuit (MULy) 380. Circuit 375 multiplies the accumulated result of the MACx circuit 370 with the (1/LE) value to generate the normalized x coordinate of the gamma event over bus 327. Circuit 380 multiplies the accumulated result of the MACy circuit 365 with the (1/LE) value to generate the normalized y coordinate of the gamma event over bus 332. Therefore, the DEP 300 of the present invention computes the spatial coordinates (x, y) and the total energy (GE) of each gamma event. Also produced for each event is the peak PMT energy (PD) which is the peak signal of the integrated channel signals received by the DEP, peak PMT address (PA) and the local energy (LE).

The X, Y, GE and LE values associated with the DEP circuit 300 of detector 80 are supplied over bus 1220 (see FIG. 1) to the acquisition computer 1055, while X, Y, GE and LE values associated with the DEP circuit 300 of detector 80' are supplied over bus 1222 to the acquisition computer 1055. In SPECT mode, the detector pair 80 and 80' perform event detection and localization relatively independently because their valid event triggering signals (1240 and 1242) do not need to be in coincidence. In PET mode, since the event detection needs to be in coincidence, the DEP circuits of both detectors 80 and 80' operate in a form of synchronization based on the coincidence of the valid event trigger signals.

The spatial coordinates (x, y) of a gamma event (interaction) are computed by the DEP 300 circuit using the below centroid computation:

$$x = \frac{Wx_1 * E_1 + Wx_2 * E_2 + Wx_3 * E_3 + \ldots + Wx_n * E_n}{E_1 + E_2 + E_3 + \ldots + E_n}$$

$$y = \frac{Wy_1 * E_1 + Wy_2 * E_2 + Wy_3 * E_3 + \ldots + Wy_n * E_n}{E_1 + E_2 + E_3 + \ldots + E_n}$$

Where:

$Wx_i$=the x weight from circuit 345 for the $i^{th}$ PMT of the Cluster $Wy_i$=the y weight from circuit 345 for the $i^{th}$ PMT of the Cluster $Wx_n$=the x weight from circuit 345 for the last PMT of the Cluster $Wy_n$=the y weight from circuit 345 for the last PMT of the Cluster $E_i$=the integrated signal for the $i^{th}$ PMT of the PMT Cluster $E_n$=the integrated signal for the last PMT of the PMT Cluster The DEP 300 operates as discussed above for each detected gamma event of an imaging session and stores the above information to a computer memory storage unit. This information is then transferred to correction electronics (or CPU system) where the data is corrected for energy, linearity, and uniformity. This can be done in either the acquisition computer 1055 or the image processor 1060. It is appreciated that a number of well known methods and circuitry components may be used for collecting the count data output from the DEP 300 circuits and for forming an image based thereon by correcting the data supplied from the DEP 300 circuits (e.g., for nonuniformities, etc.) and spatially recording the counts. Any of these well known methods may be used in conjunction within the present invention.

FIG. 3 illustrates the applicability of the above spatial computations and gives an exemplary situation. FIG. 3 illustrates a selected PMT cluster configuration as is generated based on the peak PMT address (here it is PMT0) and based on the PMT address table circuit 335. The PET imaging mode is selected in this example so the PMT cluster is composed of seven PMTs (six surrounding and one center PMT). The address table circuit 335 would also output a type registration to circuit 340 to indicate that the PMT cluster is of a symmetrical or normal type because the peak PMT is not located on the edge nor in a corner of the PMT array of the detector head 80. An exemplary x axis 410 and y axis 415 are shown and the weight values for each of the PMTs for the x and y axis are plotted along the axis for each PMT.

The exemplary event occurs at point 50 within FIG. 3 and the arrows extending outward represent the amount of light received by each PMT toward which the associated arrow points. The weight values for each of the PMTs in the x and y directions are also dependent on the spatial location of the peak PMT because the location of the peak PMT will alter the PMT type value which is used (in conjunction with the PMT address) to address the weight table circuit 345.

Figure 4A:
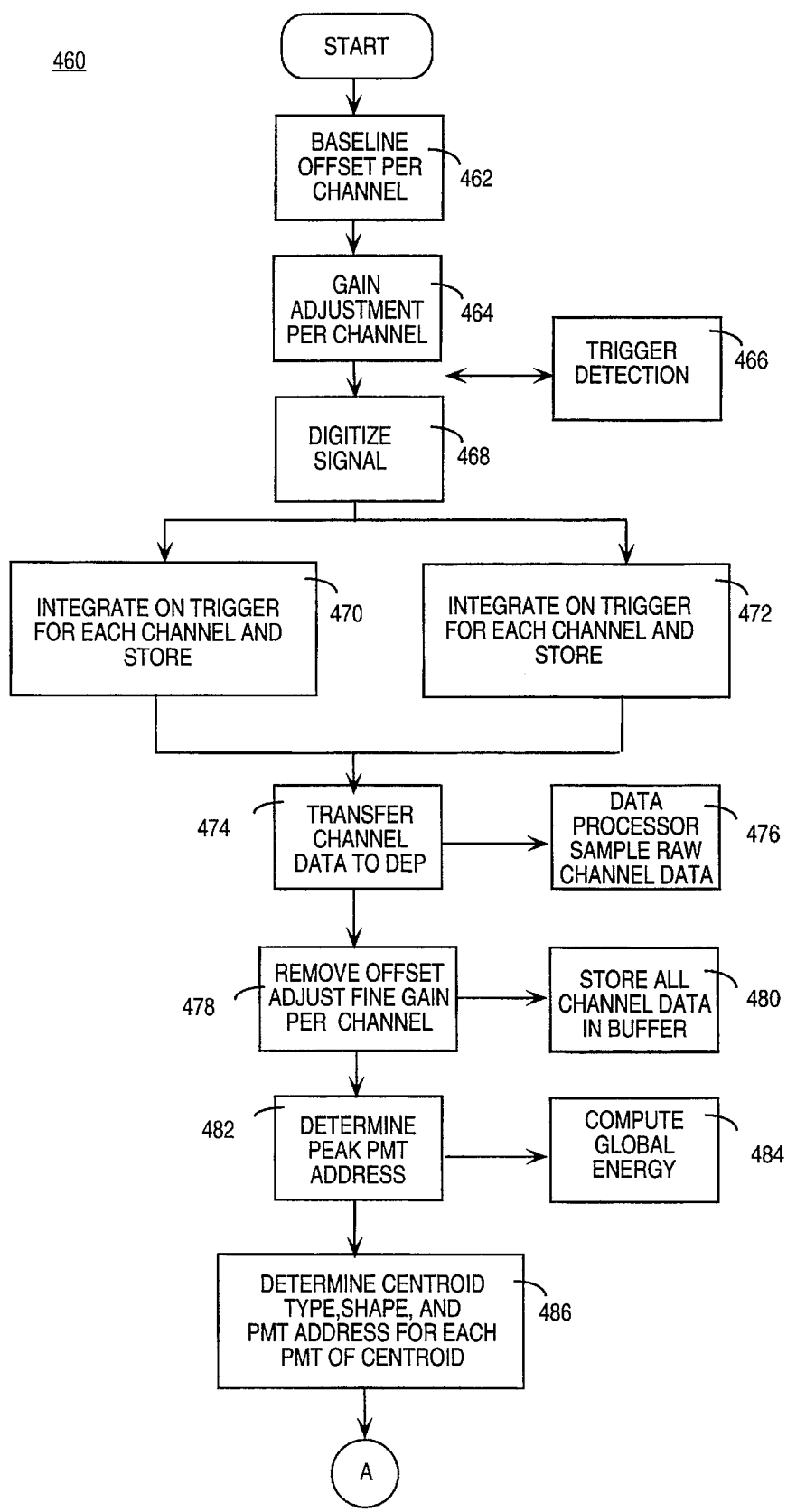
FIG. 4A and FIG. 4B illustrate an overall flow diagram of computational aspects of the Digital Event Processor of the present invention in SPECT or PET mode.
Figure 4B:
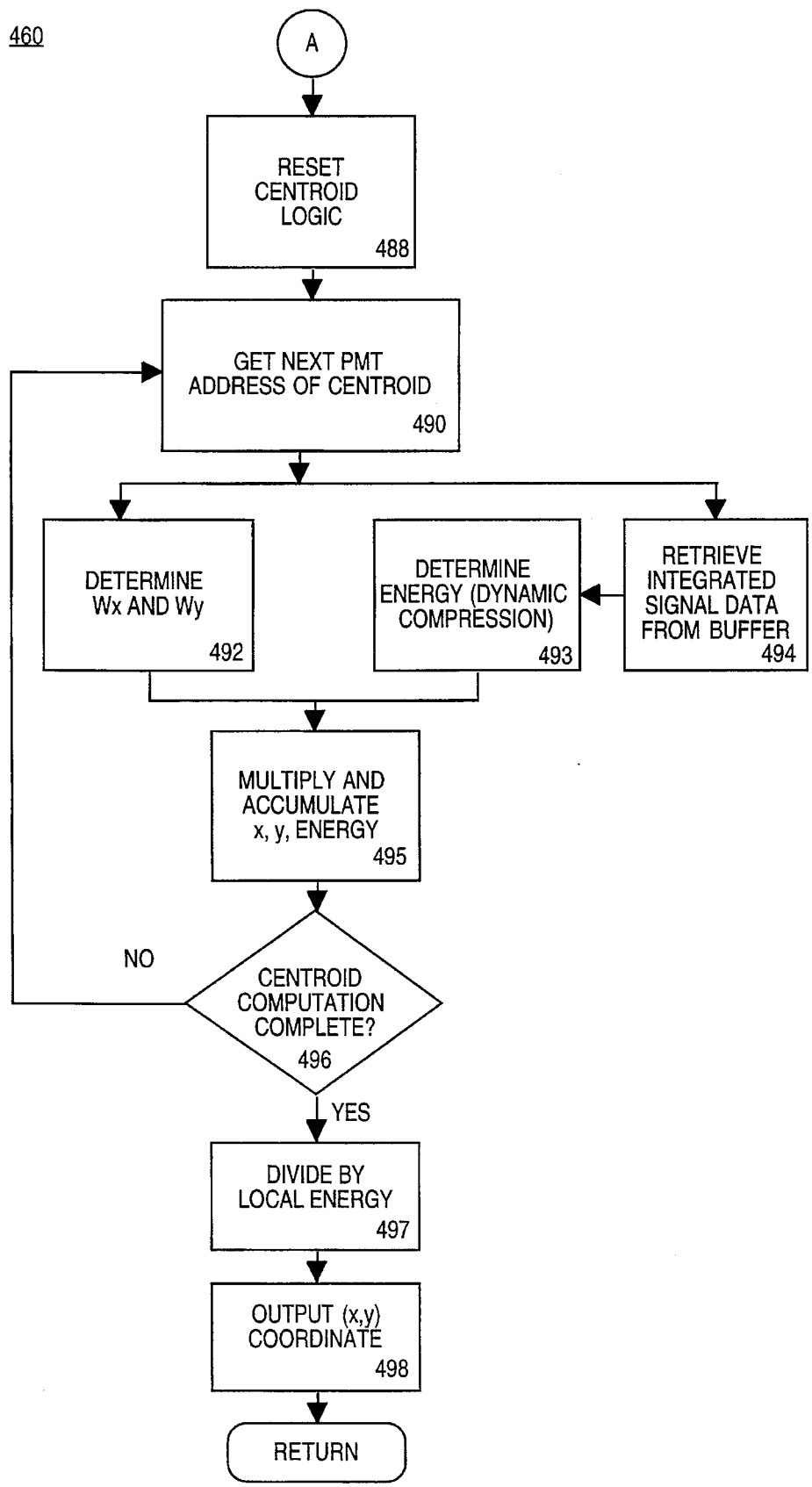

FIG. 4A and FIG. 4B are flow diagrams illustrating the general processing flow 460 of the present invention for centroiding with respect to the operations of a single scintillation detector of the detector pair 80 and 80'. Therefore, the flow 460 is performed by both detectors. It is appreciated that these flows pertain to both SPECT and PET imaging modes and that valid event trigger detection (block 466) would occur in coincidence for both detectors within PET imaging mode.

Refer to FIG. 4A where the procedure 460 enters and receives a signal, over each PMT channel, and after converting the signal from current to voltage, performs a computer controlled baseline voltage offset for each channel at 462 and also performs a computer controlled coarse gain adjustment for each channel at 464. At block 468, each channel is digitized and also trigger detection is performed at 466 by the event detection logic of the present invention. Trigger detection is divided among four area zones across the surface of the each scintillation detector. As discussed above, in PET mode, a valid event trigger detection requires a coincidence signal between both detectors 80 and 80'. As discussed above, in SPECT mode, the zonal event detectors utilize a leading edge discriminator where in PET mode the zonal event detectors utilize a constant fraction discriminator. Dual integration takes place at blocks 470 and 472 wherein a first and a second valid event trigger may be used to integrate separate events occurring close in time. The integration interval is programmable. Both integration steps output integrated signals to the two stage FIFO circuit and at 474 these data values, per channel, are transferred to the DEP sequentially at the completion of an integration interval. In PET mode the integration interval is smaller over SPECT mode. The raw data is sampled and made accessible to a data processor at 476 and this data is supplied to the calibration table at 478 which removes the baseline offset and also performs fine gain adjustment of the digital channel signal.

At 480, the data from the calibration table is stored for each channel in a buffer. At 482, the present invention determines the peak PMT by examining the channel data from the calibration table and also at 484 the global energy is determined by summing the digital data of each channel for the event. The peak PMT address is used as a measure of the coarse spatial location of the gamma event. At 486, the present invention PMT address table outputs a PMT cluster type and also determines the constitution of the PMT cluster based on the peak PMT address (and the selected resolution, e.g., fine or coarse, in one embodiment in SPECT mode.) At block 486, smaller sized PMT clusters are used in PET mode while relatively larger sized PMT clusters are used in SPECT mode.

Referring to FIG. 4B, the flow 460 of the present invention continues at 488 where the circuitry used to perform the centroid computation is reset to initialize for the new computation. At 490, the sequence counter addresses the PMT address table so that the first PMT address of the selected PMT cluster is output. From this value, and also based on the PMT cluster type, the present invention generates an x weight (Wx) and a y weight (Wy) for the selected PMT address. Also, the buffer 325 contains and supplies the stored integrated signal data for this channel at 494 and at 493 the dynamic compression circuit outputs the dynamically compressed signal value for this channel. At 495, the x and y multiplication accumulation circuits are used to multiply the weight value times the dynamic compressed signal value and accumulate the result for the PMT cluster. At 495, a local energy accumulator also accumulates the local energy of the PMT cluster. At 496, the sequence counter increments and addresses the PMT address table for a next PMT address until the PMT cluster is complete (e.g., the stop indicator of table 335 is reached); flow returns to 490 if the PMT cluster is not complete. The above processing then continues with the next PMT address of the selected PMT cluster.

If the PMT cluster is complete, then flow continues to 497 where the x and y multiplication accumulation circuits are effectively divided by the local energy to produce a normalized (x, y) spatial coordinate for the gamma event. At 498, the pertinent information output from the DEP 300 (including the (x, y) coordinate and the total energy) is output to the acquisition computer system data processor 1055 or a correction board that performs energy, linearity and uniformity correction in known manners. When operating in PET mode, a pair of x, y, and energy information is generated from each detector 80 and 80' within a coincidence window. The pair corresponds to two points detected on the scintillation detector pair 80 and 80' corresponding to two gamma rays emitted in roughly opposite directions from a position-electron interaction. This pair is recorded by the acquisition computer system 1055 as corresponding to a discrete PET event and from this pair, axial and transaxial angles of incidence are computed between the pair. The position of the position interaction lies within the line connecting the two points of the pair. When operating in SPECT mode, the acquisition computer system 1055 records the detector, 80 or 80', to which the output data for an event applies.

ACQUISITION COMPUTER SYSTEM (DIGITAL PROCESSOR)

Figure 5:
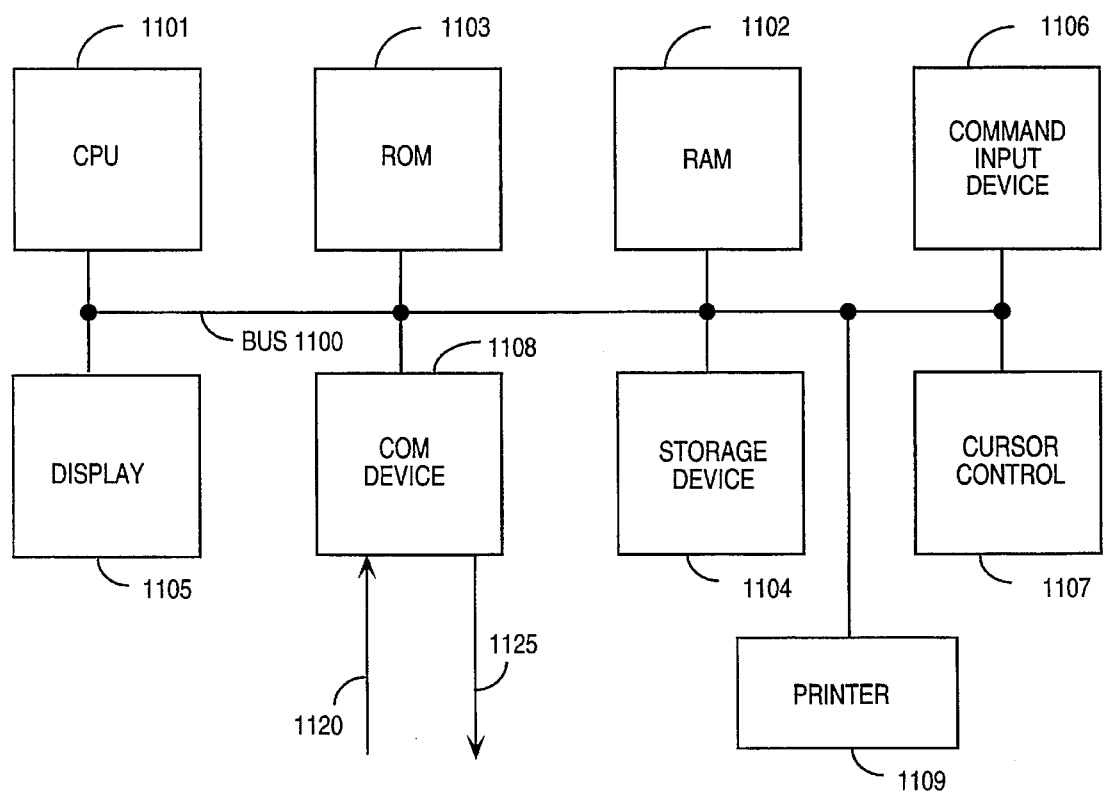
FIG. 5 is a diagram of a digital processor (computer system) and user interface of the present invention used, among other features, to automatically configure the camera system between SPECT or PET imaging modes.

Refer to FIG. 5 which illustrates components of a general purpose computer system 1112 (which can be implemented within the acquisition computer system 1055) that is capable of executing procedures of the present invention for controlling the DEP 300 circuit (e.g., control of baseline offset, gain, and trigger threshold) and for controlling the circuitry of the present invention required to switch between SPECT and PET modes of operation for performing other recited functions. The computer system 1112 comprises an address/data bus 1100 for communicating information within the system, a central processor 110 1 coupled with the bus 1100 for executing instructions and processing information, a random access memory 1102 coupled with the bus 1100 for storing information and instructions for the central processor 1101, a read only memory 1103 coupled with the bus 1100 for storing static information and instructions for the processor 1101, a data storage device 1104 such as a magnetic or optical disk and disk drive coupled with the bus 1100 for storing image information and instructions, a display device 1105 (which can also be external such as device 1065 of FIG. 1A) coupled to the bus 1100 for displaying information to the computer user, an alphanumeric input device 1106 including alphanumeric and function keys coupled to the bus 1100 for communicating information and command selections to the central processor 1101, a cursor control device 1107 coupled to the bus for communicating user input information and command selections to the central processor 1101, and a signal generating device ("communication device") 1108 coupled to the bus 1100 for communicating command selections to the processor 1101. A hardcopy device 1109 (e.g., printer) may also be coupled to bus 1100.

The signal generation device 1108 includes a high speed communication port for communicating with both DEP 300 circuits and other related circuitry. Input bus 1120 receives the data output from each DEP 300 such as signals PA 312, PD 317, GE 322, X 327, Y 332 and LE 337 over buses 1220 and 1222. Bus 1120 also supplies the raw data output from circuit 310 over bus 397 to the processor 1112 (with respect to both DEPs). Output from the processor 1112 are the control signals for controlling the fine and coarse baseline offset voltages (e.g., signals 212 and 214) and the PMT gain signal adjustment 220) for each channel. Processor 1112 also controls the trigger threshold 108. This processor 1112 also controls the state of the mode signal 1252 (FIG. 2A3) between SPECT and PET. Processor 1112 is also used to program register 1330 (FIG. 2C) to set the appropriate accumulation interval for both detectors 80 and 80' and can be used to program the PMT address table circuit 335. The raw data sampled over bus 397 and the control signals generated by processor 1112 can be determined and adjusted in real-time by the present invention.

In PET imaging mode, the processor 1112 records together the X, Y, and energy values for a pair of gamma events that are detected in coincidence. The pair corresponds to two points detected on the scintillation detectors 80 and 80' corresponding to two gamma rays emitted in roughly opposite directions from a position-electron interaction. This coincidence information is used in the image generation procedures that are common to PET scanning. From the coincidence data of a pair of interactions, a line of intersection of each event can be determined which is projected through a given plane with the object. From these two points, an axial incidence angle and transaxial incidence angle are computed and recorded. In PET imaging, other mathematical manipulations allow a complete mapping of the three-dimensional distribution of the radionuclide within the organ to be determined. These procedures are well known in PET technology and are not discussed herein.

The display device 1105 of FIG. 5 (or the display unit 1065 of FIG. 1A) utilized with the computer system 1112 of the present invention can be a liquid crystal device, cathode ray tube, or other display device suitable for creating graphic images and alphanumeric characters recognizable to the user. The cursor control device 1107 allows the computer user to dynamically signal the two dimensional movement of a visible symbol (pointer) on a display screen of the display device 1105. Many implementations of the cursor control device are known in the art including a trackball, finger pad, mouse, joystick or special keys on the alphanumeric input device 1105 capable of signaling movement of a given direction or manner of displacement. The keyboard 1106, the cursor control device 1107, the display 1105 and hardcopy device 1109 comprise the user interface associated with the image processor 1060.

DUAL INTEGRATION PER CHANNEL

The present invention provides multiple independent integrators per channel (e.g., two per PMT) in order to accurately process high count rates and to effectively reduce problems associated with pulse pile-up. This feature is particularly helpful for processing under PET imaging modes. Although described in a specific embodiment utilizing two integrators per channel, it is appreciated that the present invention system may be expanded to encompass a multiple number of integrators per channel (e.g., three, four, five, etc.). As will be discussed in further detail to follow, for each integrator added an additional stage within the serial latch circuit is required. Also, the integrators of the present invention provide a programmable integration interval.

Figure 6A:
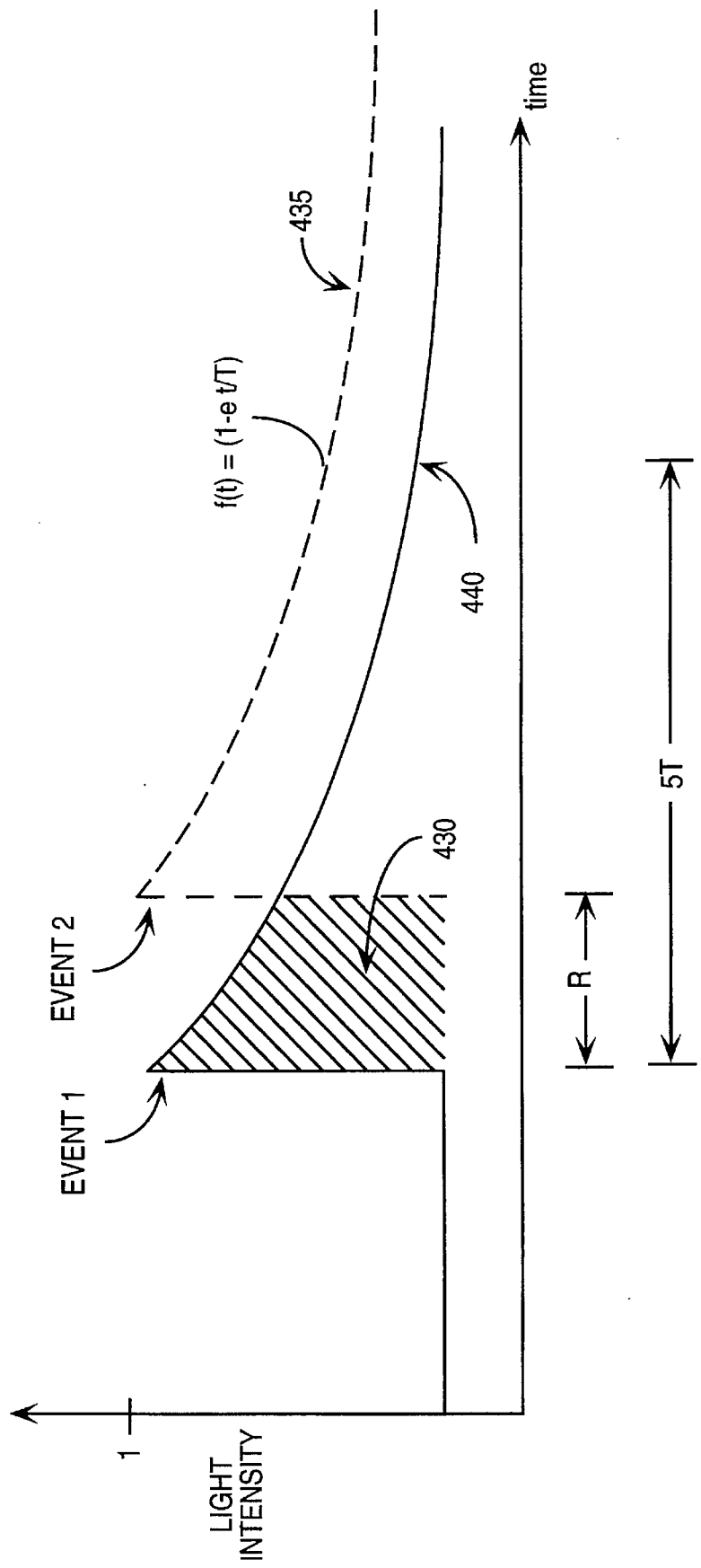
FIG. 6A represents the light intensity response for multiple events occurring close in time within the present invention.

FIG. 6A illustrates light intensity response (curve 440) over time for two events (in either PET or SPECT imaging modes). The light intensity response is a well known decaying exponential with a time constant, T. Event 1 occurs and decays over time as shown by curve 440. Due to the characteristics of the crystal 81 used in the detector 80, at the end of 5T time intervals, most of the usable light intensity is radiated. However, there is some time value R, less than 5T, that can be used and gives a sufficient amount of energy to register event1 (e.g., energy associated with region 430). Prior art systems will attempt to utilize this decreased amount of energy (region 430) for registering events during periods of high count rate (e.g., if a second event occurs before 5T as shown as curve 435). However, this is not advantageous because as the separation between events decreases below 5T, less and less event energy is captured and spatial computations become less accurate. Further, at some point, (e.g., less then R) the temporal separation between two events will become too small and neither event can be registered. At higher count rates the spatial accuracy of the prior art systems decreases significantly.

The present invention, on the other hand, provides a mechanism for integrating the energy over 5T (for example) for both event1 and event2 because dual integrators are supplied per channel for all the PMTs of the array. Therefore, one integrator may sample and integrate the light intensity for event1 over response 440 for 5T duration (or any other programmable interval) and the other can sample and integrate the light intensity for events over response 435. During periods of high count rate, the present invention does not sacrifice energy intensity when sampling each event when integrating over two events that closely occur in time. Furthermore, since two separate integrators are used, the present invention can accurately register two events even though their temporal separation is less than R. The present invention therefore provides higher accuracy at higher count rates over the prior art.

The present invention dual integrator embodiment utilizing two independent integrators is now discussed. As discussed with reference to FIG. 2C, the integration circuitry of circuit 280(*i*) for a given channel includes two integrators 238 and 240 each having independent accumulators and each coupled (via a mux 241) to a two stage sample and hold circuit (latch 242 and latch 244). Each integrator is independently triggerable and separately and independently integrates its associated channel signal over a programmable interval. Trigger signals are transmitted over bus 130 and when received, act to reset the accumulator of an idle integrator. At the end of the programmable integration interval maintained by register 1330 (FIG. 2C), for an event, the present invention transfers the data of the second stage (244) to the DEP 300, moves the data of the first stage 242 to the second stage and moves the data of the accumulator of the completed integrator into the first stage of the hold circuit. This way, both integrators may be sampling, simultaneously, different events. They can each be independently triggered and at the end of the programmable sample period, the accumulator stores its result in the two stage hold circuit.

The above procedure operates most accurately when the two integrated events are sufficiently separate from one another such that their energy dissipation across the detector does not overlap or interfere in the integration computation. For instance, refer to FIG. 7 which illustrates an exemplary PMT array. A first event occurs over PMT 7, therefore the PMT cluster 75 is composed of PMTs 1, 8, 20, 19, 36, 18, and 7. The trigger pulse resets integrator 238 (per channel) which then integrates the energy for the first event for all 55 channels. Before the integration is complete for this first event, a second event occurs over PMT 38, so the PMT cluster 73 is composed of PMTs 38, 37, 22, 23, and 39. Integrator 240 (per channel) is reset and integrates the energy associated with the second event for all 55 channels. Since PMT cluster 75 and 73 are sufficiently separate, the contribution of energy associated with the second event over channels 1, 8, 20, 19, 36, 18 and 7 is relatively small and does not interfere with the integration computation for the first event. Likewise, the contribution of energy associated with the first event over channels 38, 37, 22, 23, and 39 is relatively small and does not interfere with the integration computation for the second event.

At the end of the computation for the first event, the integrated channel signal data of latch 244 is output to the DEP 300, for a given detector, the integrated channel signal of latch 242 is output to latch 244 and the value of the accumulator of integrator 238 is output to latch 242. At the end of the computation for the second event, the integrated channel signal of latch 244 is output to the DEP, the value of latch 242 is output to latch 244 and the value of the accumulator of integrator 240 is output to latch 242. The first and second events will be processed by the DEP 300.

Figure 6B:
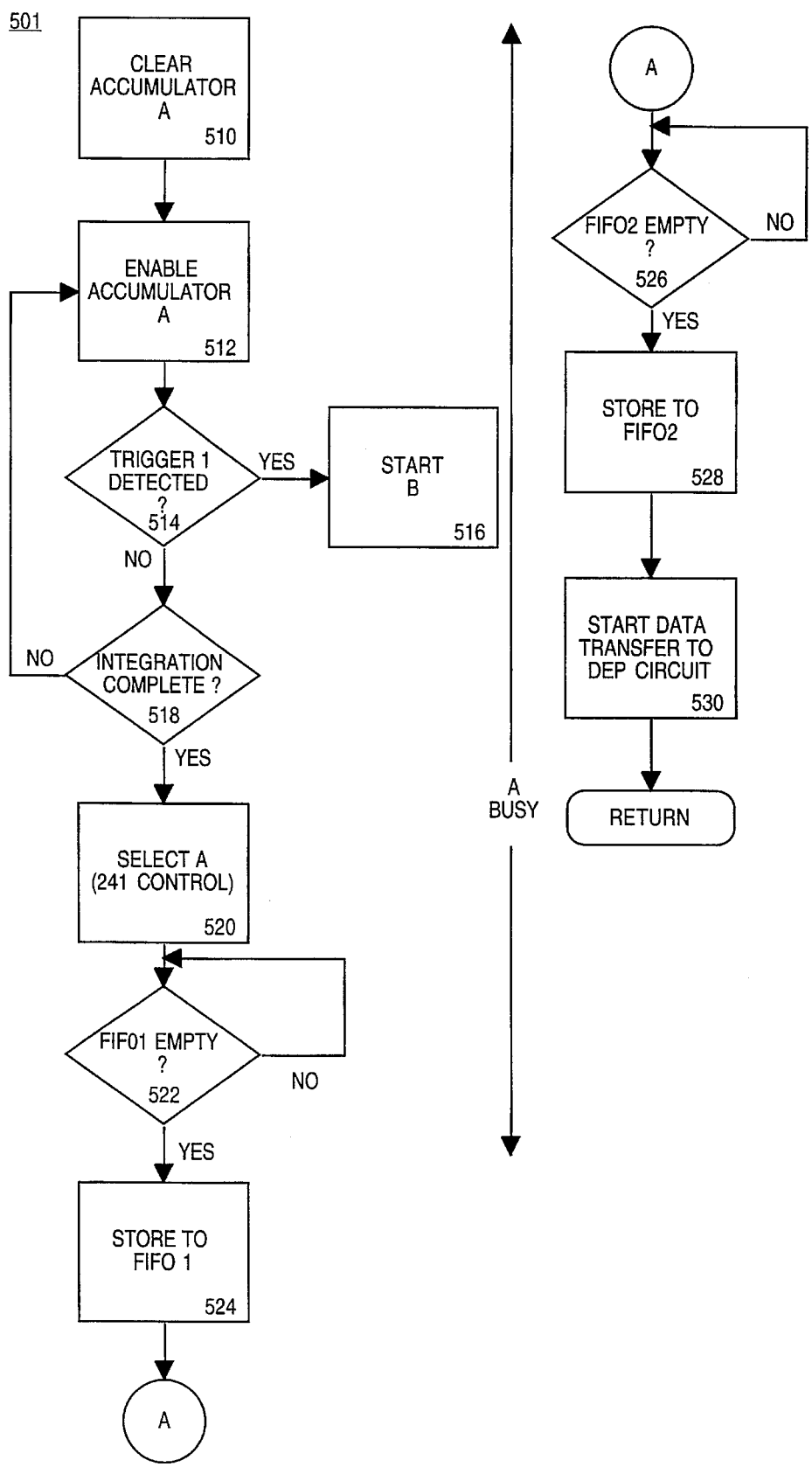
FIG. 6B illustrates a flow chart of the timing performed for dual integration on a particular channel using a programmable integration period.

FIG. 6B illustrates in more detail the process performed by the present invention to perform dual integration per channel. Each channel of each detector performs this process. The process shown 501 represents the process for integrator A but it is appreciated that the process for B (block 516) is identical except that the "B" control signals are used. As shown, the process starts at 510 in response to a valid event trigger signal, Start(t0). Then, the A accumulator is cleared (e.g., integrator 238) by assertion of a CLRACCA control signal and at 512 this accumulator is enabled to integrate by assertion of an ENACCA control signal. At block 514, if Start(t1) is detected then at block 516 the process for integrator B is started and operates concurrently with process 501. If not, then at block 518 it is checked if the programmable duration integration for A is complete. If so, not then the process returns to 512 where integration continues.

When integration for A is complete over the programmable interval, at block 520 a control signal for MUX 241 selects the data from integrator 238. At block 522 FIFO1 (242) is checked if empty and if empty, at block 524 the data is latched into FIFO1. At block 526 if FIFO2 (244) is empty then data from FIFO1 is latched into FIFO2 at block 528. At block 530 the data transfer from FIFO2 to the Digital Event Processor is started for all channels. During the period from block 510 to block 522 the A integrator is busy. It is appreciated that there is only one valid event trigger signal and it is classified as Start(t0) or Start(t1) by its temporal relationship to the other trigger signal. During the A busy period, a trigger signal will cause the B process to start. The register 1330 (FIG. 2C) can be loaded with the programmable integration period at any time but is typically loaded before an imaging session is started and is not altered during the session.

VARIABLE PMT CLUSTER CONSTITUTION

As discussed above, the PMT address table circuit 335 of the present invention contains a lookup table that provides the addresses of the group of PMTs that constitute the PMT cluster for a given event based on the peak PMT for that event (supplied from circuit 320) and based on a count value supplied over bus 357 from the sequence counter 390. A centroid is computed (using a centroiding computation) based on the PMT cluster to arrive at a spatial coordinate value of the event. In this way, the PMT cluster constitution of the present invention varies for each peak PMT. According to the present invention, also associated with each PMT of the detector array is a type registration or classification that describes the type of PMT cluster that is formed. Using the above feature, the present invention can vary the size of the cluster constitution between the SPECT and the PET imaging modes of operation.

Due to the high count rate experienced during PET imaging, the present invention, via the computer system 1112, generally controls the size of a PMT cluster to be no more than seven PMTs per cluster however, in SPECT mode the typical PMT cluster size is allowed to include more PMTs, such as 19 PMTs per cluster. The exact number of PMTs per cluster is not essential, however, the present invention advantageously allows cluster sizing to be reduced when operating in PET mode while PMT cluster sizing is increased during SPECT mode. Therefore, during initialization of a PET imaging mode of operating, the system 1112 automatically controls the programming of the present invention to select and utilize a reduced number of PMTs per cluster while during initialization of a SPECT imaging mode of operating, the system 1112 automatically controls the programming of the present invention to select and utilize an enlarged number of PMTs per cluster. Specifically, to initialize under either PET on SPECT imaging mode, computer system 1112 loads a predefined PMT cluster table (FIG. 8) into circuit 335 so that the proper PMT cluster sizes are available. The predefined tables (one for PET and one for SPECT) can be stored in unit 1102 or 1103 or 1104, for instance, before downloading into circuit 335.

Figure 7:
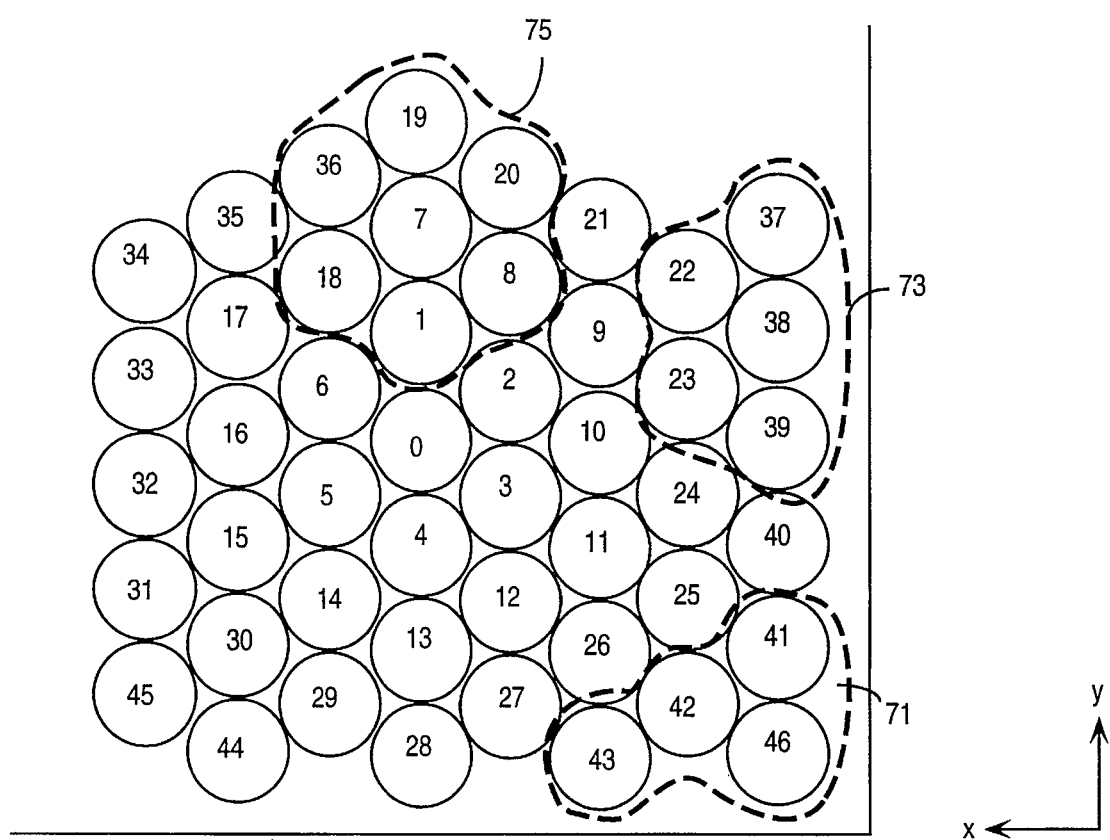
FIG. 7 illustrates an exemplary PMT array of a detector of the present invention and illustrates three different cluster types.

With regard to variable cluster shape, the present invention provides four different types of exemplary PMT clusters: 1) normal; 2) long edge; 3) short edge; and 4) corner. The normal PMT cluster anticipates the peak PMT to be located in an area of the PMT array that can be surrounded by other PMTs such that the PMT cluster is substantially symmetrical about both axis. Such a PMT cluster is shown in FIG. 7 as PMT cluster 75 with PMT 7 as the peak PMT which is surrounded by outer PMTs. The determination of the peak PMT gives a coarse spatial location for the event and the present invention PMT address table 335 is able to utilize this coarse location of the event in determining the PMT cluster constitution for that event so that the fine spatial location may be provided via the centroid computation of the DEP 300.

Two PMT cluster types (long edge and short edge) correspond to PMT clusters having peak PMTs located on the edge of the detector PMT array. Edge PMT clusters are not symmetrical about one axis. The PMT array of the present invention is rectangular and contains a long edge and a short edge and depending on the edge location of the peak PMT, the PMT cluster defined thereby can be a long edge PMT cluster or a short edge PMT cluster. The PMT clusters of these types are different because the light distribution at the long and short edges are different. An edge type PMT cluster is shown in FIG. 7 as PMT cluster 73 having PMT 38 as the peak PMT. The fourth type of PMT cluster of the present invention is a corner PMT cluster and the PMT of this type is located in a corner type of the PMT array, such as PMT cluster 71 of FIG. 7 having peak PMT 46. This PMT cluster type is not symmetrical about either axis. It is appreciated that the above PMT cluster types are exemplary and many other PMT cluster types may be utilized within scope of the present invention depending on the particular geometry of the PMT array utilized and the geometry of the detector head.

It is appreciated that for a given peak PMT address, the type value for the PMT cluster can change depending on the selected resolution of the spatial computation. For instance, a normal type PMT cluster at high resolution having the same peak PMT can be different from the PMT cluster generated at low resolution for the same peak PMT (which may be an edge type cluster). This is the case because at least in SPECT mode, at higher resolution, more PMTs are required (e.g., 17 or 19) to complete the PMT cluster rather than 7 for the low resolution cluster and these additional PMTs may overran the edge of PMT array.

Type fields are important because the PMT cluster type will effect the x and y weights assigned to a particular PMT of a particular PMT cluster in the spatial computation. For instance, PMT cluster types that are symmetrical about only one axis (e.g., edge types) will have modified weight values assigned to those PMTs of the PMT cluster that are located along the axis that is not symmetrical. For instance, refer to FIG. 3 which illustrates a spatial computation based on a normal PMT cluster type. The spatial coordinate is computed from an average of a sum based on the weight of a PMT multiplied by the integrated channel signal of the PMT for each PMT of the PMT cluster. The weight values for the PMTs must be adjusted in the computation of a spatial coordinate along an axis for which a PMT cluster is not symmetrical. Referring to FIG. 3, assume that PMTs 2 and 3 were not available because PMT 0 was located along an edge. The resulting PMT cluster is composed of PMTs 0, 1, 6, 5, and 4 and is not symmetrical about the X axis. For the coordinate computation of the X axis coordinate, the average calculation would be skewed or shifted to the left because the PMTs of the fight (e.g., PMTs 2 and 3) are missing. Therefore, the weight values of the PMTs of the resulting PMT cluster must be reduced to compensate for the skew to the left. The same is true for corner PMT clusters, however the weight values must be adjusted for the computation of both coordinates because corner PMT clusters are not symmetrical to the X or Y axis.

The weight adjustment of the PMTs based on the PMT cluster type field is made by the weight circuit 345 and will be discussed further below.

Refer to FIG. 8 which illustrates the format of the programmable PMT address table circuit 335 for low resolution selection in SPECT mode or for PET mode. The PMT address table circuit 335 is addressed by the peak PMT address value and also addressed by the count value (here shown from zero to n). Circuit 335 contains an entry for each of the 55 PMTs of the detector array. For each peak PMT, the circuit 335 outputs a PMT cluster type value and the PMT addresses of the PMT cluster. The output of the circuit 335 is (1) a PMT cluster type value and (2) the PMT addresses (a "PMT list") of the PMTs of the PMT cluster defined by the peak PMT address. Since the PMT clusters are programmable and of variable size and PMT number, a "stop" indicator is placed at the end of the PMT list (or included as part of the last PMT address entry). Exemplary data is shown in FIG. 8 and corresponds to the PMT clusters shown in FIG. 7. The first entry shown of FIG. 8 relates to PMT cluster 74 of FIG. 7 and PMT 7 is the peak PMT and the PMT cluster is a normal type having PMTs 1, 8, 20, 19, 36, and 18. Entry 38 of FIG. 8 relates to PMT cluster 73 of FIG. 7 and is an edge type PMT cluster. Entry 46 of FIG. 8 relates to PMT cluster 71 of FIG. 7 and is a corner PMT cluster.

The data stored in the memory circuit 335 that is used to formulate the PMT clusters for each peak PMT can be programmable and may be downloaded from the computer system 1112 at initialization of an imaging mode or between SPECT/PET selections. In such an embodiment, different datasets may be loaded into the memory circuit 335 for different configurations. Alternatively, the circuit 335 may be implemented using static ROM memory. In one embodiment, two separate PMT cluster tables (FIG. 8), one for PET and one for SPECT imaging, can be loaded into circuit 335 with a mode selection (line 1252) being fed into circuit 335 for selection between the two tables for PET and SPECT mode.

Based on a clock signal, the sequence counter 390 of the present invention will present the count field over bus 367 (one at a time) and this count value will address the circuit 335 along with the peak PMT address to output (1) the PMT cluster type and (2) the PMT address of the PMT cluster as shown in FIG. 8.

It is appreciated that depending on the desired count rate of the gamma camera, or the operational mode of the camera (e.g., PET or SPECT imaging modes), the PMT address table 335 of the present invention will output different sized PMT clusters for each PMT cluster type. For instance, if high resolution spatial determination is required, or if SPECT imaging is being performed, or if low count rate is expected, then the PMT clusters will be increased in size to include 17 to 19 PMTs for a normal PMT cluster (instead of seven for normal cluster types in low resolution). As discussed above, if PET imaging is desired then 7 PMTs per cluster are supplied to allow high count rate with reduced pileup. Edge and corner PMT clusters will be increased accordingly in number. Therefore, in an alternative embodiment of the present invention, the PMT address table 335 receives an additional signal indicating low or high resolution (or count rate) and this signal will address the table to supply the appropriate centroiding information based on the required resolution. Alternatively, the entire table 335 may be reloaded with a different data set to vary the resolution in SPECT mode.

Given the design of the PMT address table of FIG. 8, the number of PMTs of a given PMT cluster may easily be increased since the stop indicator, which marks the completion of the PMT cluster, is readily adjusted. Further, as stated above, the PMT cluster type corresponding to a particular peak PMT address may vary from low to high resolution settings, or for PET or SPECT imaging modes.

VARIABLE PMT WEIGHTS PER PMT

According to the present invention, the weight table circuit 345 outputs X and Y coordinate weights for each PMT of the PMT cluster based on the PMT address and the PMT cluster type information, both of which are generated by the PMT address table 335. FIG. 9 illustrates the weight table circuit 345 of the present invention. Depending on the type of PMT cluster (e.g., normal type, long edge type, short edge type, corner type, or other type) that the PMT is contained within, the x and y coordinate weights output from the circuit 345 for the PMT will vary. For each PMT address (e.g., from PMT0 to PMT54), the present invention provides a separate and programmable weight value for each coordinate computation (e.g., Wx and Wy) that varies by PMT cluster type. The values Wx are output over bus 362 and the values Wy are output over bus 357. As will be discussed below, the determination of the peak PMT gives a coarse spatial location for the event and the present invention weight table 345 is able to utilize this coarse location of the event in determining the proper weight values to assign the PMTs of the PMT cluster. The fine spatial location is computed via the centroid computation of the DEP. In such manner, the PMT address value signal over bus 372 and the type signal over bus 377 address the circuit 345.

Since some PMT clusters are not symmetrical about a given axis, for instance the X axis or Y axis for an edge type PMT cluster, the weight values associated with these axis are adjusted or varied in order to balance out the coordinate computation. This is accomplished by the present invention in order to compensate for the missing PMTs (of one axis) that are not available to provide a symmetric computation. For corner PMT clusters, the weight values associated with both axis are adjusted to compensate for the missing PMTs (of both axis) needed to provide a symmetric computation. Typically the weight values are decreased for certain PMTs in order to perform the above balancing. The values weight table 345 of the present invention may also be developed empirically based known events for certain locations.

Further, other factors such as the crystal boundaries, optical interfaces, and PMT photocathode properties can make the PMT contribution different depending on the location of the event. Since, the peak PMT address gives some indication of the coarse location of the event, the weight table 345 can compensate for the above factors by providing variable weights.

Therefore, the present invention provides the ability to adjust or alter the weight values for a given PMT depending on the PMT cluster type in which the PMT is located. Depending on the location of the peak PMT, the weight values for the PMTs used in the centroid computation may alter. These weight values are also dependent on the peak PMT address since the peak PMT address defines the PMT cluster type within the present invention. The ability to assign different weighting factors based on the peak PMT location permits higher accuracy in the centroid computations and reduces the demands on the correction processing steps. This contributes to allowing the detector 80 to have larger field of view without increasing the crystal dimensions.

The data stored in the memory circuit 345 of FIG. 9 that is used to provide the variable weights for each PMT can be programmable and may be downloaded from the computer system 1112. In such an embodiment, different datasets may be loaded into the memory circuit 345 for different configurations. Alternatively, the circuit 345 may be implemented using static ROM memory.

In operation, as the counter 390 counts sequentially, the PMT address table 335 outputs a sequential listing of PMT addresses within the PMT cluster. The type signal generated by bus 377 addresses the MSBs of the of the memory 345 and the PMT addresses are the LSBs. As each PMT is generated over bus 372, the memory circuit 345 generates an X and Y weight value (over buses 357 and 362) associated with the current PMT output over bus 372. This information is fed to the centroiding circuitry for computation of the spatial coordinate a the gamma event.

The dual head camera system of the present invention can also employ automatic gain correction (autogain correction), a variable dynamic compression table, and software or scintillation triggered baseline compensation. These features are further described in copending application Ser. No. 08/488,926, filed on Jun. 9, 1995, entitled, Multi-Head Nuclear Medicine Camera For Dual SPECT And PET Imaging, and assigned to the assignee of the present invention.

SWITCHABLE PET AND SPECT MODES OF OPERATION

Figure 10:
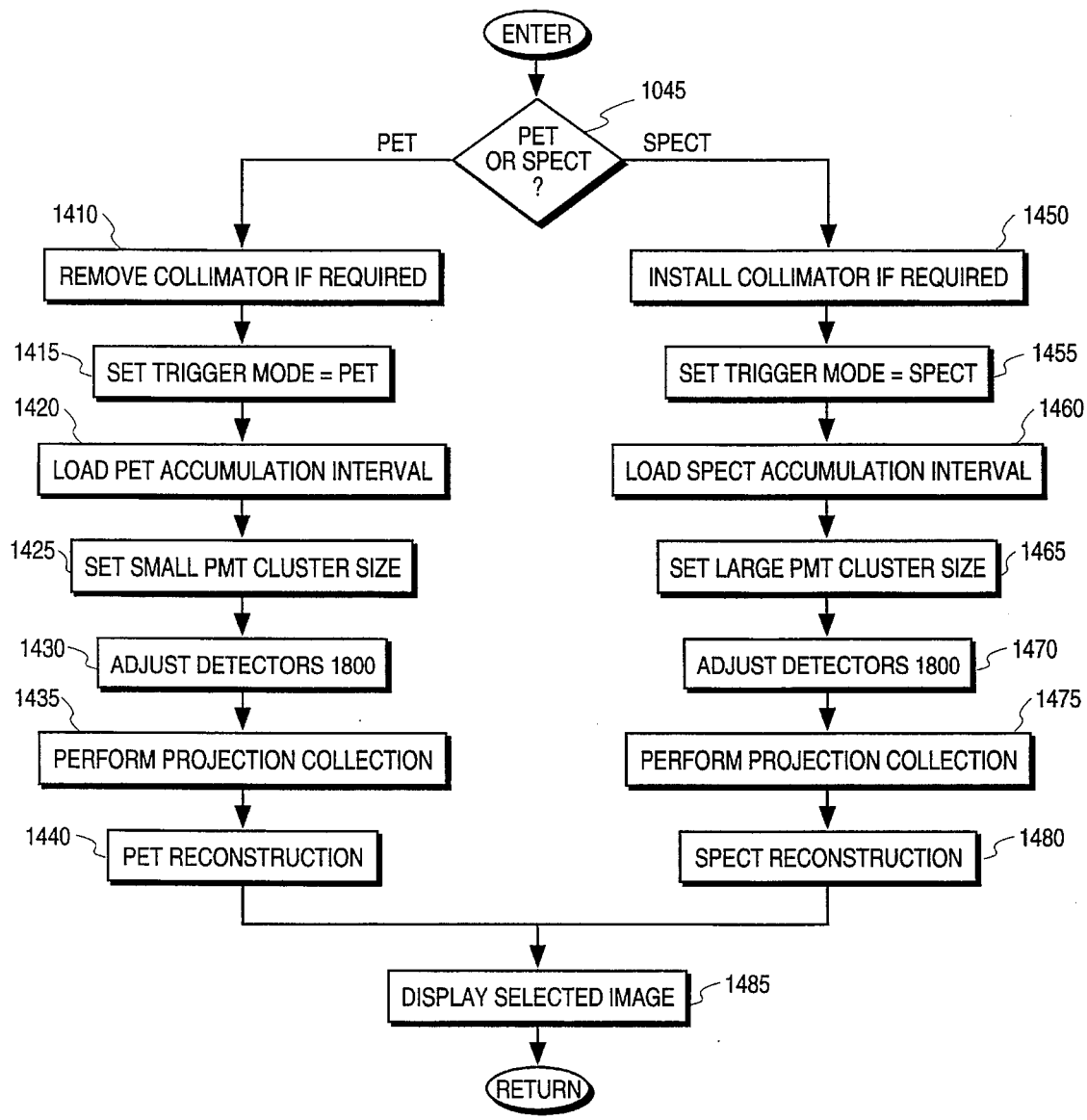
FIG. 10 is an illustration of a procedure utilized by the present invention for automatically switching between SPECT and PET imaging modes of operation for medical imaging.

FIG. 10 illustrates a process 1400 utilized by the present invention when switching between SPECT and PET imaging modes of operation. When operating within PET imaging mode, the patient is injected with a Flouro Deoxi Glucose (FDG) or similar radiopharmaceutical prior to imaging emitting a pair of 511 keV gamma rays. In SPECT mode, the patient is injected with a TI-201 radiopharmaceutical prior to imaging emitting a 140 keV gamma ray. Process 1400 of the camera system of the present invention starts at block 1405 wherein the system checks the user interface device (e.g., 1106 of FIG. 5) or memory 1102 to determine if a PET or SPECT imaging mode of operation is requested. If PET mode of operation is requested, then at block 1410, the camera system verifies to determine if the collimators are removed from the detectors 80 and 80'. Processing is suspended until the collimators are removed and an indication is displayed on unit 1105 or 1065 to indicate the presence of the collimators. If the collimators are removed, then the process continues to block 1415 wherein the camera system programs the trigger mode (e.g., line 1252 of the CTC 1050 of FIG. 2A3) to be in PET imaging mode. This will require coincidence trigger detection to generate a valid event trigger over lines 1240 and 1242.

At block 1420, the computer system loads the PET integration (accumulation) interval (e.g., approximately 320 ns) over line 235 of FIG. 2C into register 1330 for both detectors 80 and 80'. At block 1425, the present invention directs the computer system to set or download a PMT cluster table having a smaller PMT cluster size (e.g., 7 PMTS) into the PMT address table 335 of FIG. 2D for each indexed peak PMT. This is accomplished by programming the PMT address table (see FIG. 8) so that the cluster sizes are smaller for each peak PMT. At block 1430, the present invention adjusts the configuration of the detectors 80 and 80' such that they are at a 180 degree orientation for imaging. At block 1435, the present invention performs a PET imaging session across a number of ECT projection angles with the detectors 80 and 80' in their 180 degree configuration. For each projection angle, within block 1435, data is collected by the present invention on an event by event basis according to the flow diagrams shown on FIG. 4A and FIG. 4B. Within PET mode, coincidence detection is performed between detectors 80 and 80' for the events. Collected data is recorded into the acquisition computer system 1055 (FIG. 1). It is appreciated that in PET mode, the energy value, Z, output by the detectors in response to an event is the sum of the energy detected by the cluster used to localize the event and not the sum of all the PMTS in the detector as is sometimes used in SPECT imaging. The collected data is then imaged by image processor 1060 and PET reconstruction is performed on the projection data at block 1440. PET reconstruction procedures on projection data are well known and are not discussed in detail herein. It is appreciated that at block 1440, attenuation correction maps, if available, can be applied to the emission data to correct for nonuniform attenuation during reconstruction. Collection of nonuniform attenuation correction maps is described further below.

At block 1485, a user-selected image from the PET reconstruction can be displayed on display screen 1065 or display 1105. Since PET imaging data is collected without a collimator, the resolution of PET images is generally of higher quality over SPECT images. It is appreciated that the processing of blocks 1410–1430 can occur in any order and the order presented is exemplary only.

With respect to FIG. 10, if SPECT mode of operation is requested at block 1405, then at block 1450, the camera system verifies to determine if the collimators are present on the detectors 80 and 80'. Processing is suspended until the collimators are installed and an indication is displayed on unit 1105 or 1065 to indicate the absence of the collimators. If the collimators are installed, then the process continues to block 1455 wherein the camera system programs the trigger mode (e.g., line 1252 of the CTC 1050 of FIG. 2A3) to be in SPECT imaging mode which does not require coincidence detection for valid event trigger generation.

At block 1460 of FIG. 10, the computer system loads the SPECT integration (accumulation) interval (e.g., approximately 840 ns) over line 235 of FIG. 2C into register 1330 for both detectors 80 and 80'. At block 1465, the present invention directs the computer system to set a relatively larger PMT cluster size (e.g., larger than 7, for instance, 19 PMTS) into the PMT address table 335 of FIG. 2D for each indexed peak PMT. This is accomplished by programming the PMT address table (see FIG. 8) so that the cluster sizes are relatively larger for each peak PMT. At block 1470, the present invention adjusts the configuration of the detectors 80 and 80' such that they are at a 180 degree configuration for imaging. At block 1475, the present invention performs a SPECT imaging session across a number of projection angles with the detectors 80 and 80' in their 180 degree configuration. For each projection angle, within block 1475, data is collected by the present invention on an event by event basis according to the flow diagrams shown on FIG. 4A and FIG. 4B. Within SPECT mode, coincidence detection is not performed. Collected data is recorded into the acquisition computer system 1055 (FIG. 1). The collected data is then imaged by image processor 1060 and SPECT reconstruction is performed on the projection data at block

1480. SPECT reconstruction procedures on projection data are well known and are not discussed in detail herein. It is appreciated that at block 1480, attenuation correction maps, if available, can be applied to the emission data to correct for nonuniform attenuation during reconstruction. Collection of nonuniform attenuation correction maps is described further below.

At block 1485, a user-selected image from the SPECT reconstruction can be displayed on display screen 1065 or display 1105. It is appreciated that the processing of blocks 1450–1470 can occur in any order and the order presented is exemplary only. Using the procedure 1400, the present invention offers a nuclear camera system automatically switchable and optimized between SPECT and PET imaging capabilities.

TRANSMISSION ACQUISITION AND NONUNIFORM ATTENUATION CORRECTION

The following section describes the use of nonuniform attenuation correction within the above described dual head switchable PET and SPECT nuclear camera system. It is appreciated that in addition to the transmission acquisition features described herein, the present invention camera system can also take advantage of the features described in co-pending patent application entitled, Dual Synchronized Sliding Transmission Detection Windows for Dual Transmission Line Sources, filed on May 11, 1995, Ser. No. 08/439,222, and assigned to the assignee of the present invention. For instance, the present invention can utilize a transmission scan speed feature, variable filters on the transmission line sources, and use of a large field of view transmission acquisition with a small field of view emission acquisition.

An embodiment of the present invention is described for reducing the effects of side scatter (or cross-talk) during simultaneous transmission scanning and can be used also during transmission and SPECT emission scanning using the above described camera system. In order to describe the operation of the transmission acquisition of the present invention, for the following section it is assumed that the dual PET/SPECT camera system is switched to SPECT imaging mode.

In one embodiment of the present invention, two sliding transmission detection windows are utilized and move across the detector surfaces in conjunction with the two scanning line source assemblies 1520 and 1522 (also called scanning line sources) of FIG. 1B. The transmission detection windows are electronically generated and are used to define a particular area within the field of view of a detector. In all discussions to follow within this transmission embodiment of the present invention, it is assumed that each detector (e.g., detector 80 and 80') is collimated and further that this embodiment of the present invention can be implemented within a gamma camera performing (1) simultaneous or (2) sequential SPECT emission/transmission scanning. Alternatively, as will be described further below, the dual SPECT/PET camera system of the present invention can be utilized to perform transmission acquisition followed by a PET emission acquisition.

For transmission acquisition, the two line sources and the two sliding windows move in synchronization to scan the field of view of the detectors and at any given position are all located within a single spatial plane (e.g., the long axis of the two line sources and the length of the two transmission detection windows are aligned within a single spatial plane). This spatial plane is transverse to the long axis of the object or patient being scanned. Particularly, if considering the gamma camera arrangement of FIG. 1B, this spatial plane is perpendicular to the axis that runs through the two gantry rings 85. Using this dual line source scanning configuration, cross talk or scattered radiation originating from a given line source is not detected as emission data by the detector that is not associated with the given line source (e.g., the detector that is not directly facing the line source). Secondarily, the effect of emission cross-talk is also reduced when performing a simultaneous PET emission acquisition.

The sliding transmission detection windows defined within the field of view of the detectors 80 and 80' are programmed by the computer system 1112 to detect only photons within the energy level of the transmission radiation; photons of the emission radiation level detected within the window are ignored by the camera system. The ability to electronically define a window region within a scintillation detector is well known in the art, for instance reference is made to U.S. Pat. No. 5,304,806, entitled, "Apparatus and Method for Automatic Tracking of a Zoomed Scan Area in a Medical Camera System," issued Apr. 19, 1994, and assigned to the assignee of the present invention, which discusses tracking or "roving" zoom regions. As is known, a window region can be defined within and moved across the field of view of the detector and by acquisition processing, certain data detected by the scintillation detector within the window can be collected or ignored.

Figure 11A:
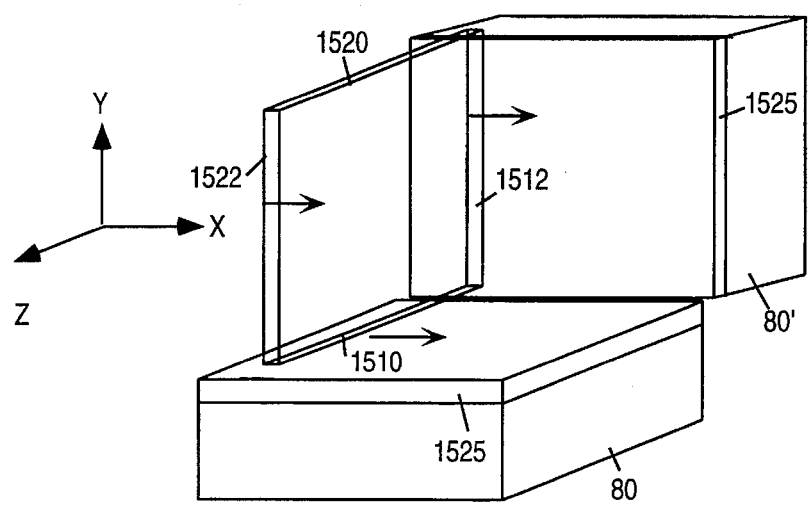
FIG. 11A, FIG. 11B, and FIG. 11C, illustrate transmission scan progression of the present invention transverse orientation dual line source transmission scanning configuration.
Figure 11B:
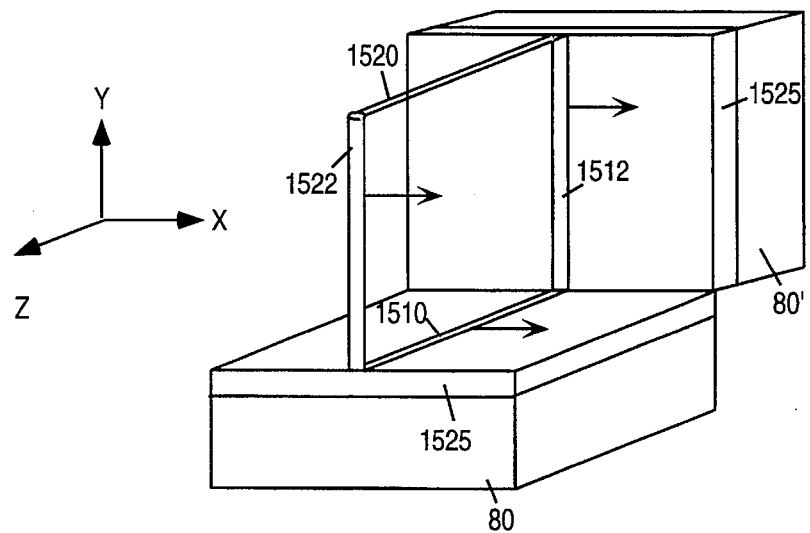
Figure 11C:
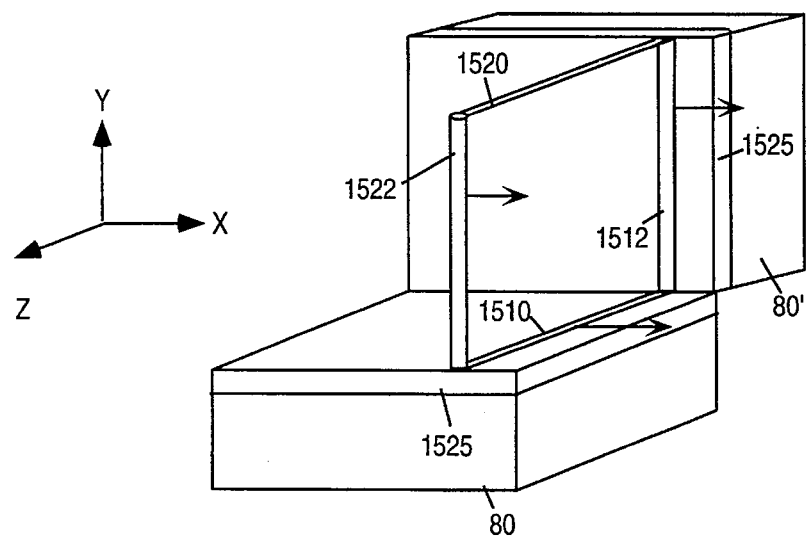

An illustration of the transverse orientation dual line source scanning and dual transmission detection window configuration of the present invention are shown in FIG. 11A, FIG. 11C and FIG. 11C. Detectors 80 and 80' are shown in a 90 degree configuration. Detector 80 is said to be associated with line source assembly 1520 and detector 80' is said to be associated with line source assembly 1522. There is a separate collimator 1525 located in front of each detector 80 and 80' in order to collimate incoming photon radiation to the detector surface during transmission. As discussed above, each line source assembly 1520 and 1522 has its own collimating slit. A transmission window region 1512 is defined within the field of view (FOV) of detector 80' and corresponds to line source assembly 1522. This window region 1512 spans the length of the field of view of detector 80' along the Y axis and in width (along X axis) is large enough to detect (and contain) the collimated transmission radiation emitted from line source assembly 1522. The long axis of line source assembly 1522, as discussed above, extends along the Y axis. Additionally, a second transmission window region 1510 is defined within the field of view (FOV) of detector 80 and corresponds to line source assembly 1520. This window region 1510 spans the length of the field of view of detector 80 along the Z axis and in width (along X axis) is large enough to detect (and contain) the collimated transmission radiation emitted from line source assembly 1520. The long axis of line source assembly 1520, as discussed above, extends along the Z axis.

To gather transmission radiation, the line source assemblies 1520 and 1522 move along the X axis and scan an object with transmission radiation which is detected within the transmission detection windows of the detectors 80 and 80'. As the line source assemblies move along the X axis in synchronization with each other, the associated transmission window regions 1510 and 1512 also move in synchronization along the X axis with their associated line source assembly.

The progression of the line source assemblies and transmission detection windows along the X axis is shown in FIG. 11A, FIG. 11B and FIG. 11C. In FIG. 11A, the two line sources 20, 22 and the two transmission detection windows 410, 412 are shown at a given (start) position along the X axis. In FIG. 11B, the two line sources and transmission detection windows are shown in a further (mid) x axis position. In FIG. 11C, the two line sources and transmission detection windows are shown in another (end) X axis position. Effectively, in electronics, the transmission detection windows 410, 412 are scanned across the detectors FOVs in synchronization with the line sources and create two spatial acceptance windows for acceptance of transmission data and rejection of photon radiation within the emission energy level. It is appreciated that a transmission scanning operation can also occur in the reverse direction across the detector's FOVs, e.g., from FIG. 11C to FIG. 11B to FIG. 11A.

It is appreciated that the computer system 1112 is programmed according to the present invention to define the transmission detection windows 1510, 1512 and to displace or scan them along the surface of the detectors 80 and 80' during a transmission scan. Defining a transmission detection window and scanning such along the field of view of a detector is well known in the art, for instance, as taught by Tan et al. in the reference entitled "A Scanning Line Source for Simultaneous Emission and Transmission Measurements in SPECT."

In this configuration, at any point along the x axis, the two line sources 1520 and 1522 and the two transmission detection windows 1510 and 1512 are located within the spatial YZ plane. Regardless of the position along the X axis of the transverse line source assembly of the present invention, the long axis of two scanning line sources 1520 and 1522 and the long axis of two transmission detection windows 1510 and 1512 remain within a single YZ spatial plane, for instance, refer to FIG. 11A, FIG. 11B, and FIG. 11C.

Under this configuration, the long axis of the dual line source assemblies and the dual transmission detection windows are within a spatial YZ plane that is perpendicular (transverse) to long axis of the object being scanned (e.g., assumed to along the X axis). Therefore, the configuration of the present invention is called a "transverse" transmission configuration.

During the scan session, transmission radiation is emitted from the line sources and this transmission radiation is detected by the scintillation detectors after passing through an object of interest. Simultaneously, emission radiation is emitted from the object and is detected by the detector. Within the present invention, the transmission radiation is utilized to create a nonuniform attenuation correction map of the object being scanned. Only transmission photons (e.g., photons detected within the transmission energy range) are detected within transmission detection windows 1510 and 1512. Emission photons (e.g., photons detected within the emission energy range) are ignored within the transmission detection window. Due to source and detector collimation and the configuration of the present invention, transmission photons are not detected outside the transmission detection windows 1510 and 1512. While transmission information is detected and collected within transmission detection windows 1510 and 1512, the remainder of the FOVs of the detectors detect and collect emission data.

Figure 12A:
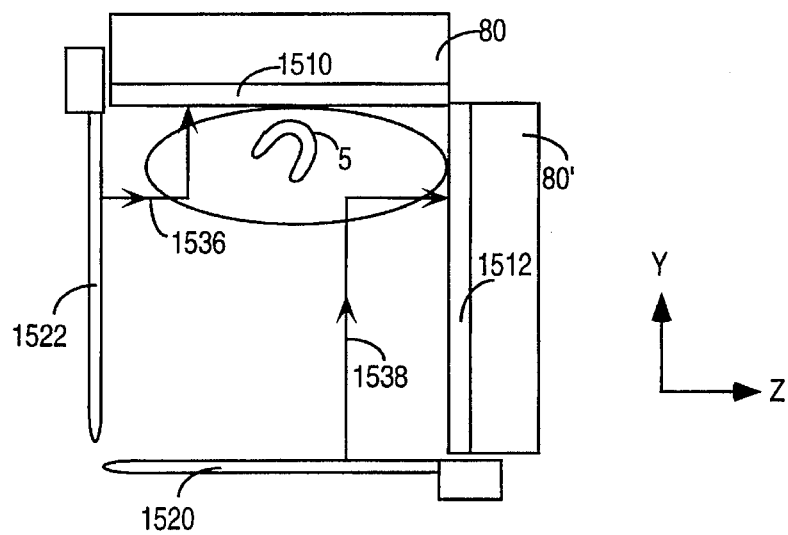
FIG. 12A illustrates transmission cross-scatter effects and elimination using the present invention transverse orientation dual line source transmission scanning configuration.

FIG. 12A illustrates in manner in which the transverse configuration of the present invention effectively eliminates the effects of cross-scattering of transmission photons from contaminating the simultaneous SPECT emission image. Essentially, line source collimation and detector collimation (within the configuration of the present invention) ensure that: (1) nonscattered transmission photons fall into the transmission detection window of an associated detector to the radiating line source; and (2) cross scattered transmission photons are detected in the transmission detection window of a detector that is not associated with the radiating line source (e.g., the orthogonal line source). For example, nonscattered transmission photons radiated by line source 1520 are detected within transmission detection window 1510 and scattered transmission photons radiated by line source 1520 are detected within transmission detection window 1512 and vice-versa for transmission photons emitted from line source 1522. The above is true irrespective of the position of the line sources and transmission detection windows as they are scanned in synchronization along the X axis (which is into and out of the plane of FIG. 12A).

As discussed above, during transmission acquisition, various photon radiation sources can be used within the scope of the present invention. An exemplary implementation is the use of Tl-201 (at 72-keV) for the emission radiation source and Gd-153 (at 100-keV) as the transmission radiation source. FIG. 12A illustrates a cross section (in the YZ plane) of the detector configuration of the present invention. The present invention configuration rejects Gd scatter within the Tl transmission detection windows 1510 and 1512. A side view of sources 1522 and 1520 are shown and detectors 80 and 80' are shown in a 90 degree configuration. As discussed above, the detectors are each collimated.

A 100-keV transmission photon (Gd-153) is emitted from line source 1522 along path 436, cross-scatters within the object 5 and is detected within nonassociated transmission detection window 1510 (e.g., within the orthogonal detector). The detection window 1510 is not associated with source 1522 because transmission radiation emitted from line source 1522 should be detected by the associated detection window 1512 (e.g., absent photon scatter). Due to the configuration of the present invention, this cross scattering photon is forced to be detected within window 1510, otherwise, it would have been absorbed by the detector's collimator and not detected at all by detector 80. There is no other location within detector 80 or detector 80' where the cross-scattering transmission photon can end up (assuming only one scatter event occurs) besides a transmission detection window.

The scattering within object 5 reduces the energy of the transmission photon, so it is detected within transmission detection window 1510 at 72-keV (which is within the emission energy level). However, within the present invention, window 1512 only responds to photons within the transmission energy level (e.g., within 100-keV). Therefore, this scattered transmission photon (having a Tl-201 count) is vetoed by the transmission detection window and not recorded by detector 80. Tl-201 photons detected elsewhere within the FOV of detector 80 are recorded as proper emission photons. It is appreciated that if the photon had cross scattered out of the (YZ) plane of FIG. 12A, due to collimation of the detector 80, the photon would not have been detected by detector 80. In addition, since the source 1522 is collimated, nonscattered transmission photons are not detected outside window 1512 of detector 80'.

Shown by FIG. 12A, cross-scattering can also occur as a result of transmission radiation (100-keV) emitted from line source 1520 shown by path 1538. The transmission photon cross-scatters through object 5 and due to the configuration of the present invention the cross scattering photon is detected within nonassociated detection window 1512. However, after scattering, the photon loses energy and becomes a 72-keV energy photon. Window 1512 responds only to photons within the transmission energy level (100-keV in this example), therefore, this cross scattered photon is ignored. If the cross scattered photon did not remain within the YZ plane of FIG. 12A, it would have been stopped by the collimator of detector 80' and not detected at all. The remainder of the FOV of detector 80' is free to detect and collect emission radiation within the 72-keV energy level. Since the source 1522 and detector 80' are collimated, nonscattered transmission photons are not detected outside window 1512. Since the source 1520 is collimated, nonscattered transmission photons are not detected outside window 1510.

As a result of the present invention, cross scattering transmission photons are not allowed to fall within regions of any detector that are gathering emission data. This effectively eliminates the contamination of cross scattering transmission data within the SPECT emission image of a dual detector gamma camera. When a scattered transmission photon falls within a transmission detection window, the scatter photons are effectively eliminated by the data acquisition electronics of the present invention due to energy discrimination.

The SPECT emission image is free of cross-scatter contamination because the crossscatter photons emitted from line sources 1520 and 1522 either: (1) fall within nonassociated detector regions 1512 and 1510 (respectively) and are therefore ignored; or (2) are absorbed by the detectors' collimators and are not detected at all. Further, transmission radiation (emitted by the line sources) that does not scatter is detected within associated transmission detection windows 1510 and 1512 and does not contaminate the emission image. Within the present invention, there is no need to perform additional measurements to estimate and subtract effects due to cross-scatter.

Figure 12B:
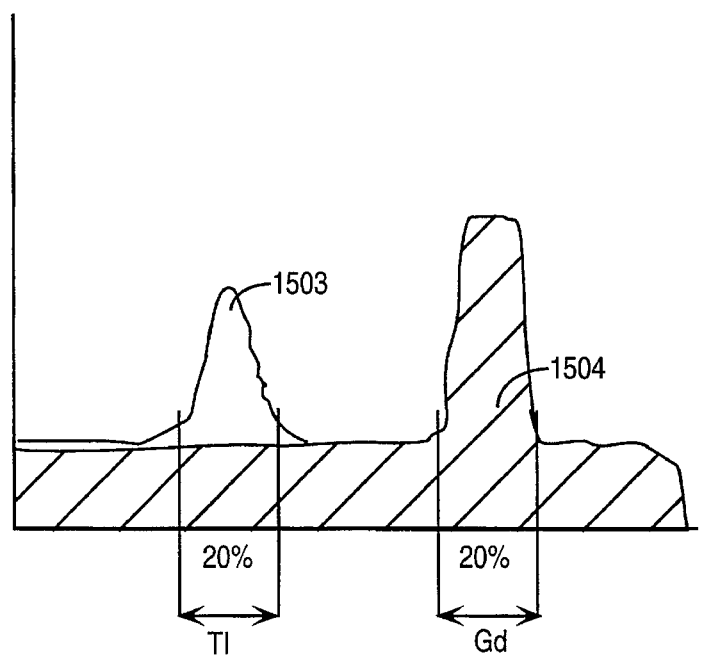
FIG. 12B illustrates photopeak energy distributions for emission/transmission energy level photons.

FIG. 12B illustrates the energy distribution of detected photons resultant from the configuration of FIG. 12A. As shown in FIG. 12B, the shaded area 1504 represents the emission Gd photopeak plus the scatter radiation. As shown, the scatter distribution tails into the transmission Tl window. Also shown is the Tl photopeak distribution 1503.

Figure 13A:
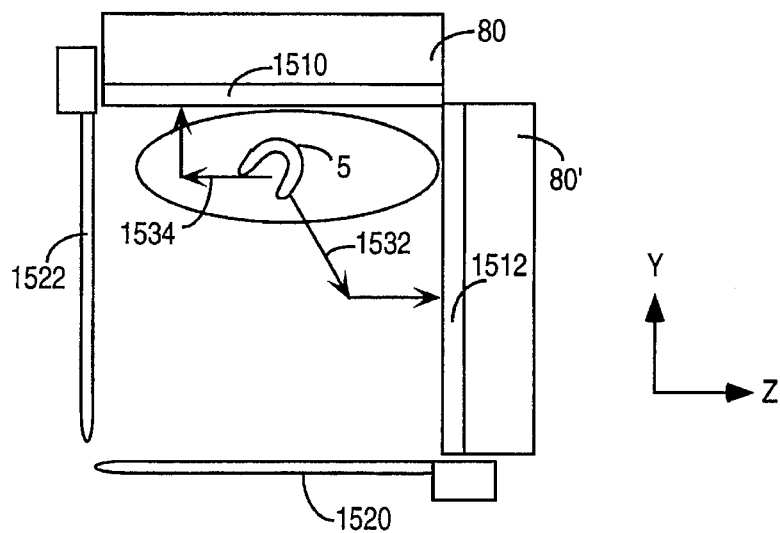
FIG. 13A illustrates emission cross-scatter effects and elimination using an alternative embodiment of the present invention transverse orientation dual line source transmission scanning configuration.
Figure 13A:
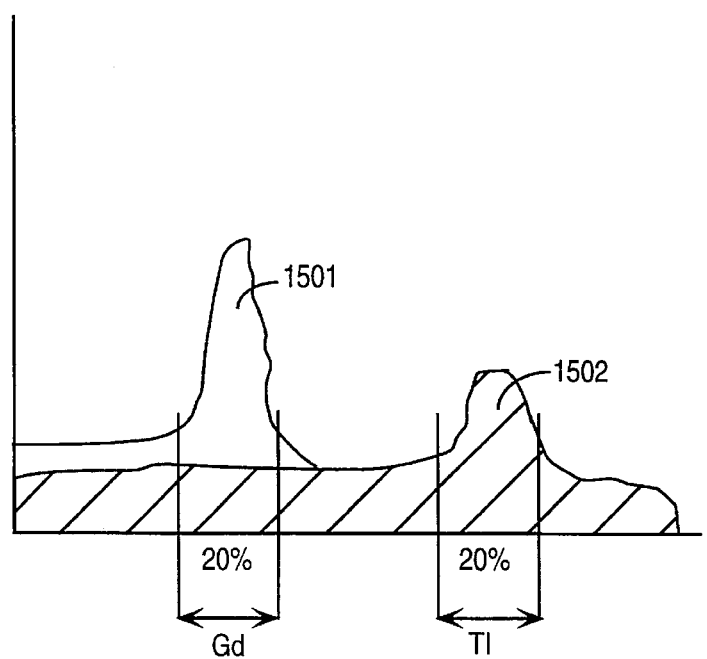

An implementation of the present invention is shown in FIG. 13A wherein the scanning line source system effectively rejects Tl scatter in a Gd window within a system using Tl-201 (at 167-keV) as emission photons and Gd-153 (at 100-keV) is used for transmission. In this configuration, the effects of emission cross-talk are reduced. The resultant Gd transmission image is effectively free of emission cross-scatter contamination. For example, an emission photon may scatter of off the object 5 following in path 1534 and lose energy. The emission photon will then fall within transmission detection window 1510 and will have an energy level of a transmission 100-keV photon. However, the transmission Gd count rate inside the detection window 1510 overwhelms the downscatter from the 167-keV emission cross scatter. The line source collimation and detector collimation ensure that nonscattered transmission radiation falls into the transmission detection window of its associated detector. Gd counts occurring inside the transmission detection windows are accepted and Gd counts outside moving transmission detection windows are rejected because source collimation means no valid Gd photons are outside of the transmission detection windows.

FIG. 13B illustrates the energy distribution of detected photons resultant from the configuration of FIG. 13A. As shown in FIG. 13B, the shaded area 1502 represents the Tl photopeak plus the scatter radiation. As shown, the scatter distribution tails into the transmission Gd window. Also shown in the Gd photopeak distribution 1501.

Figure 14A:
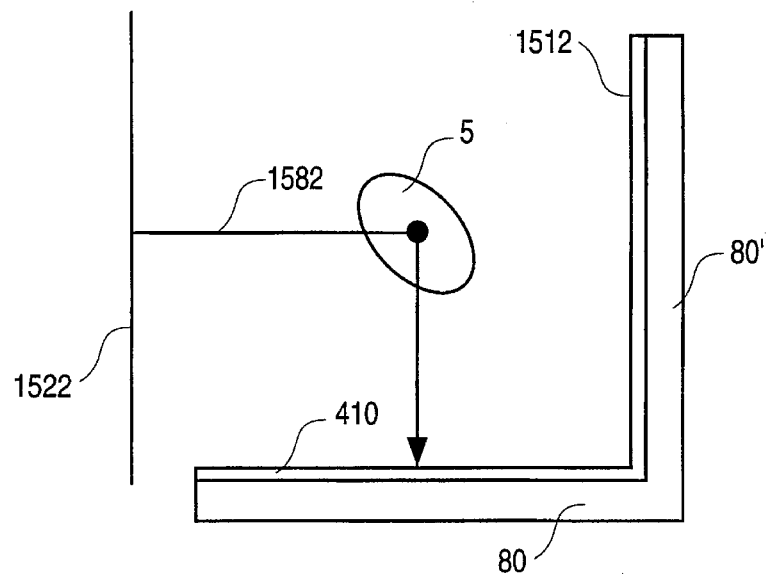
FIG. 14A and FIG. 14B are cross section diagrams illustrating differences between the present invention transverse orientation dual line source transmission scanning configuration and an axial configuration.
Figure 14B:
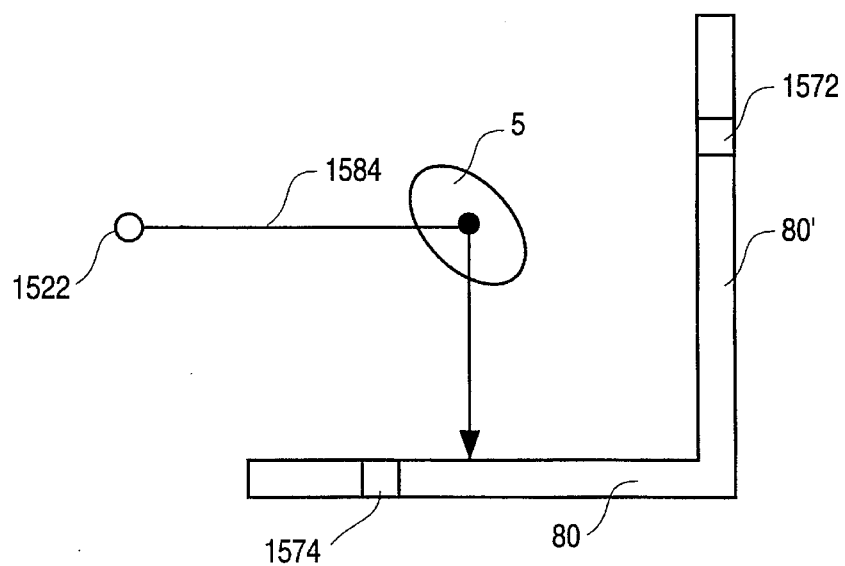

FIG. 14A and FIG. 14B illustrate that the transverse transmission detection window configuration of the present invention is advantageous for reducing cross-scatter wherein an axial orientation of the transmission detection windows is not. Axial orientation means that the long axis of the detection window and the long axis of the patient are along the X axis. FIG. 14A illustrates the present invention configuration wherein the long axis of the line sources and transmission detection windows are oriented transverse with respect to the patient. FIG. 14B illustrates the present invention configuration wherein the long axis of the line sources and transmission detection windows are oriented axial with respect to the patient. For both configurations, an exemplary implementation is the use of Tl-201 for the emission radiation source and Gd-153 as the transmission radiation source.

For example, FIG. 14A illustrates a cross section of the present invention transmission configuration that is sliced along the transmission detection windows in the YZ plane. Within the present invention, the long axis of the line sources and transmission detection windows are oriented transverse to the object (e.g., perpendicular to the X axis). As before, detectors 80' and 80 are at right angles and windows 1512 and 1510 extend along the detector surfaces due to the orientation of the cross section. A transmission photon is emitted from line source 1522, along path 1582 and is scattered within the plane of FIG. 14A and is detected within window 1510 of detector 80. As discussed previously, it will be excluded from the transmission data because transmission detection window 1510 only responds to transmission energy level photons.

However, assume the long axis of the transmission detection windows were oriented axial to the object (e.g., along the X axis). The cross sectional view of FIG. 14B (within the YZ plane) illustrates once again that detectors 80 and 80' are at 90 degree orientation, but the cross section of transmission detection window associated with detector 80' is displayed as area 1572. The cross section of transmission detection window associated with detector 80 is shown as 1574. The long axis of these transmission detection windows 1572 and 1574 extends out of and into the page of FIG. 14B. Also, in this cross section, line source 1522 appears as a circle as shown. Assuming a transmission photon taking path 1584 cross scatters from object 5, it can land on detector 80, but it is not guaranteed to land within transmission detection window 1574. As shown in FIG. 14B, the cross scatter photon lands within the emission recording portion of the FOV of detector 80. In this case, the transmission photon will be improperly detected as a emission photon because the energy loss from the photon due to the scatter will reduce its energy level to that of the emission energy level. Therefore, using traverse scanning line sources and traverse oriented moving transmission detection windows, the cross scatter contamination is not eliminated within the axial oriented transmission detection windows. This is one reason why the present invention utilizes transverse scanning line sources and transverse oriented moving transmission detection windows, in this way, the cross scatter contamination is effectively eliminated.

The present invention transverse dual transmission line source scanning configuration is used to collect uncontaminated transmission data (e.g., free from cross-scatter contamination). The transmission data or "counts" collected by the present invention are stored in a computer memory, such as memory 1102 of computer system 1112 (see FIG. 5). Using well known procedures, the transmission data is convened into nonuniform attenuation correction factors by the computer processor 1101 or processor 1060. These nonuniform attenuation correction factors are also stored in a computer memory, such as memory 1102 or even 1104 of FIG. 5.

A. Combination With Zoom Tracking

An embodiment of the transverse dual sliding detection window and dual transmission line source system of the present invention is advantageously utilized in conjunction with zoom tracking windows that allow detailed images of a particular organ of interest (e.g., such as in cardiac studies). This implementation is particularly advantageous for simultaneous SPECT emission and transmission acquisition. The details of the zoom tracking implementation within a dual detector system are described in U.S. Pat. No. 5,304,806, entitled, "Apparatus and Method for Automatic Tracking of a Zoomed Scan Area in a Medical Camera System," issued Apr. 19, 1994, and assigned to the assignee of the present invention. According to this disclosure, a special zoom window (or region) is defined within the FOV for each detector within the detector electronics and/or computer system's data acquisition processes. This window is defined to cover the field of view of the detector which coincides with a particular organ of an imaged patient, e.g., the heart. The detector electronics provide for an image magnification for emission radiation that are detected within the zoom windows.

As the detectors traverse about the object under ECT movement, the zoom windows displace ("rove") relative to the surface of the detectors so that the heart (or other organ of interest) remains centered and within the FOV of each zoom window. In effect, the zoom windows track the heart for each ECT rotation angle. These zoom windows detect SPECT emission radiation from the tracked organ (e.g., heart) when the camera system is placed in SPECT imaging mode. Since the zoom windows are smaller than the entire FOV of a detector, the image rendering capacity of the gamma camera can be focused on the zoom window and the resultant image generation quality is increased (e.g., resolution is increased). In effect, the size of the pixels defined within the zoom window can be decreased relative to their full FOV size.

Figure 15A:
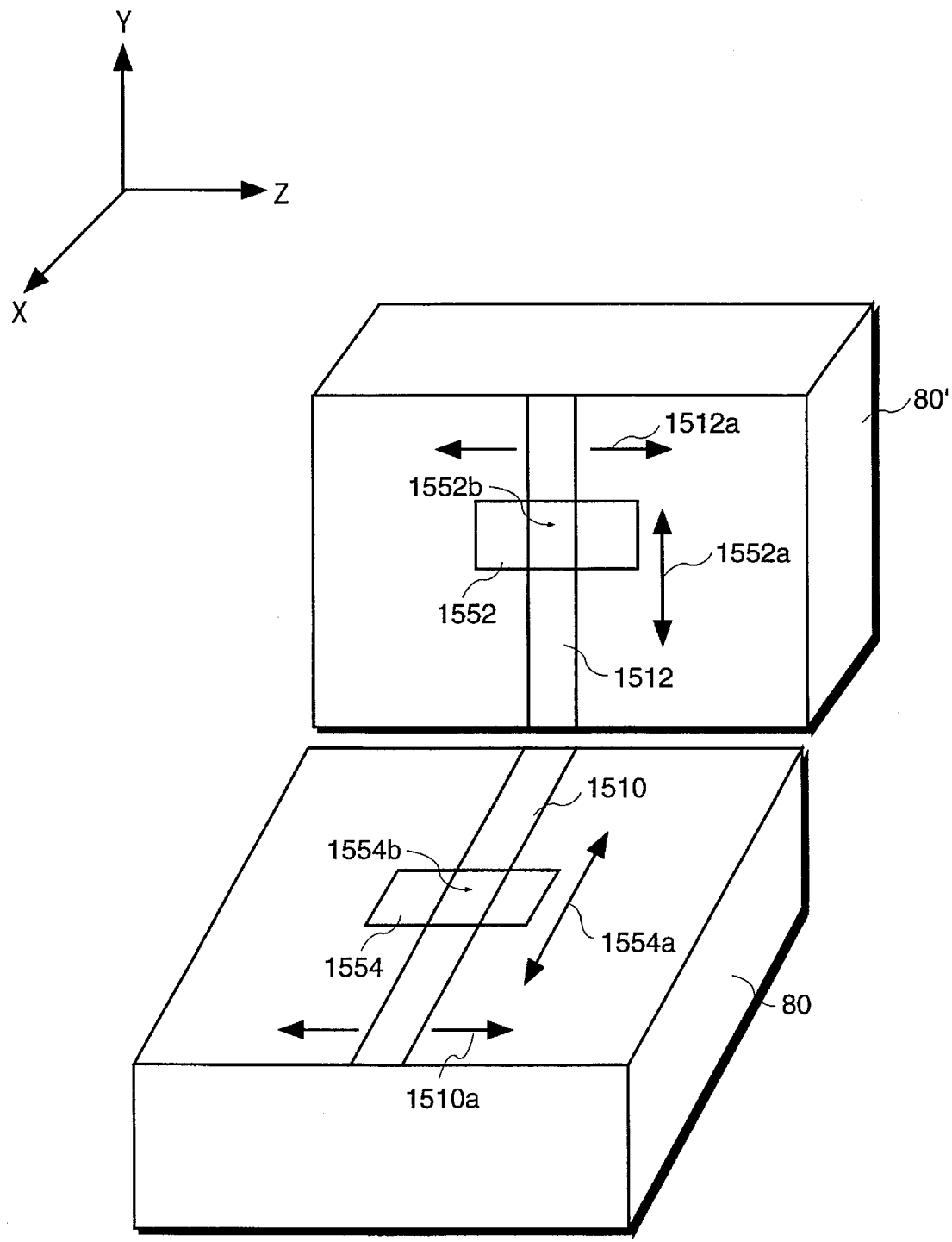
FIG. 15A is an illustration of the tracking zoom windows and the scanning transmission detection windows of the present invention.

FIG. 15A illustrates that zoom tracking is implemented in conjunction with the transverse dual detector transmission window and dual line source scanning configuration of the present invention. In such case, the zoom windows 1552 and 1554 are defined on the surface of the detectors and move up and down as shown by the arrows 1552a and 1554a in order to track an object of interest as the detectors 80 and 80' undergo ECT rotation about the object. It is appreciated that for any given angle, the zoom windows remain fixed and rove only between angles. In an exemplary configuration, the FOV of a particular detector is roughly 51×31 cm in area and a particular zoom window can be 30×30 cm or 38×38 cm in area. The detectors 80 and 80' electronically collect emission data (e.g., counts) only within the zoom regions 1552 and 1554 for each angle of rotation. It is appreciated that the entire FOV of the detector 80 and 80' may be detecting emission radiation, however, only that emission radiation that is detected within the zoom windows (regions) is stored and used for image reconstruction.

According to this aspect of the present invention, simultaneous with the collection of emission data within the two roving zoom windows, transmission data is also collected within the scanning transmission detection windows 1510 and 1512. An exemplary implementation is the use of Tl-201 for the emission radiation source and Gd-153 as the transmission radiation source. Although not shown in FIG. 15A, the two scanning line sources are also present and move in synchronization with the two transmission detection windows. For each angle of rotation, the transverse transmission detection windows scan across the FOV of the detector according to arrows 1512a and 1510a as discussed above in order to collect transmission data. For each angle or rotation, the zoom windows 1552 and 1554 assume a new spatial position (rove) to track the object of interest. However, unlike the scanning transmission detection windows 1512 and 1510, at any given angle of rotation the zoom windows 1552 and 1552 remain fixed until the next angle of rotation is entered.

The transmission detection windows 1510 and 1512 of the present invention report only photons within the transmission energy level and reject other detected photons, e.g., emission energy level photons which result from: (1) scattered transmission photons; and (2) nonscattered emission photons. The zoom regions 1552 and 1554 report emission photons because the collimation of the line sources and the detector provides that no valid transmission data should fall outside the two transmission detection windows 1510 and 1512.

It is possible, as shown in FIG. 15A, for the transmission detection windows 1510 and 1512, as they scan across the FOV of their associated detectors, to partially coincide with the zoom windows 1552 and 1554. When this happens, an area of the zoom windows (e.g., 1552b and 1554b) that overlaps with the transmission detection windows act as a transmission detection window and acts to reject photons of the emission energy level. In effect, regions 1552b and region 1554b collect transmission energy level photons and rejects emission photons. However, this state is temporary as the transmission detection windows are moving across the FOV of the scintillation detectors.

Figure 15B:
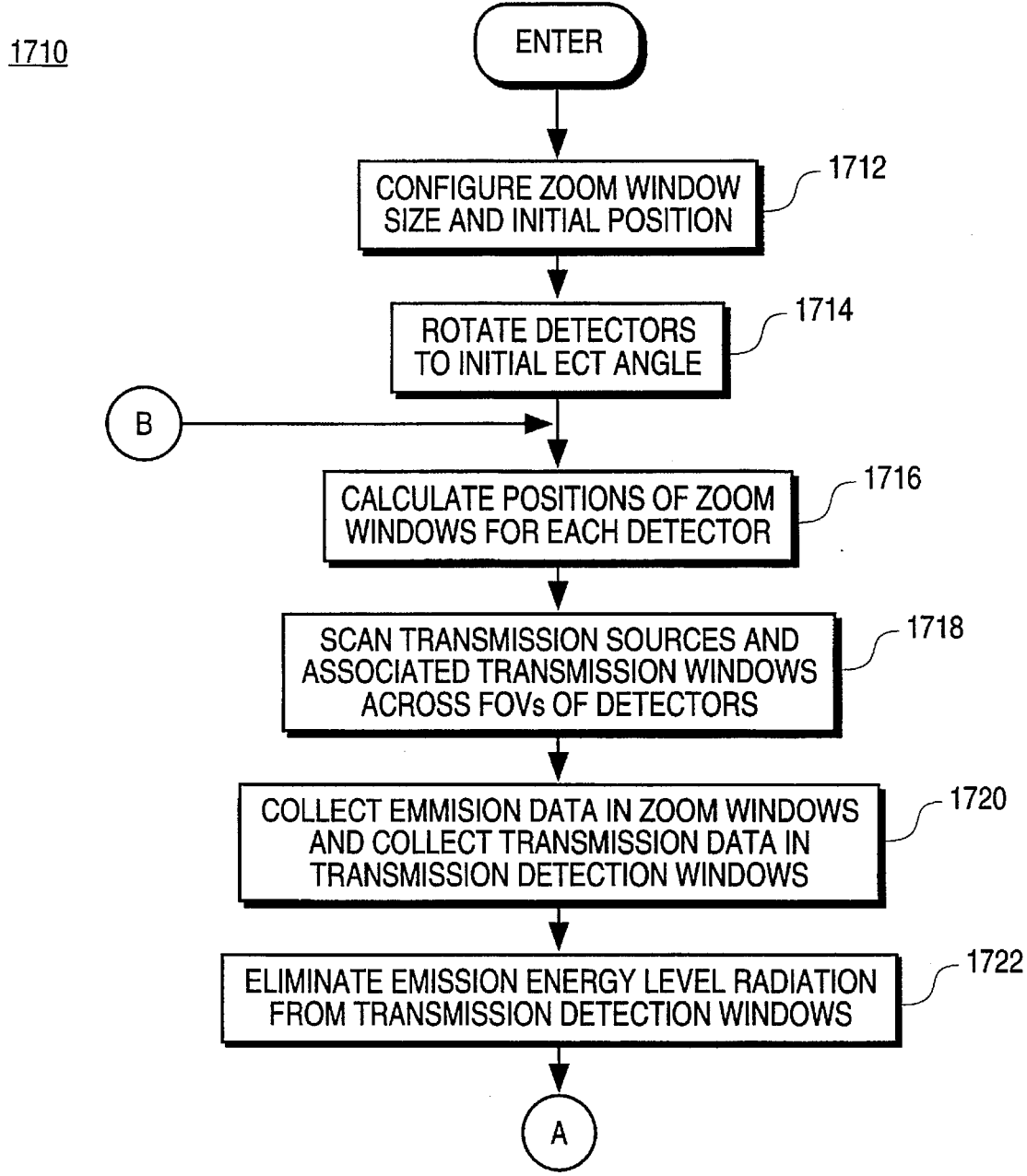
FIG. 15B and FIG. 15C illustrate an operational flow diagram of the tracking zoom region and scanning transmission detection window embodiment of the present invention.
Figure 15C:
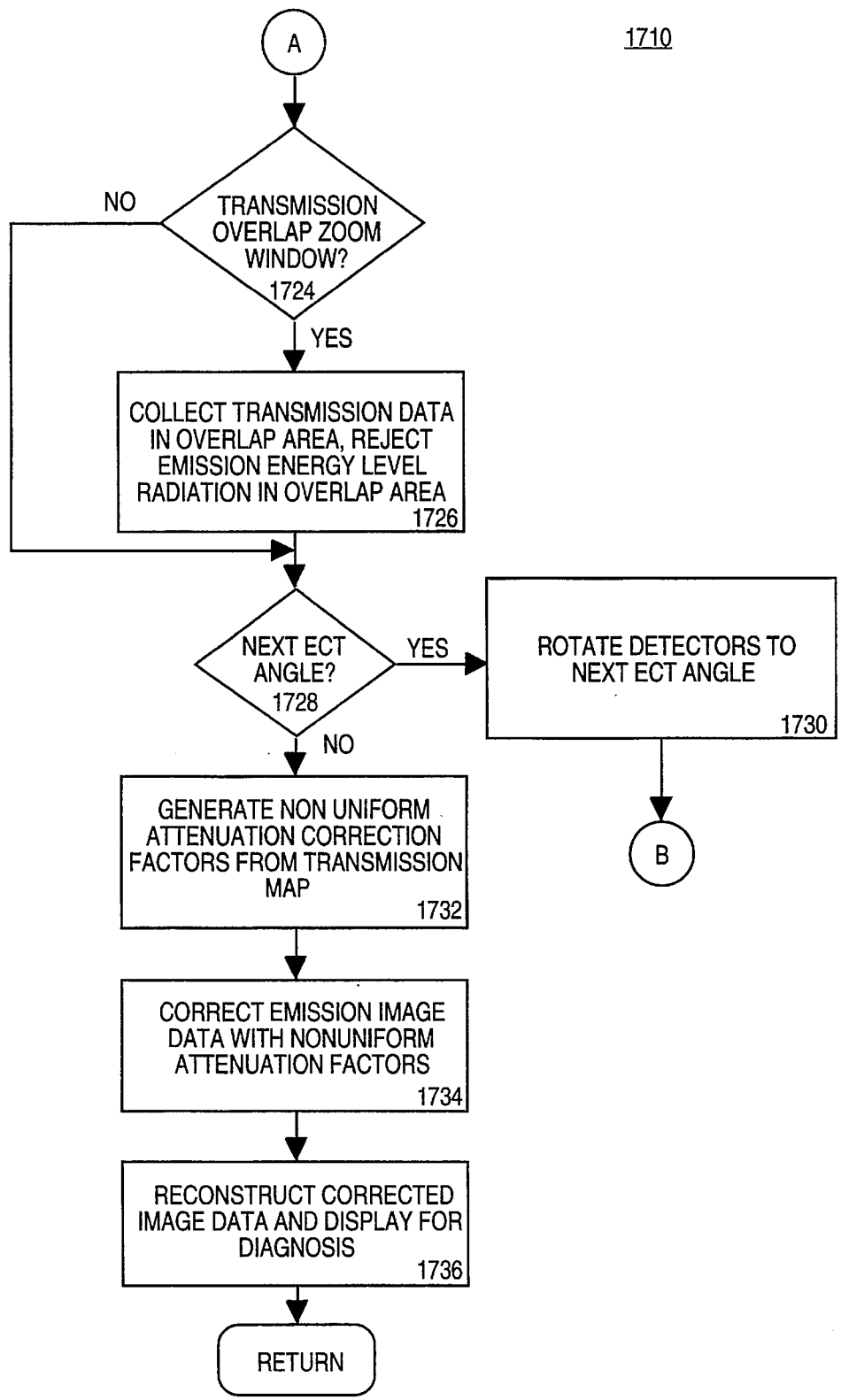

FIG. 15B and FIG. 15C illustrates a flow diagram of the processing tasks 1710 performed by the scanning transmission line source embodiment of the present invention used in conjunction with roving zoom tracking windows for SPECT emission acquisition. An exemplary implementation is the use of Tl-201 for the emission radiation source and Gd-153 as the transmission radiation source. The processing starts at block 1712 in which the patient is placed in the gamma camera system (e.g., such as the one shown in FIG. 1) and the gamma camera is initially configured and initialized for SPECT imaging mode (collimators are installed). The two detectors 80 and 80' are oriented at a 90 degree angle about the patient. At block 1712, the zoom regions are initially defined in terms of size and initial placement in order to locate the object of interest (e.g., the heart); this can be accomplished according to the procedure and mechanisms described in U.S. Pat. No. 5,304,806 (cited above). At block 1714, if not already at the starting angle, the detectors are rotated by the gantry structure to the first angle for the ECT study. At block 1716, the positions of the zoom windows (regions) are computed for each detector for the initial rotation angle; this can be accomplished according to the procedure and mechanisms described in U.S. Pat. No. 5,304,806.

At block 1718, the two scanning line source assemblies 1520 and 1522 scan across the FOV of each detector to irradiate the patient and their associated transmission detection windows scan in synchronization with the associated line source; this process is accomplishing using the configuration shown in FIG. 11A, FIG. 11B, and FIG. 11C. Although programmable, an exemplary scan speed is 1 cm/sec for the configuration. It is appreciated that a scan speed computation (as mentioned above based on a prescan duration) can be performed during this step in order to reduce the radiation exposure amount for the patient.

Block 1720 occurs simultaneously with block 1718. At block 1720, the present invention detects and reports transmission energy level photons (100-keV) within the transmission detection windows (e.g., 1510 and 1512). Simultaneously, emission energy level photons (e.g., 72-keV) are detected and reported within the roving zoom regions (e.g., 1552 and 1554), but transmission energy level photons are rejected (or not detected at all due to collimation of the source and the detectors) within the roving zoom regions.

At block 1722, emission energy level photons (e.g., 72-keV) are rejected within the transmission detection windows 1510 and 1512 (e.g., they can be a result of cross-scatter). Cross-scatter transmission photons are eliminated during this step. It is appreciated that block 1722 can be performed simultaneously with block 1720. At block 1724, the present invention checks if any part of the transmission detection windows overlap with a zoom window as the transmission detection windows scan across the FOV of the detector surfaces. If so, then at block 1726, transmission energy level photons are detected and reported in the overlap area and emission energy level photons are rejected within the overlap area; in effect, the overlap is treated as purely a part of the transmission detection windows. Processing then flows to block 1728. At block 1724, if no overlap, then processing flows to block 1728. It is appreciated that block 1724 and block 1726 can effectively occur simultaneously with block 1722.

At block 1728, the transmission and emission scanning operations for a given ECT angle are completed and the proper transmission and emission image data is stored in computer system 1112 or system 1060. If another ECT angle of rotation is required (e.g., the ECT session is not complete), then at block 1730, the gantry structure rotates the detectors 80 and 80' to a new angle of rotation and block 1716 is once again entered.

If the ECT rotation angles are complete, then the SPECT ECT data acquisition session is over. At block 1732, a nonuniform attenuation correction map is generated based on the transmission data collected for each ECT angle of rotation. At block 1734, the emission data is corrected utilizing well known correction factors (e.g., for linearity and energy) including the nonuniform attenuation correction map generated by block 1734 to correct for nonuniform attenuation of the patient's body. At block 1736, the present invention then reconstructs the corrected emission data (using well known reconstruction procedures) and displays the reconstructed data as required for diagnosis. It is appreciated that the attenuation correction map can be applied during reconstruction as well.

TRANSMISSION WITH PET SCAN

Figure 16A:
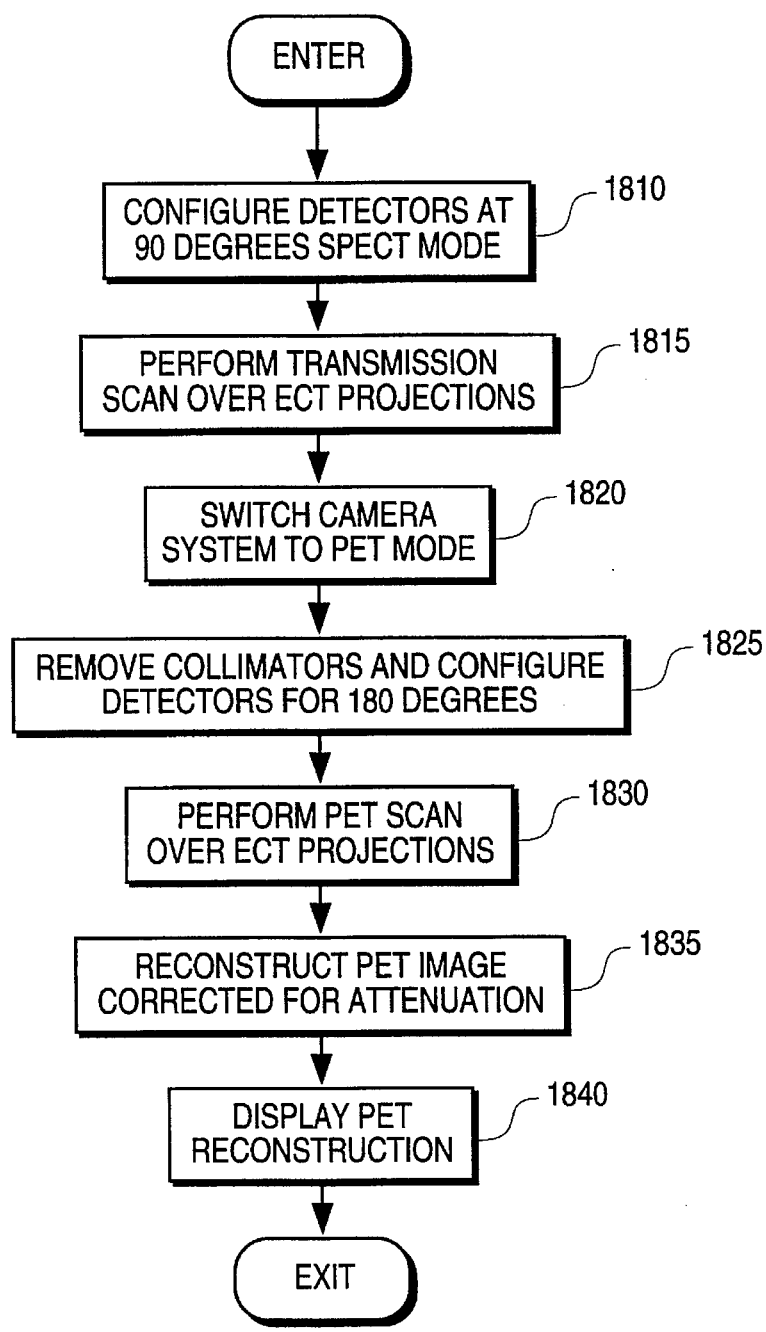
FIG. 16A is a flow diagram for using the dual SPECT/PET camera system of the present invention for collecting PET image data with nonuniform attenuation correction.

FIG. 16A illustrates an exemplary procedure implemented by the camera system of the present invention for (1) performing a transmission data acquisition (with the SPECT/PET camera system in SPECT mode) followed by a (2) PET imaging acquisition with the SPECT/PET camera system reconfigured for PET mode. Using this procedure 1800, the PET image data is corrected for nonuniform attenuation caused by the patient.

Procedure 1800 initiates at block 1810 wherein the dual SPECT/PET camera system is configured for SPECT mode (e.g., blocks 1450 to 1465 of FIG. 10 are performed) and the detector pair are configured at 90 degree configuration with collimators attached (block 1450 of FIG. 10). The patient is oriented within the system. At block 1815, the camera system performs a transmission scan with the dual sliding line sources (in the manner described and shown with respect to FIGS. 11A, 11B, and 11C above). During block 1815, only transmission data over ECT project angles is gathered since the patient is not injected at this time with any radiopharmaceutical. After the transmission data is collected, at block 1820, the dual SPECT/PET camera system is switched to PET imaging mode of operation by following blocks 1410 to 1430 as shown in FIG. 10. In this mode, the collimators are removed from the detector pair as shown in block 1825. Also at block 1825, the patient is injected with a radiopharmaceutical (FDG) for PET imaging and the detectors are configured for 180 degrees.

After a sufficient period of waiting, at block 1830, a PET scan is performed over ECT projections. At block 1835, the projection data from the PET scan is reconstructed and corrected for nonuniform attenuation which is determined from the attenuation correction map collected at block 1815. There are well known procedures for correcting PET images in such manner. At block 1840, a selected portion or "slice" of the reconstructed PET image can be displayed on a display screen. It is appreciated that the PET scan (block 1830) can take place before the transmission scan 1815. In such alternative embodiment, scatter correction procedures are required in order to filter out the high energy counts (from the residual FDG emission) when performing the transmission scan. An energy filter window can be used to accomplish this wherein a high energy scatter reconstruction is subtracted from the transmission reconstruction.

Using procedure 1800, a dual SPECT/PET camera system can be used to collect a PET image and to also collect transmission data for nonuniform attenuation correction to improve the resultant PET image.

TRANSMISSION WITH SPECT SCAN

Figure 16B:
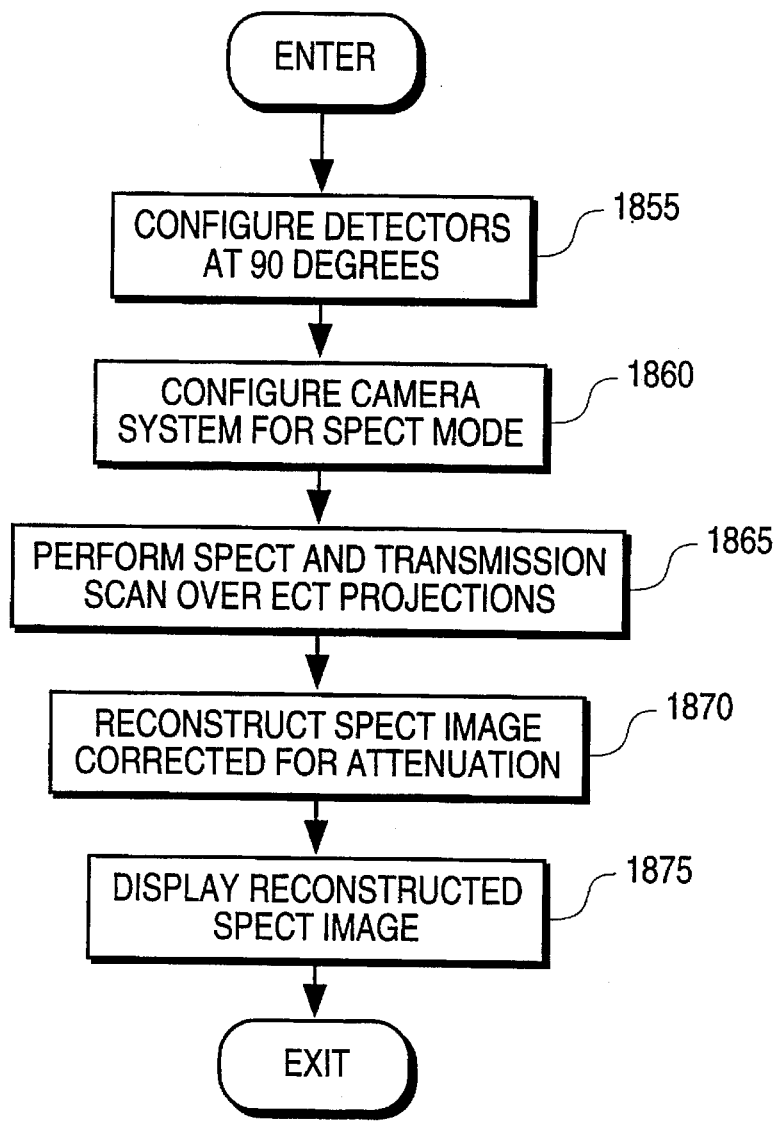
FIG. 16B is a flow diagram for using the dual SPECT/PET camera system of the present invention for collecting a SPECT image with nonuniform attenuation correction.

FIG. 16B illustrates an exemplary procedure implemented by the camera system of the present invention for (1) performing a transmission data acquisition (with the SPECT/PET camera system in SPECT mode) simultaneously with a (2) SPECT imaging acquisition with the SPECT/PET camera system reconfigured for SPECT mode. Using this procedure 1850, the SPECT image data is corrected for nonuniform attenuation.

At block 1855, the camera system's detectors are configured for 90 degrees. At block 1860, the dual SPECT/PET camera system is configured for SPECT mode of imaging (e.g., blocks 1450–1465 of FIG. 10). At block 1860, the patient is injected with a radiopharmaceutical (e.g., emitting about 140 keV gamma rays) for SPECT imaging. After waiting the appropriate time period, at block 1865, the camera system is used for acquiring simultaneous SPECT emission acquisition and transmission acquisition as described above with respect to FIGS. 11A, 11B, and 11C over a number of projection angles. A roving zoom region (as described above) for the SPECT emission acquisition can be used at this stage. At block 1870, a SPECT reconstruction is performed with respect to the emission data acquired over the projection angles. This SPECT reconstruction is corrected for nonuniform attenuation by the attenuation correction maps also collected at block 1865. There are well known procedures for correcting SPECT images in such manner. At block 1875, a selected slice of the corrected SPECT reconstruction is displayed. It is appreciated that in an alternative embodiment, the emission and transmission scans of block 1865 can be sequentially performed.

Using procedure 1850 a dual SPECT/PET camera system can be used to collect a SPECT image and to also collect transmission data for nonuniform attenuation correction to improve the resultant SPECT image.

TRANSMISSION WITH SIMULTANEOUS PET AND SPECT SCAN

Figure 16C:
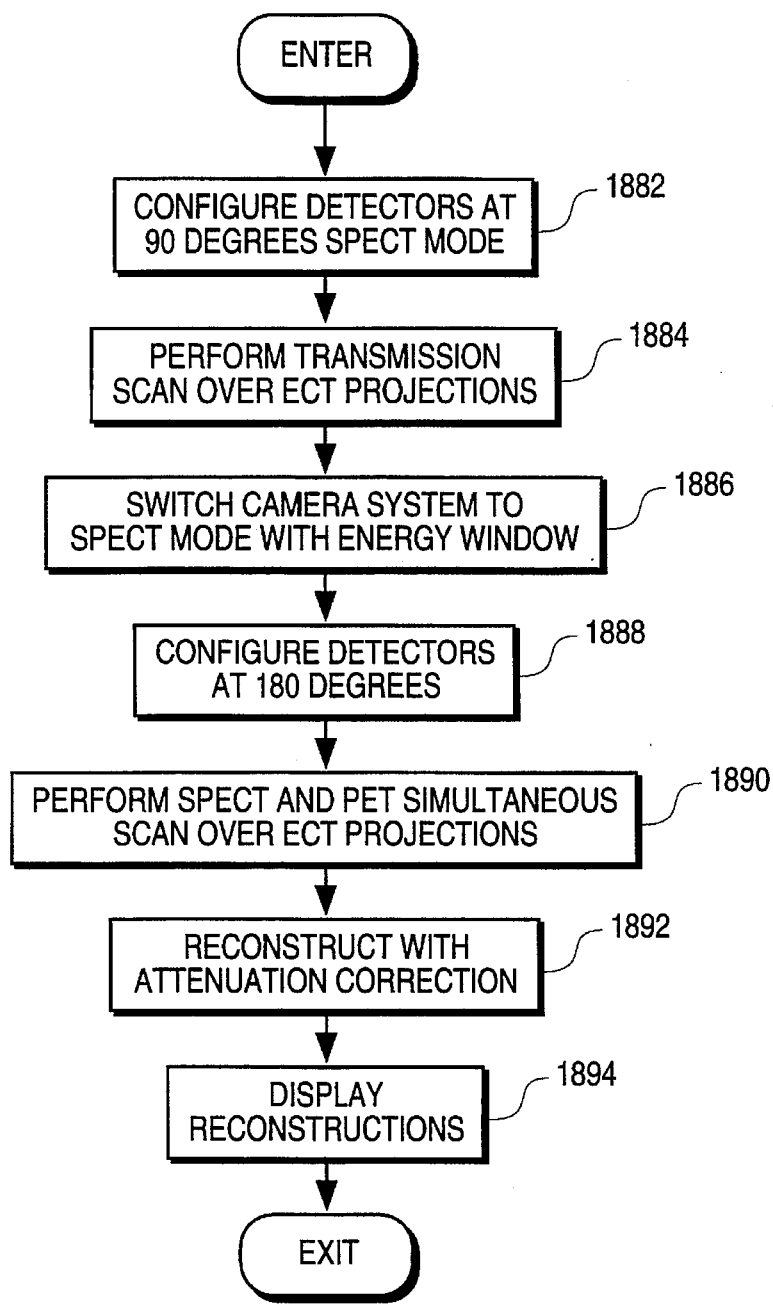
FIG. 16C is a flow diagram for using the dual SPECT/PET camera system of the present invention for collecting a PET and SPECT image with nonuniform attenuation correction.
Figure 17:
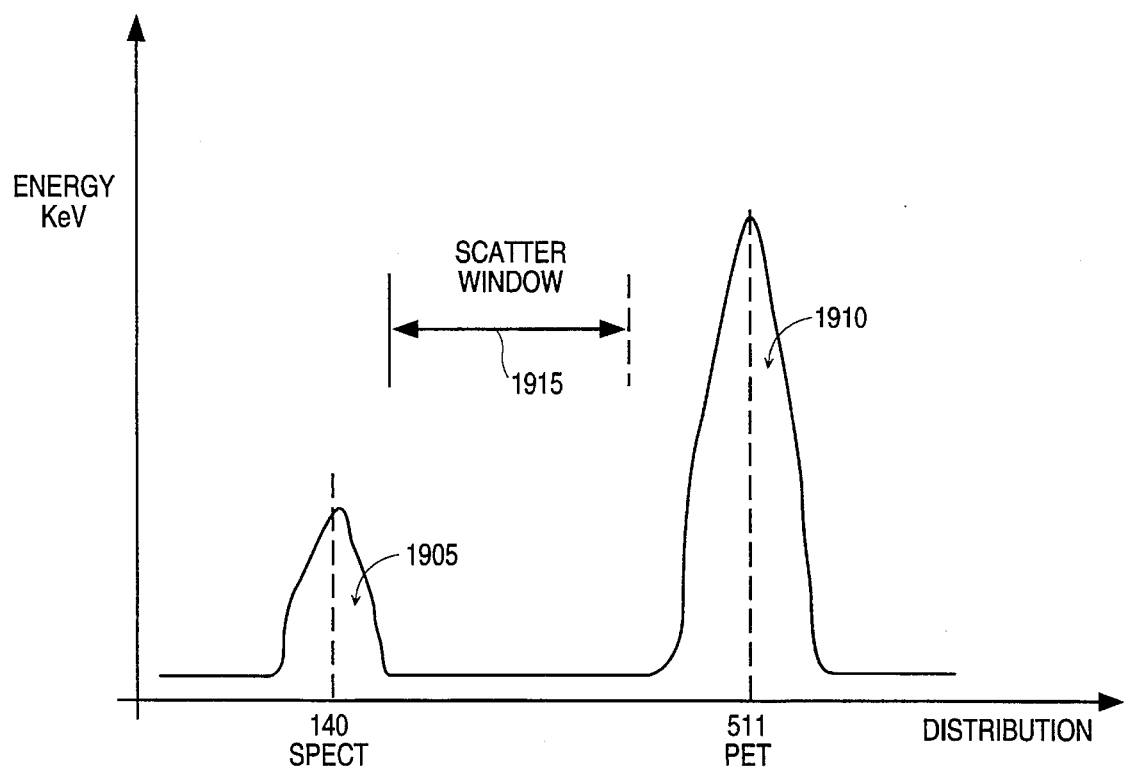
FIG. 17 illustrates photopeaks for SPECT and PET imaging and a scatter window.

FIG. 16C represents a flow diagram of steps performed by the present invention for collecting transmission image information followed by a simultaneous SPECT and PET acquisition. FIG. 17 represents the various energy photopeaks and scatter energy windows used within this embodiment of the present invention. Procedure 1880 of FIG. 16C begins at block 1882 wherein the detectors 80 and 80' are configured at 90 degrees and the camera system is initialized for SPECT mode of operation (see FIG. 10, blocks 1455–1465). Collimators are installed. At block 1864, a transmission scan is performed over ECT projection angles and transmission projection data image data is collected.

At block 1886, the present invention switches the camera system to SPECT mode for simultaneous SPECT and PET acquisition. In this mode, an intermediate integration interval is programmed (e.g., between SPECT and PET mode), such as 600–700 ns, and the coincidence triggering is not activated within CTC 1050. The PMT cluster size is programmed to a small area. An energy window is also programmed into the camera system so that events having a photopeak at or around 511 keV 1910 (see FIG. 17) are detected as SPECT events and events having a photopeak at 140 keV 1905 (see FIG. 17) and recorded in coincidence are detected as PET events. A scatter window 1915 is also programmed to be between the two photopeaks 1905 and 1910. At block 1888 the detectors are configured at 180 degrees. At block 1886, the patient is injected with a PET radiopharmaceutical (detected events at 511 keV) and a SPECT radiopharmaceutical (detected events at 140 keV).

At block 1890, the camera system collects image data for both energy photopeaks and also for the scatter window 1915. In this mode, events are reported by the DEPs of both detectors and they are time stamped as they are recorded. Those events that occur in coincidence (with proper energy level) as recorded in the computer memory are marked as PET events. Compton scattering can cause an event of a PET event pair to be detected with reduced energy level as compared to the expected photopeak. Therefore, a PET event can be detected as a photopeak—Compton scatter pair, in coincidence, according to the present invention. The camera system of the present invention records as a valid PET event pair the following detected energy levels in coincidence: photopeak (detector 80)—photopeak (detector 80'); Compton (detector 80)—photopeak (detector 80'); or photopeak (detector 80)—(detector 80'). For each ECT projection angle, events detected within the energy level at the SPECT energy photopeak 1905 or within the scatter window 1915 are recorded as SPECT events for a SPECT reconstruction. For each ECT projection angle, events detected within the scatter window 1915 are also recorded in a separate image matrix for a separate scatter reconstruction. For each ECT projection angle, a pair of events detected in coincidence both within the PET photopeak energy level 1910, or a pair of events detected in coincidence, one within the PET photopeak energy level and one having a Compton scatter energy level, are recorded within the PET image projection data for the PET reconstruction. This occurs over each projection angle at block 1890.

At block 1892 of FIG. 16C, the projection angles with respect to the SPECT data are reconstructed while being simultaneously corrected by the transmission information collected at block 1884. This is a well known procedure. Also at block 1892, the projection angles with respect to the scatter data are reconstructed while being simultaneously corrected by the transmission information collected at block 1884. The scatter reconstruction data is then subtracted from the SPECT reconstruction. These are well known procedures. Lastly, at block 1892, the projection angles with respect to the PET data are reconstructed while being simultaneously corrected by the transmission information collected at block 1884. The end result is a pair of reconstructions, one for SPECT and one for PET. Various selected "slices" of these reconstructions can then be displayed at block 1894.

It is appreciated that the SPECT and PET imaging sessions at block 1890 do not need to occur simultaneously. That is, alternatively, the PET radiopharmaceutical (FPG, for instance) can be injected into the patient with a PET scan performed which is then followed by an injection of a SPECT pharmaceutical followed by a SPECT scan (after the camera system is reconfigured). In this case, the lower energy levels of the SPECT events can be used to distinguish valid SPECT events from lingering PET events (this would include a scatter correction as described above). Alternatively, the SPECT radiopharmaceutical can be injected into the patient with a SPECT scan performed which is then followed by an injection of a PET pharmaceutical followed by a PET scan (after the camera system is reconfigured). In this case, the higher energy levels of the PET events can be used to distinguish valid PET events from lingering SPECT events.

It is also appreciated that during PET scanning, certain well known corrections can be performed to reduce the error caused by random coincidences (events detected within the coincidence window that are in coincidence at random and did not originate from a single positron electron annihilation). Within the scope of the present invention, the following techniques can be used to reduce the effects of random coincidences: Delayed Event Subtraction, Real-time Subtraction, or Estimation of Ratios of Singles. These are well known correction procedures. On occasion, a photopeak-Compton scatter pair detected in coincidence may not represent a proper PET event, or will represent the event in the wrong location. The present invention can minimize this occurrence by using shielding or septas attached to the detectors or by using a scatter correction technique based on spatially varying de-convolution, as suggested by Bergstrom.

The preferred embodiment of the present invention, a dual head nuclear camera system automatically switchable between SPECT and PET modes of operation having nonuniform attenuation correction is thus described. While the present invention has been described in particular embodiments, it should be appreciated that the present invention should not be construed as limited by such embodiments, but rather construed according to the below claims.

What is claimed is:

1. A switchable SPECT/PET nuclear camera system comprising:

a first detector and a second detector for responding to scintillation events;

circuitry for detecting and recording said events, said circuitry switchable to a first mode of imaging for detection and recordation of PET events and said circuitry switchable to a second mode of imaging for detection and recordation of SPECT events, said circuitry coupled to said first detector and to said second detector, said circuitry including a switchable trigger detection unit that is automatically switchable between coincidence detection when said first mode of imaging is selected and non-coincidence detection when said second mode of imaging is selected, wherein said switchable trigger detection unit is coupled to supply a first valid event trigger signal to said first detector causing said first detector to integrate a scintillation event and coupled to supply a second valid event trigger signal to said second detector causing said second detector to integrate a scintillation event;

transmission radiation sources for scanning across fields of view of said first detector and said second detector with transmission radiation, wherein said circuitry detects and records transmission information while said transmission radiation sources are scanning;

a computer system for generating a PET reconstruction based on said PET events which are corrected by said transmission information; and wherein said computer system is also for generating a SPECT reconstruction based on said SPECT events which are corrected by said transmission information.

2. A nuclear camera system as described in claim 1 wherein said computer system comprises a display screen and a user interface device wherein said computer system displays on said display screen a portion of said PET reconstruction and said SPECT reconstruction as selected by said user interface device.

3. A nuclear camera system as described in claim 1 further comprising a gantry mechanism for configuring said first detector and said second detector at a 90 degree angle during operation of said transmission radiation sources and wherein said gantry mechanism is also for configuring said first detector and said second detector at a 180 degree angle during said detection and recordation of said PET events and during said detection and recordation of said SPECT events.

4. A nuclear camera system as described in claim 1 wherein:

said first detector and said second detector individually comprise event detection units for transmitting indications of scintillation events to said switchable trigger detection unit; and wherein said switchable trigger detection unit generates said first and second valid event trigger signals upon detection of two indications of scintillation events occurring within a coincidence window, one in said first detector and one in said second detector, provided said first mode of imaging is selected.

5. A nuclear camera system as described in claim 4 wherein each of said event detection units corresponds to a zonal area of said first or second detector and each of said event detection units generates an indication of scintillation events occurring within a corresponding zonal area of said first or second detector.

6. A nuclear camera system as described in claim 1 wherein:

said first detector comprises PET event detection units for transmitting indications of scintillation events occurring within said first detector to said switchable trigger detection unit;

said second detector comprises PET event detection units for transmitting indications of scintillation events occurring within said second detector to said switchable trigger detection unit; and wherein said switchable trigger detection unit comprises a coincidence detector coupled to receive said indications of scintillation events occurring within said first detector and coupled to receive said indications of scintillation events occurring within said second detector, said coincidence detector for generating a coincidence signal upon coincidence of said indications of scintillation events occurring within said first detector and said indications of scintillation events occurring within said second detector.

7. A nuclear camera system as described in claim 6 wherein:

said first detector comprises SPECT event detection units for transmitting indications of scintillation events occurring within said first detector to said switchable trigger detection unit; and said second detector comprises SPECT event detection units for transmitting indications of scintillation events occurring within said second detector to said switchable trigger detection unit.

8. A nuclear camera system as described in claim 7 wherein said switchable trigger detection unit further comprises:

a first multiplexer receiving a select signal generated by said computer system and receiving an input from said SPECT event detection units of said first detector and receiving an input from said coincidence detector;

a second multiplexer receiving said select signal and receiving an input from said SPECT event detection units of said second detector and receiving an input from said coincidence detector; and wherein said first multiplexer outputs said first valid event trigger signal to said first detector and wherein said second multiplexer outputs said second valid event trigger signal to said second detector.

9. A nuclear camera system as described in claim 1 wherein said transmission radiation sources further comprise:

a first line source for scanning across a field of view of said first detector;

a second line source for scanning across a field of view of said second detector, wherein said nuclear camera system further comprises:

a first transmission detection window defined within a portion of said field of view of said first detector, said first transmission detection window for receiving transmission radiation originating from said first line source;

a second transmission detection window defined within a portion of said field of view of said second detector, said second transmission detection window for receiving transmission radiation originating from said second line source; and wherein said first line source, said second line source, said first transmission detection window, and said second transmission detection window have individual long axes and wherein all of said individual long axes are contained within a single spatial region.

10. A nuclear camera system as described in claim 9 further comprising:

a scanning mechanism scanning said first line source and said second line source, in synchronization, across said fields of view of said first detector and said second detector;

means for scanning said first transmission detection window across said field of view of said first detector in synchronization with said first line source; and means for scanning said second transmission detection window across said field of view of said second detector in synchronization with said second line source.

11. A nuclear camera system as described in claim 9, wherein said spatial region is a plane.

12. A switchable SPECT/PET mode nuclear camera system comprising:

a first detector and a second detector for responding to scintillation events;

circuitry for detecting and storing said events, said circuitry switchable to a first mode of imaging for detection and recordation of PET events detected by said first detector and said second detector and said circuitry switchable to a second mode of imaging for detection and recordation of SPECT events detected by said first detector and said second detector, said circuitry coupled to said first detector and said second detector;

a gantry mechanism for configuring said first detector and second detector at 90 degree configuration during said second mode of operation, said gantry mechanism for configuring said first detector and said second detector at 180 degree configuration during said first mode of operation; and a computer system coupled to said circuitry and for generating a PET reconstruction based on said PET events; and wherein said computer system is also for generating a SPECT reconstruction based on said SPECT events.

13. A nuclear camera system as described in claim 12 wherein said circuitry comprises:

a switchable trigger detection unit that is automatically switchable between coincidence detection when said first mode of imaging is selected and non-coincidence detection when said second mode of imaging is selected;

said switchable trigger detection unit coupled to supply a first valid event trigger signal to said first detector causing said first detector to record a scintillation event and coupled to supply a second valid event trigger signal to said second detector causing said second detector to record a scintillation event.

14. A nuclear camera system as described in claim 13 wherein:

said first detector and said second detector individually comprise event detection units for transmitting indications of scintillation events to said switchable trigger detection unit; and wherein said switchable trigger detection unit generates said first and second valid event trigger signals upon detection of two indications of scintillation events occurring within a coincidence window, one in said first detector and one in said second detector, provided said first mode of imaging is selected.

15. In a dual SPECT/PET mode of operation nuclear camera system including at least a first detector and a second detector for responding to scintillation events and event detection and recordation circuitry configurable to detect and record SPECT image information or PET image information, a method of generating a nuclear medicine image, said method comprising the steps of:

configuring said first and said second detectors at a 90 degree orientation;

performing a transmission scan of an object about a plurality of rotation angles to collect transmission projection information;

configuring said dual SPECT/PET mode of operation camera system for a PET imaging mode of operation;

configuring said first and second detectors at a 180 degree orientation;

imaging said object with said first detector and said second detector about a plurality of rotation angles to collect PET emission projection information;

correcting for nonuniform attenuation by correcting said PET emission projection information by said transmission projection information; and responsive to said step of correcting, reconstructing a PET image with corrected PET emission projection information to produce a PET reconstruction.

16. A method as described in claim 15 further comprising the step of selecting a portion of said PET reconstruction to be said nuclear medicine image and displaying said nuclear medicine image on a display screen.

17. A method as described in claim 15 wherein said step of configuring said dual SPECT/PET mode of operation camera system for a PET imaging mode of operation comprises the steps of:

loading a PET integration interval into programmable integration circuits associated with said first detector and said second detector;

loading a PET PMT cluster size into a programmable table used for centroid computation; and instructing said event detection and recordation circuitry to recognize valid detected events that are detected within a coincidence window.

18. A method as described in claim 15 wherein said step of performing a transmission scan comprises the steps of:

scanning a first line source across a field of view of said first detector;

scanning a second line source across a field of view of said second detector;

scanning a first transmission detection window on a surface of said first detector in synchronization with said first line source, wherein said first transmission detection window receives transmission radiation originating from said first line source;

scanning a second transmission detection window on a surface of said second detector in synchronization with said second line source, wherein said second transmission detection window receives transmission radiation originating from said second line source; and wherein said first line source, said second line source, said first transmission detection window, and said second transmission detection window have individual long axis and containing all of said individual long axis within a single spatial plane perpendicular to a long axis of said object during said scanning.

19. In a dual SPECT/PET mode of operation nuclear camera system including at least a first detector and a second detector responsive to scintillation events, and event detection and recordation circuitry configurable to detect and record SPECT image information or PET image information, a method of generating a nuclear medicine image comprising the steps of:

configuring said first and second detectors at a 90 degree orientation;

configuring said dual SPECT/PET operation camera system for a SPECT imaging mode of operation;

performing a transmission scan of an object about a plurality of rotation angles to collect transmission projection information;

imaging said object with said first detector and said second detector about a plurality of rotation angles to collect SPECT emission projection information;

correcting for nonuniform attenuation by correcting said SPECT emission projection information by said transmission projection information; and responsive to said step of correcting, reconstructing a SPECT image with corrected SPECT emission projection information to produce a SPECT reconstruction.

20. A method as described in claim 19 further comprising the step of selecting a portion of said SPECT reconstruction to be said nuclear medicine image and displaying said nuclear medicine image on a display screen.

21. A method as described in claim 19 wherein said step of configuring said dual SPECT/PET operation camera system for a SPECT imaging mode of operation comprises the steps of:

loading a SPECT integration interval into programmable integration circuits associated with said first detector and said second detector;

loading a SPECT PMT cluster size into a programmable table used for centroid computation; and instructing said event detection and recordation circuitry to recognize valid detected events not in coincidence.

22. A method as described in claim 19 wherein said step of performing a transmission scan comprises the steps of:

scanning a first line source across a field of view of said first detector;

scanning a second line source across a field of view of said second detector;

scanning a first transmission detection window on a surface of said first detector in synchronization with said first line source, wherein said first transmission detection window receives transmission radiation originating from said first line source;

scanning a second transmission detection window on a surface of said second detector in synchronization with said second line source, wherein said second transmission detection window receives transmission radiation originating from said second line source; and wherein said first line source, said second line source, said first transmission detection window, and said second transmission detection window have individual long axes, and wherein all of said individual long axes are contained within a single spatial region perpendicular to a long axis of said object during said scanning.

23. A method as described in claim 22, wherein said spatial region is a plane.

24. A method as described in claim 19 wherein said steps of performing a transmission scan and imaging said object with said first detector and said second detector about a plurality of rotation angles to collect SPECT emission projection information occur simultaneously.

25. A method as described in claim 19 wherein said step of imaging said object with said first detector and said second detector about a plurality of rotation angles to collect SPECT emission projection information further comprises the steps of:

rotating said first detector and said second detector to an angle of rotation for an ECT scan;

determining a first zoom window within a portion of a surface of said first detector based on said angle of rotation wherein said object is within a field of view of said first zoom window;

determining a second zoom window within a portion of a surface of said second detector based on said angle of rotation wherein said object is within a field of view of said second zoom window; and collecting emission data detected within said first zoom window and said second zoom window for said angle of rotation.

26. A method a described in claim 25 further comprising the step of collecting only transmission data detected within an area of overlap between said first zoom window and a first transmission detection window and collecting only transmission data detected within an area of overlap between said second zoom window and a second transmission detection window.

27. In a multi-detector dual SPECT/PET operation nuclear camera system including at least a first detector and a second detector responsive to scintillation events, and event detection and recordation circuitry configurable to detect and record SPECT image information or PET image information, a method of generating a nuclear medicine image comprising the steps of:

configuring said first and second detectors at a 90 degree configuration;

performing a transmission scan of an object about a plurality of rotation angles to collect transmission projection information;

configuring said dual SPECT/PET operation camera system for simultaneous acquisition of both PET and SPECT event data;

imaging said object with said first detector and said second detector about a plurality of rotation angles to simultaneously collect both SPECT and PET emission projection information;

correcting both said SPECT and said PET emission projection information for nonuniform attenuation using said transmission projection information to generate corrected SPECT emission projection information and corrected PET emission projection information; and reconstructing a SPECT image with said corrected SPECT emission projection information to produce a SPECT reconstruction;

reconstructing a PET image with said corrected PET emission projection information to produce a PET reconstruction.

28. A method as described in claim 27 further comprising the step of selecting a portion of said PET reconstruction to be said nuclear medicine image and displaying said nuclear medicine image on a display screen.

29. A method as described in claim 27 further comprising the step of selecting a portion of said SPECT reconstruction to be said nuclear medicine image and displaying said nuclear medicine image on a display screen.

30. A method as described in claim 27 wherein said step of configuring said dual SPECT/PET operation camera system for a simultaneous acquisition of both PET and SPECT event data comprises the steps of:

loading an intermediate integration interval into programmable integration circuits associated with said first detector and said second detector;

loading a SPECT PMT cluster size into a programmable table used for centroid computation.

31. A method as described in claim 27 wherein said step of performing a transmission scan comprises the steps of:

scanning a first line source across a field of view of said first detector;

scanning a second line source across a field of view of said second detector;

scanning a first transmission detection window on a surface of said first detector in synchronization with said first line source, wherein said first transmission detection window receives transmission radiation originating from said first line source; scanning a second transmission detection window on a surface of said second detector in synchronization with said second line source, wherein said second transmission detection window receives transmission radiation originating from said second line source; and wherein said first line source, said second line source, said first transmission detection window, and said second transmission detection window have individual long axes and wherein all of said individual long axes are contained within a single spatial region perpendicular to a long axis of said object during said scanning.

32. A method as described in claim 31, wherein said spatial region is a plane.

33. A nuclear camera system comprising:

(a) a user selectable operational mode between PET imaging and SPECT imaging;

(b) a pair of scintillation detectors for reporting a pair of events occurring in coincidence for said PET imaging and for reporting events individually for said SPECT imaging, each of said pair of scintillation detectors including:

an array of photomultipliers, individual photomultipliers for generating output channel signals indicative of energy detected by said individual photomultipliers, wherein said array of photomultipliers is divided into zones;

a first plurality of event detection circuits wherein each of said event detection circuits receive channel signals from a particular zone of said zones of said array of photomultipliers; and a first trigger circuit coupled to said first plurality of event detection circuits for generating a trigger signal upon receiving an event indication from any event detection circuit of said first plurality of event detection circuits;

(c) a nonuniform attenuation correction mechanism including transmission radiation sources for scanning said first detector and said second detector with transmission radiation, wherein said circuitry reports and stores transmission information while said transmission radiation sources are scanning;

(d) a computer system for generating a PET reconstruction based on said PET events which are corrected by said transmission information, said computer system is also for generating a SPECT reconstruction based on said SPECT events which are corrected by said transmission information.

34. A nuclear camera system as described in claim 33 wherein said transmission radiation sources further comprise:

a first line source for scanning across a field of view of said first detector; and a second line source for scanning across a field of view of said second detector; wherein said nuclear camera system further comprises:

a first transmission detection window defined within a portion of said field of view of said first detector, said first transmission detection window for receiving transmission radiation originating from said first line source;

a second transmission detection window defined within a portion of said field of view of said second detector, said second transmission detection window for receiving transmission radiation originating from said second line source; and wherein said first line source, said second line source, said first transmission detection window, and said second transmission detection window have individual long axes and wherein all of said individual long axes are contained within a single spatial region.

35. A nuclear camera system as described in claim 34 further comprising:

a scanning mechanism for scanning said first line source and said second line source, in synchronization, across said fields of view of said first detector and said second detector;

means for scanning said first transmission detection window across said field of view of said first detector in synchronization with said first line source; and means for scanning said second transmission detection window across said field of view of said second detector in synchronization with said second line source.

36. A nuclear camera system as described in claim 34, wherein said spatial region is a plane.

* * * * *

UNITED STATES PATENT AND TRADEMARK OFFICE
Certificate

Patent No. 5,608,221                                                                                    Patented: March 4, 1997

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Hugo Bertelsen, Horace H. Hines, Matthew J. Murphy, Peter Nellemann, Donald R. Wellnitz, Gerd Muehllehner and Michael Geagan.

Signed and Sealed this Fifteenth Day of June, 1999.

<div style="text-align:right">

BRIAN W. BROWN
*Special Program Examiner*
Technology Center 2800
Semiconductors, Electrical
and Optical Systems </div>